(12) United States Patent
Muraki et al.

(10) Patent No.: US 6,800,059 B2
(45) Date of Patent: Oct. 5, 2004

(54) VITAL SIGN BOX, MEDIUM, AND INFORMATION AGGREGATION

(75) Inventors: Kyoko Muraki, Kyoto (JP); Norio Saeki, Nara (JP); Junji Tsutsui, Atsugi (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 86 days.

(21) Appl. No.: 09/742,196

(22) Filed: Dec. 20, 2000

(65) Prior Publication Data

US 2002/0115912 A1 Aug. 22, 2002

(51) Int. Cl.⁷ .............................................. A61B 5/02
(52) U.S. Cl. ....................................... 600/300; 600/301
(58) Field of Search .............................. 600/200, 300, 600/301, 347, 412, 474, 502, 438, 508, 509, 549; 250/580, 582, 370.09, 307.14; 378/98.8

(56) References Cited

U.S. PATENT DOCUMENTS

| | | | | |
|---|---|---|---|---|
| 5,724,025 A | * | 3/1998 | Tavori | 340/573.1 |
| 5,745,165 A | | 4/1998 | Atsuta et al. | |
| 5,852,296 A | | 12/1998 | Tsukamoto et al. | 250/370.09 |
| 2002/0004629 A1 | * | 1/2002 | Natori | 600/300 |
| 2002/0010596 A1 | * | 1/2002 | Matory | 705/2 |
| 2002/0165443 A1 | * | 11/2002 | Mori | 600/407 |

FOREIGN PATENT DOCUMENTS

| | | | | |
|---|---|---|---|---|
| JP | 55-034837 | | 3/1980 | |
| JP | 56561 | * | 2/1992 | H04M/11/00 |
| JP | 57161 | * | 2/1992 | G06F/15/21 |
| JP | 7560 | * | 1/1995 | H04M/11/00 |
| JP | 07-204114 | | 8/1995 | |
| JP | 08-332170 | | 12/1996 | |
| JP | 09-294784 | | 11/1997 | |
| JP | 10-10237 | | 1/1998 | |
| JP | 89802 | * | 4/1999 | A61B/5/00 |
| JP | 120242 | * | 4/1999 | G06F/17/60 |
| JP | 151210 | * | 6/1999 | H04N/7/18 |
| JP | 83907 | * | 3/2000 | A61B/5/00 |
| JP | 258857 | * | 9/2001 | A61B/5/00 |
| JP | 56099 | * | 2/2002 | G06F/17/60 |

OTHER PUBLICATIONS

Matsushita Technical Journal vol. 45, No. 5 "Vital Sign Box", pp. 1–18, Oct., 1999.

* cited by examiner

Primary Examiner—Henry C. Yuen
Assistant Examiner—Hai Huynh
(74) Attorney, Agent, or Firm—RatnerPrestia

(57) ABSTRACT

An vital sign box has a plurality of vital sensors measuring predetermined biological, chemical, or physical conditions of a living body; an camera taking a picture of a predetermined object; and a housing containing the plurality of vital sensors and the camera.

49 Claims, 36 Drawing Sheets

Fig. 7

◆ INPUT YOUR NAME AND CONFIRM IT FINALLY.

| YA | A |
|---|---|
| YU | I |
| YO | U |
| ゛ | E |
| ゜ | O |

NAME: MATSUSHITA-

| WA | RA | YA | MA | HA | NA | TA | SA | KA | A |
|---|---|---|---|---|---|---|---|---|---|
|    | RI |    | MI | HI | NI | CHI | SHI | KI | I |
| WO | RU | YU | MU | HU | NU | TSU | SU | KU | U |
|    | RE |    | ME | HE | NE | TE | SE | KE | E |
| N  | RO | YO | MO | HO | NO | TO | SO | KO | O |

NAME
CONVER-SION
NUMBER

| 1 | 2 | 3 | 4 | 5 | 6 | 7 | 8 | 9 | 0 |

CANCEL    CONFIRMED    RETURN

END

SCREEN 1-1

Fig. 8

◆ INPUT PASSWORD AND CONFIRM IT FINALLY.

PASSWORD, 4 DIGITS 9 6 - -

| WA | RA | YA | MA | HA | NA | TA | SA | KA | A |
|----|----|----|----|----|----|----|----|----|----|
|    | RI |    | MI | HI | NI | CHI | SHI | KI | I |
| WO | RU | YU | MU | HU | NU | TSU | SU | KU | U |
|    | RE |    | ME | HE | NE | TE | SE | KE | E |
| N  | RO | YO | MO | HO | NO | TO | SO | KO | O |

|    | A | I | U | E | O |
|----|---|---|---|---|---|
| YA |   |   |   |   |   |
| YU |   |   |   |   |   |
| YO |   |   |   |   |   |
| 〃 |   |   |   |   |   |

NAME

NUMBER

RETURN

END

CANCEL    CONFIRMED

SCREEN 1-2

◆ SELECT A BUTTON.

1. ARE BODY CONDITIONS GOOD?   YES   NO

2. HAVE YOU GOOD TASTE?   YES   NO

3. DID YOU HAVE GOOD SLEEP, LAST NIGHT?   YES   NO

4. HAVE YOU A BOWEL MOVEMENT?   DAILY   ONCE/TWO DAYS   ONCE/THREE DAYS   LESS THAN THEM

GRANDFATHER

10:31 AM ON NOV/11/'98

RETURN   END

CONFIRMED

SCREEN 5-1

Fig. 27

◆ INPUT PARTNER'S NAME AND PHONE NUMBER, AND FINALLY CONFIRM THEM.

| NAME | | PHONE NUMBER | |
|---|---|---|---|
| MATSUSHITA SHIKA-- | | 06-000-0123 | |

INQUIRY [YES] [NO]  DATA TRANSMISSION [YES] [NO]

| YA | A |
|---|---|
| YU | I |
| YO | U |
| 〃 | E |
| ° | O |

| WA | RA | YA | MA | HA | NA | TA | SA | KA | A |
|---|---|---|---|---|---|---|---|---|---|
|    | RI |    | MI | HI | NI | CHI| SHI| KI | I |
| WO | RU | YU | MU | HU | NU | TSU| SU | KU | U |
|    | RE |    | ME | HE | NE | TE | SE | KE | E |
| N  | RO | YO | MO | HO | NO | TO | SO | KO | O |

[NAME]
[CONVER-SION]
[NUMBER]

| 1 | 2 | 3 | 4 | 5 | 6 | 7 | 8 | 9 | 0 |

[CANCEL] [CONFIRMED] [RETURN] [END]

SCREEN 5-2

Fig. 28

◆ INPUT PHONE NUMBER, AND CONFIRM IT.

PHONE NUMBER
06-000-0---

| 1 | 2 | 3 | 4 | 5 | 6 | 7 | 8 | 9 | 0 |

CANCEL  CONFIRMED  RETURN  END

SCREEN 5-3

VITAL SIGN BOX, MEDIUM, AND INFORMATION AGGREGATION

BACKGROUND OF THE INVENTION

1. Field of the Invention

The present invention relates to an vital sign box housing a plurality of vital sensors such as an electrocardiograph and a blood pressure monitor.

2. Description of the Related Art

Recently, in connection with high concern about health and the coming of super aged society, for the grip of health conditions, for example, electrocardiographs and blood pressure monitors that can measure electrocardio and blood pressure in home have been developed. Medical care equipment such an electrocardiograph or a blood pressure monitor is called a vital sensor, and the vital sensor utilized in home is miniaturized, and hence can be carried. Furthermore, vital sign boxs, each of which houses such a plurality of miniaturized vital sensors in one housing, have been also developed. FIG. 36 is a perspective view showing an vital sign box used in Medi Data that is an online medical check system developed by SECOM Co. Ltd./SECOM home medical care system Co., Ltd.

In addition, in connection with the diffusion of multimedia, systematization of home medical care, telemedicine, and remote house visit is requested.

As a system for such requests, the above-described Medi Data. of SECOM Co., Ltd./SECOM home medical care system Co., Ltd. is known. Medi Data is a system that the above-described vital sign box is connected to a nurse center via a communication line, for example, a patient in home medical care measures the Patient's own blood pressure with using a vital sensor contained in the vital sign box to transmit the measurement to the nurse center. Furthermore, in the nurse center, the measurement is received and stored, and the transition of the measurements is reported to a doctor, who performs telemedicine with using a telephone and the like on the basis of the measurements that the doctor are reported.

In addition, as another system performing the home medical care and telemedicine, a home medical care support system by Fukuda Denshi Co., Ltd. is also known. The system consists of home terminal equipment that is installed in home and to which a plurality of vital sensors and a camera to take a picture of patient's appearance such as a face and the like in home medical care are connected, and transmits the patient's images via a communication line with measurements measured by the vital sensors to a center. The center grips not only the measurements measured by the vital sensors, but also the patient's appearance. In addition, by providing a camera in the center and letting faces of a doctor and a nurse in the center know the patient, it is possible to remove the patient's anxiety for the telemedicine. Furthermore, by providing each talking unit in the home terminal equipment and the center, it is possible to perform communication by voice.

However, a camera for taking a picture of patient's appearance such as a face and the like is not provided in the conventional vital sign box used in Medi Data that is an online medical check system made by SECOM Co., Ltd./SECOM home medical care system Co., Ltd. On the other hand, in the home medical care support system made by Fukuda Denshi Co., Ltd., a camera can be connected to home terminal equipment. But, since the camera is used with being fixed in substance and is not a handy type camera, after it is fixed once, it is possible just to take a picture of an object in a viewing angle range to some extent. Nevertheless, it is not possible to take a picture of, for example, a patient's face sometimes, and to take a picture of the patient's foot locally in another time.

In addition, in the above-described conventional vital sign boxs, an input of a measurement measured by each vital sensor is performed by manually inputting the measurement with using a ten-key pad after a user confirms the measurement. The manual input of the measurement using the ten-key pad in this manner is troublesome work for a user, and a mishit may be performed. Furthermore, there is also a possibility of false inputting a measurement.

Moreover, each of the above-described conventional vital sign boxs includes memory to record measurements measured by each vital sensor, and a display for displaying, for example, the transition of measurements for 30 days in a graph. Nevertheless, daily drifts of measurements may not be expressed clearly in the graph displayed in the display. For example, in case a display area is too large in comparison with the largeness of drifts or a display scale is not suitable, daily drifts of measurements are not expressed clearly.

In addition, in a conventional vital sign box, although it is possible to display a measurement measured by each vital sensor in a display, for example, a user having poor eyesight may feel resistance to looking at a displayed measurement. Thus, depending on a user or a using status, it may be more convenient to let the user auditorily inform the measurement by sound than to visually display the measurement in a display.

Furthermore, in the above-described conventional vital sign box, it is possible to transmit a measurement, measured by each vital sensor, to an administration section such as a nurse center via a communication line. Nevertheless, since, for example, a camera for taking a picture of an affected part and the like of a patient in home medical care is not provided, it is not possible to transmit such an image to the administration section.

Furthermore, in the above-described conventional vital sign box, it is possible to transmit a measurement, measured by each vital sensor, to an administration section such as a nurse center via a communication line. Nevertheless, in case of telemedicine, after having received a measurement, it is necessary for a doctor and a nurse in the administration section to inquire a user of the vital sign box, who transmitted the measurement, about health conditions with a telephone or the like. However, if answers to inquiry items have been transmitted to the administration section with the measurements, measured by each vital sensor, beforehand, it becomes unnecessary for a doctor and a nurse in the administration section to inquire the sender. Hence they can have a time margin for medical practice.

SUMMARY OF THE INVENTION

An object of the present invention is to provide an vital sign box which has means of being able to take a picture of an object with changing the object and/or an imaging angle flexibly, in consideration of a subject that, in a conventional vital sign box, a camera taking a picture of an object is not provided, and even if home terminal equipment has a capability for connecting a camera, it is not possible to flexibly change an imaging object and/or an imaging angle.

In addition, another object of the present invention is to provide an vital sign box, having vital sensors which can input measurements into memory without letting a user manually input the measurements, in consideration of a subject that, in a conventional vital sign box, a use is made to manually input the measurements when inputting the measurements, measured by the vital sensors, into memory.

Furthermore, still another object of the present invention is to provide an vital sign box, having a display to clearly display drifts of measurements which have been measured by the vital sensors and have been recorded in a predetermined period, in consideration of a subject that, in a display of a conventional vital sign box, the drifts of the measurements measured and recorded in the predetermined period may not be clearly displayed.

Moreover, a further object of the present invention is to provide an vital sign box having a speaker, outputting measurements, measured by vital sensors, with using sound, in consideration of a subject that measurements measured by vital sensors are not outputted by sound in a conventional vital sign box.

In addition, a still further object of the present invention is to provide an vital sign box not only having means of taking a picture of an object but also being able to transmit an image of the object, that is taken by the imaging means, to a communication partner, in consideration of a subject that, in a conventional vital sign box, for example, a camera taking a picture of an affected part and the like of a patient in home medical care is not provided. Furthermore, an object of the present invention is also to provide an vital sign box that receives information from a communication partner and can perform bi-directional communication.

Moreover, another object of the present invention is also to provide an vital sign box that inquires a user of the vital sign box about health conditions, in consideration of a subject that a conventional vital sign box does not inquire the user of the vital sign box about health conditions.

The $1^{st}$ invention of the present invention (corresponding to claim 1) is an vital sign box comprising: a plurality of vital sensors measuring predetermined biological, chemical, or physical conditions of a living body; an camera taking a picture of a predetermined object; and a housing containing the plurality of vital sensors and the camera.

The $2^{nd}$ invention of the present invention (corresponding to claim 2) is the vital sign box according to $1^{st}$ invention, further comprising a base that is rotatable, can be fixed at a predetermined angle, and houses the camera at the time of detachment.

The $3^{rd}$ invention of the present invention (corresponding to claim 3) is the vital sign box according to $1^{st}$ invention, wherein the camera is rotatable, and can be fixed at a predetermined angle.

The $4^{th}$ invention of the present invention (corresponding to claim 4) is the vital sign box according to $1^{st}$ invention, wherein the camera is detachable.

The $5^{th}$ invention of the present invention (corresponding to claim 5) is the vital sign box according to $4^{th}$ invention, wherein the camera is a fixed focus type camera.

The $6^{th}$ invention of the present invention (corresponding to claim 6) is the vital sign box according to $5^{th}$ invention, wherein the camera comprises:
  a string-like or rod-like body that indicates whether distance between the imaging object and a predetermined section of the camera becomes predetermined length, and is attached at the predetermined section of the camera, and has predetermined length;
  instruction receiving means of receiving an imaging instruction of the imaging object; and
  imaging means of taking a picture of the imaging object when the instruction receiving means receives the imaging instruction.

The $7^{th}$ invention of the present invention (corresponding to claim 7) is the vital sign box according to $5^{th}$ invention, wherein the camera comprises:
  range-finding means of detecting distance between the imaging object and the predetermined section of the camera;
  comparing means of comparing distance, detected by the range-finding means, with predetermined length;
  result output means of outputting a comparison result, obtained by the comparing means, by a sound and/or an image;
  instruction receiving means of receiving an imaging instruction of the imaging object; and
  imaging means of taking a picture of the imaging object when the instruction receiving means receives the imaging instruction.

The $8^{th}$ invention of the present invention (corresponding to claim 8) is the vital sign box according to $5^{th}$ invention wherein the camera comprises:
  range-finding means of detecting distance between the imaging object and a predetermined section of the camera;
  comparing means of comparing distance, detected by the range-finding means, with predetermined length; and
  imaging means of taking a picture of the imaging object when distance, detected by the range-finding means, substantially coincides with the predetermined length.

The $9^{th}$ invention of the present invention (corresponding to claim 9) is the vital sign box according to $1^{st}$ invention, wherein the camera has a lighting section emitting light to the object.

The $10^{th}$ invention of the present invention (corresponding to claim 10) is the vital sign box according to $1^{st}$ invention, further comprising a display displaying an object whose image is taken by the camera.

The $11^{th}$ invention of the present invention (corresponding to claim 11) is an vital sign box comprising:
  a plurality of vital sensors that measures predetermined biological, chemical, or physical conditions of a living body, and transmits measurements, obtained by the measurement, with using an electric wave;
  a reception sensor receiving measurements from the plurality of vital sensors;
  memory recording measurements received by the reception sensor; and
  a housing containing the plurality of vital sensors, the reception sensor, and the memory.

The $12^{th}$ invention of the present invention (corresponding to claim 12) is the vital sign box according to $11^{th}$ invention, wherein the electric wave is an infrared ray having a predetermined wavelength.

The $13^{th}$ invention of the present invention (corresponding to claim 13) is an vital sign box comprising: a plurality of vital sensors measuring predetermined biological, chemical, or physical conditions of a living body; and a housing with a lid that contains at least the plurality of vital sensors, wherein the lid has a shank that becomes a substantially shaft when the lid is opened and closed;
  wherein the shank is provided in the housing so that a main body of the housing has a front section and a rear section to the shank; and
  wherein the lid can be fixed in a status that the lid stands to a bottom section of the vital sign box with using the shank when the vital sign box is used.

The 14$^{th}$ invention of the present invention (corresponding to claim 14) is the vital sign box according to 13$^{th}$ invention further comprising a display that is provided and fixed inside the lid of the housing, and displays measurements measured by the vital sensors.

The 15$^{th}$ invention of the present invention (corresponding to claim 15) is an vital sign box comprising: a plurality of vital sensors measuring predetermined biological, chemical, or physical conditions of a living body; a display displaying measurements measured by the vital sensors; and a housing with a lid that contains the plurality of vital sensors and the display.

The 16$^{th}$ invention of the present invention (corresponding to claim 16) is the vital sign box according to 15$^{th}$ invention, wherein the display is movable;

wherein the housing has a display fixing section to fix the display; and wherein the display lies in a bottom section of the housing at the time of non-use and can be fixed in a status that the display stands to the bottom section of the housing with using the display fixing section at the time of use.

The 17$^{th}$ invention of the present invention (corresponding to claim 17) is an vital sign box comprising:

a plurality of vital sensors measuring predetermined biological, chemical, or physical conditions of a living body;

memory recording measurements measured by the vital sensors;

a display that displays measurements measured by the vital sensors, and/or a plurality of measurements recorded in the memory, and determines a display range and/or a display scale with each of the measurements, which are displayed, being as a reference; and a housing that contains the plurality of vital sensors, the memory, and the display.

The 18$^{th}$ invention of the present invention (corresponding to claim 18) is the vital sign box according to 17$^{th}$ invention wherein each of the measurement to be a reference is a newest measurement and the item to be determined is a display range.

The 19$^{th}$ invention of the present invention (corresponding to claim 19) is the vital sign box according to 17$^{th}$ invention, wherein, when at least one of the plurality of vital sensors measures upper and lower limits of the predetermined condition substantially at the same time, the display simultaneously displays the measurements, which are measured and are upper and lower limits, and/or a plurality of measurements, which are recorded in the memory, with classifying the measurements into the upper limits and the lower limits whose display areas are divided separately.

The 20$^{th}$ invention of the present invention (corresponding to claim 20) is an vital sign box comprising:

a plurality of vital sensors measuring predetermined biological, chemical, or physical conditions of a living body;

a speaker outputting measurements, measured by the vital sensors, by sound; and a housing containing the plurality of vital sensors, and the speaker.

The 21$^{st}$ invention of the present invention (corresponding to claim 21) is a vital sign box comprising:

a plurality of vital sensors measuring predetermined biological, chemical, or physical conditions of a living body;

an camera taking a picture of a predetermined object;

memory recording measurements measured by the vital sensors and/or objects whose images are taken by the camera;

a communication terminal of transmitting all or part of measurements measured by the vital sensors, an object whose image is taken by the camera, measurements recorded in the memory, and objects recorded in the memory; and a housing containing the plurality of vital sensors, the camera, the memory, and the communication terminal.

The 22$^{nd}$ invention of the present invention (corresponding to claim 22) is the vital sign box according to 21$^{st}$ invention, wherein the communication terminal receives predetermined information from a communication partner, and wherein the vital sign box comprises a display that is contained in the housing, and not only displays all or part of measurements measured by the vital sensors, an object whose image is taken by the camera, measurements recorded in the memory, and objects recorded in the memory, but also displays information from the communication partner inputted by the communication terminal.

The 23$^{rd}$ invention of the present invention (corresponding to claim 23) is the vital sign box according to 22$^{nd}$ invention, wherein one of information from the communication partner, which is displayed in the display, is arrowhead information for specifying a predetermined position of the display, and the arrowhead is displayed in the display with all or part of measurements measured by the vital sensors, an object whose image is taken by the camera, measurements recorded in the memory, and objects recorded in the memory that are displayed in the display.

The 24$^{th}$ invention of the present invention (corresponding to claim 24) is the vital sign box according to 23$^{rd}$ invention wherein the arrowhead information is coordinate information of the position when the arrowhead is let to be displayed in the display, and the display has shape information of the arrowhead to be displayed and displays the arrowhead on the basis of the coordinate information from the communication partner.

The 25$^{th}$ invention of the present invention (corresponding to claim 25) is an vital sign box comprising:

a plurality of vital sensors measuring predetermined biological, chemical, or physical conditions of a living body;

a power supply section that is provided so as not to contact with the vital sensors and supplies electric power from the outside of the vital sign box to all or part of the plurality of vital sensors with using an electromagnetic wave by electromagnetic induction; and a housing containing the plurality of vital sensors, and the power supply section.

The 26$^{th}$ invention of the present invention (corresponding to claim 26) is an vital sign box comprising:

a plurality of vital sensors measuring predetermined biological, chemical, or physical conditions of a living body;

a microphone inputting sound;

a communication terminal transmitting sound inputted by the microphone; and a housing containing the plurality of vital sensors, the microphone, and the communication terminal.

The 27th invention of the present invention (corresponding to claim 27) is an vital sign box comprising:
- a display displaying inquiry items to a user;
- an inquiry result input section of inputting an inquiry result to inquiries in the display;
- a communication terminal transmitting the inquiry result inputted by the inquiry result input section; and
- a housing containing the display, the inquiry result input section, and the communication terminal.

The 28th invention of the present invention (corresponding to claim 28) is the vital sign box according to 27th invention, wherein the communication terminal is a device inputting predetermined information from a communication partner to whom the inquiry result is sent and the display also displays information from the communication partner that is inputted by the communication terminal.

The 29th invention of the present invention (corresponding to claim 29) is the vital sign box according to 27th invention wherein the communication terminal is a device inputting predetermined information from a communication partner to whom the inquiry result is sent, and the vital sign box further comprises a speaker that is contained in the housing and outputs information from the communication partner, which is inputted by the communication terminal, with using sound.

The 30th invention of the present invention (corresponding to claim 30) is an vital sign box comprising:
- a speaker outputting inquiry items to a user by sound;
- an inquiry result input section inputting an inquiry result to inquiries from the speaker;
- a communication terminal transmitting the inquiry result inputted by the inquiry result input section; and
- a housing containing the speaker, the inquiry result input section, and the communication terminal.

The 31st invention of the present invention (corresponding to claim 31) is the vital sign box according to 30th invention wherein the communication terminal is a device inputting predetermined information from a communication partner to whom the inquiry result is sent, and the speaker also outputs information from the communication partner, which is inputted by the communication terminal, with using sound.

The 32nd invention of the present invention (corresponding to claim 32) is the vital sign box according to 30th invention, wherein the communication terminal is a device inputting predetermined information from a communication partner to whom the inquiry result is sent, and the vital sign box further comprises the display that is contained in the housing and displays information from the communication partner that is inputted by the communication terminal.

The 33rd invention of the present invention (corresponding to claim 33) is the vital sign box according to any one of $1^{st}$, $11^{th}$, $13^{th}$, $15^{th}$, $17^{th}$, $20^{th}$, $21^{st}$, $25^{th}$, $26^{th}$, $27^{th}$, and $30^{th}$ inventions, wherein the housing has a lid; wherein a clamp for closing the lid and fixing the lid to the main body of the housing is provided in each of a main body of the housing and the lid; and wherein a handle is provided in the main body of the housing.

The 34th invention of the present invention (corresponding to claim 34) is the vital sign box according to any one of $1^{st}$ to $32^{nd}$ inventions, further comprising a password input section of inputting a password of a user, wherein measurements measured by the vital sensors, and/or an object whose image is taken by the camera are managed with being associated with a password inputted in the password input unit.

The 35th invention of the present invention (corresponding to claim 35) is the vital sign box according to any one of $1^{st}$ to $32^{nd}$ inventions, wherein all or part of the plurality of vital sensors and/or the camera each have an electric power storage section storing electric power.

The 36th invention of the present invention (corresponding to claim 36) is the vital sign box according to any one of $1^{st}$ to $32^{nd}$ inventions, further comprising a display displaying usage of an vital sign box.

The 37th invention of the present invention (corresponding to claim 37) is the vital sign box according to 36th invention, wherein all or part of the usage is displayed by an image.

The 38th invention of the present invention (corresponding to claim 38) is the vital sign box according to 37th invention, wherein the image is a graphic image of measurements measured by a vital sensor.

The 39th invention of the present invention (corresponding to claim 39) is the vital sign box according to 36th invention, wherein the display is a touch panel type liquid crystal display and changes display contents by a predetermined portion of the liquid crystal display being touched by a user.

The 40th invention of the present invention (corresponding to claim 40) is the vital sign box according to any one of $1^{st}$ to $32^{nd}$ inventions, further comprising a speaker outputting usage of an vital sign box by sound.

The 41st invention of the present invention (corresponding to claim 41) is the vital sign box according to 40th invention, further comprising: a display displaying usage of an vital sign box; and a change instruction input section of inputting an instruction for changing an output of the usage from an output where sound from the speaker is used to an output where display in the display is used.

The 42nd invention of the present invention (corresponding to claim 42) is the vital sign box according to any one of $10^{th}$, $14^{th}$, $15^{th}$, $17^{th}$, $22^{nd}$, $27^{th}$, $32^{nd}$, $36^{th}$, and $41^{st}$ inventions, wherein the display is a touch panel type display having a software keyboard function.

The 43rd invention of the present invention (corresponding to claim 43) is the vital sign box according to any one of $10^{th}$, $14^{th}$, $15^{th}$, $17^{th}$, $22^{nd}$, $27^{th}$, $32^{nd}$, $36^{th}$, and $41^{st}$ inventions, wherein at least part of the housing consists of metallic material, and the vital sign box comprises a connecting section that consists of metallic material and connects a heating section, generating heat in connection with image display to the display, with a metallic material section of the housing.

The 44th invention of the present invention (corresponding to claim 44) is the vital sign box according to any one of $20^{th}$, $30^{th}$, and $40^{th}$ inventions, wherein at least part of the housing consists of metallic material, and the vital sign box comprises a connecting section that consists of metallic material and connects a heating section, generating heat in connection with a sound output from the speaker, with a metallic material section of the housing.

The 45th invention of the present invention (corresponding to claim 45) is the vital sign box according to any one of $21^{st}$, $26^{th}$, $27^{th}$, and $30^{th}$ inventions, wherein at least part of the housing consists of metallic material, and the vital sign box comprises a connecting section that consists of metallic material and connects a heating section, generating heat in connection with information communication in the communication terminal, with a metallic material section of the housing.

The 46th invention of the present invention (corresponding to claim 46) is a medium that bears a program and/or data for letting a computer execute all or part of functions of the vital sign box according to any one of 36th to 41st inventions, the medium with which a computer can perform processing.

The 47th invention of the present invention (corresponding to claim 47) is an information aggregation, wherein the information aggregation is a program and/or data for letting a computer execute all or part of functions of the vital sign box according to any one of 36th to 41st inventions.

BRIEF DESCRIPTION OF THE DRAWINGS

FIG. 7 is a diagram showing a display screen for letting a user of the vital sign box according to the first embodiment of the present invention input the user's name;

FIG. 8 is a diagram showing a display screen for letting a user of the vital sign box according to the first embodiment of the present invention input a password;

FIG. 27 is a drawing showing a display screen for letting a user of the vital sign box according to the first embodiment of the present invention input a name and a telephone number of a communication partner;

FIG. 28 is a drawing showing a display screen for letting a user of the vital sign box according to the first embodiment of the present invention input a telephone number of a communication partner;

| | Description of Symbols |
|---|---|
| 1 | Electrocardiograph |
| 1a | Contact section for a left arm |
| 1b | Contact section for a right arm |
| 2 | Blood Pressure Monitor |
| 3 | Earhole clinical thermometer |
| 4 | Blood glucose meter |
| 4a | Blood-collecting needle |
| 4b | Sensor chip |
| 4c | Connection jack |
| 5 | Electronic camera |
| 6 | Base |
| 6a | Connecting section |
| 7 | LED |
| 8 | Reception sensor |
| 9 | Memory |
| 10 | Display |
| 11 | Speaker |
| 12 | Microphone |
| 13 | Communication terminal |
| 14 | Housing |
| 15 | Lid |

| | -continued |
|---|---|
| | Description of Symbols |
| 16 | Shank |
| 17 | Power supply section |

DESCRIPTION OF THE PREFERRED EMBODIMENTS

Hereinafter, embodiments of the present invention will be described with reference to drawings.

Embodiment 1

First of all, the configuration of an vital sign box of a first embodiment of the present invention will be described.

Figure 1:
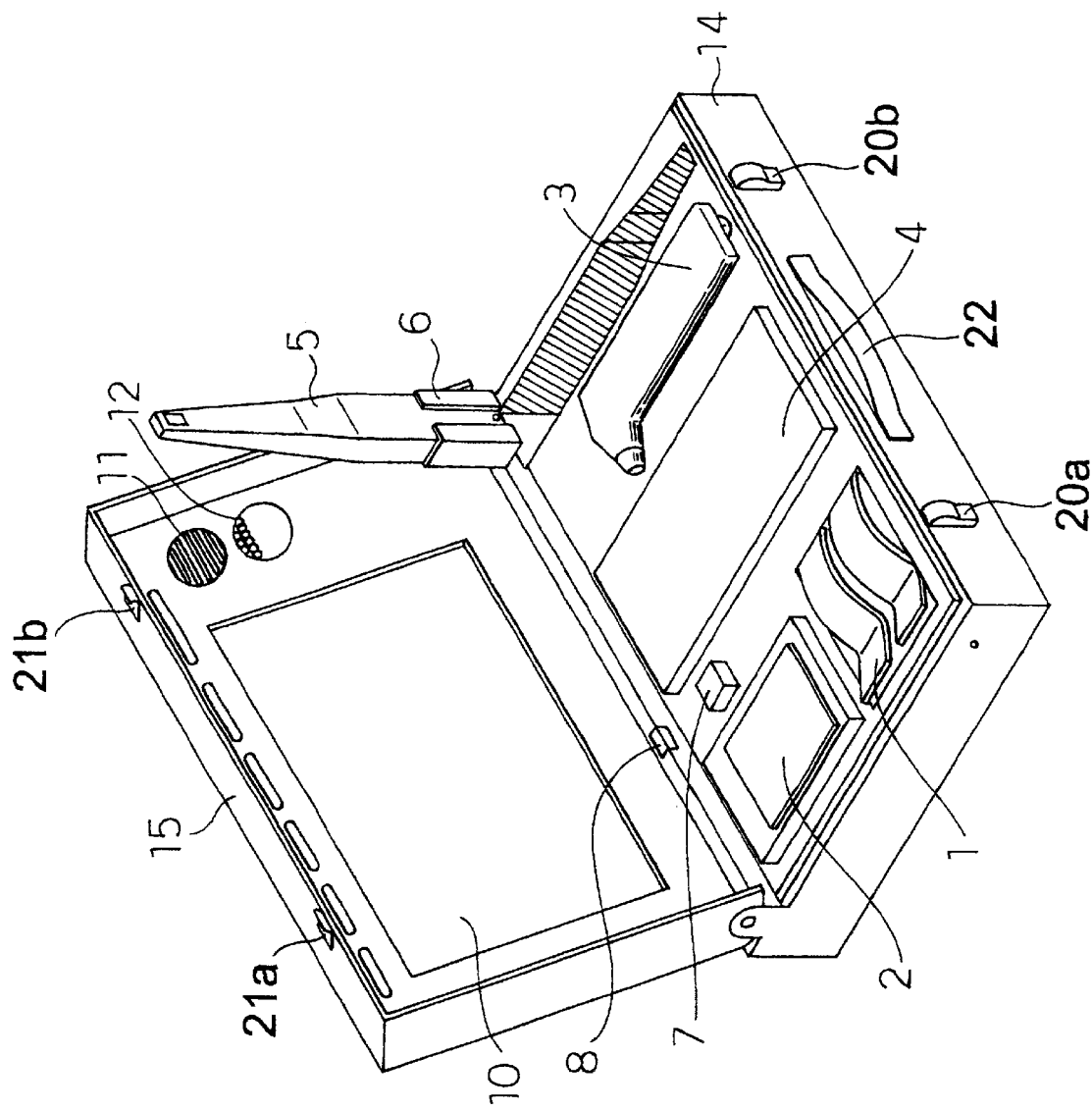
FIG. 1 is a perspective view of an vital sign box when a lid of the vital sign box according to a first embodiment of the present invention is opened.
Figure 2:
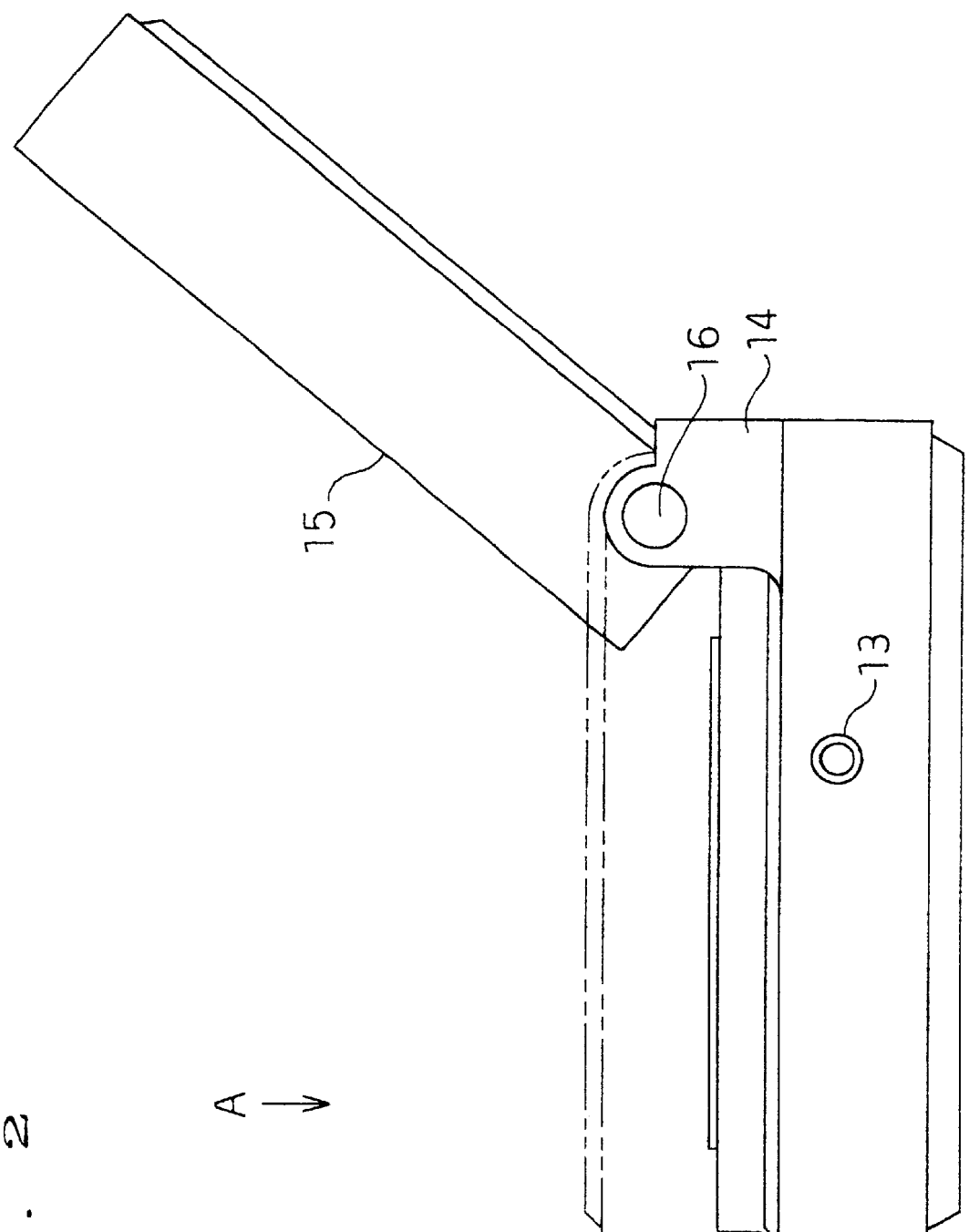
FIG. 2 is a side view of the vital sign box when the lid of the vital sign box according to the first embodiment of the present invention is opened.
Figure 3:
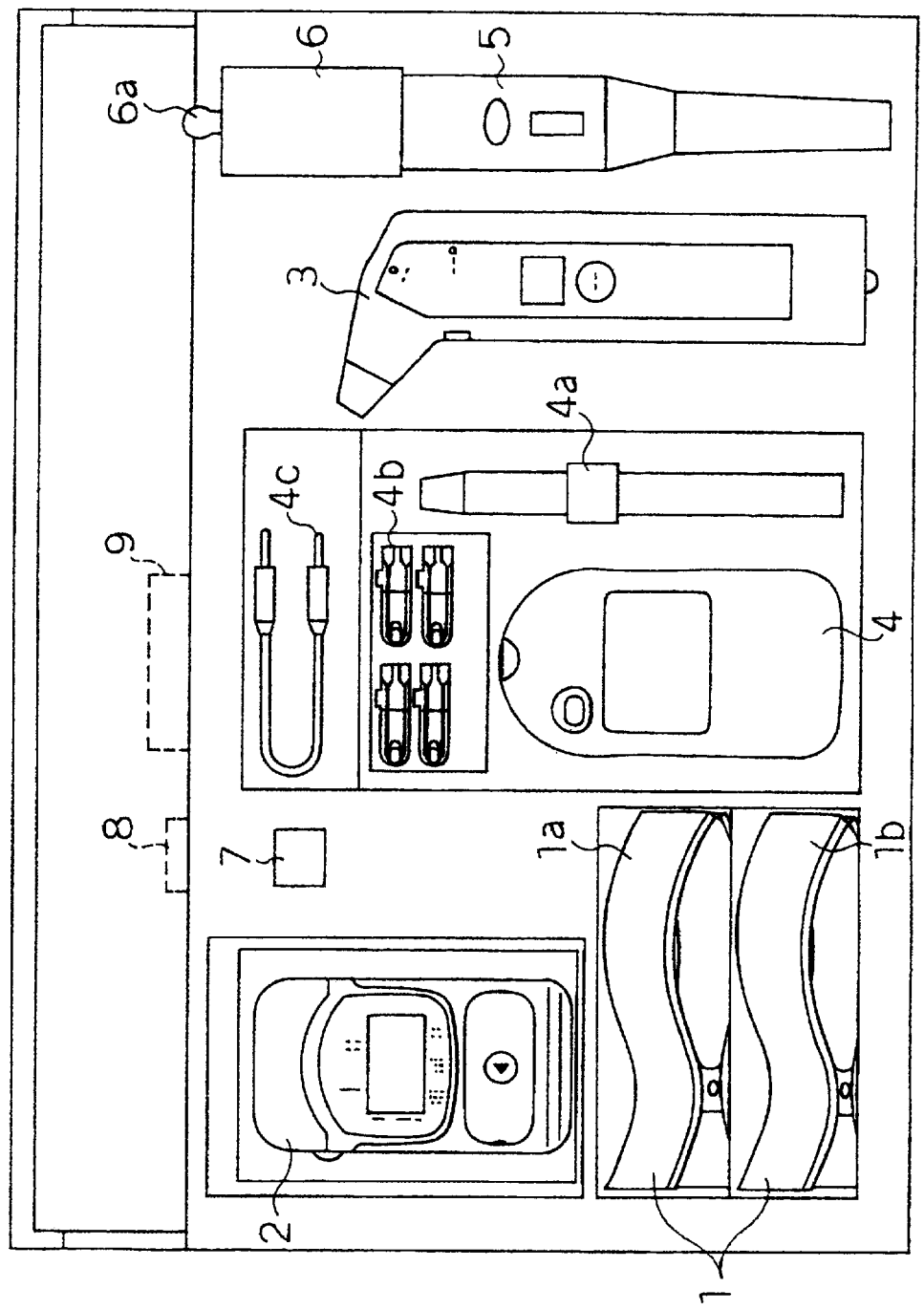
FIG. 3 is a top view of the vital sign box when viewing the vital sign box, the lid of which is opened, according to the first embodiment of the present invention from an arrow A in FIG. 2.
Figure 4:
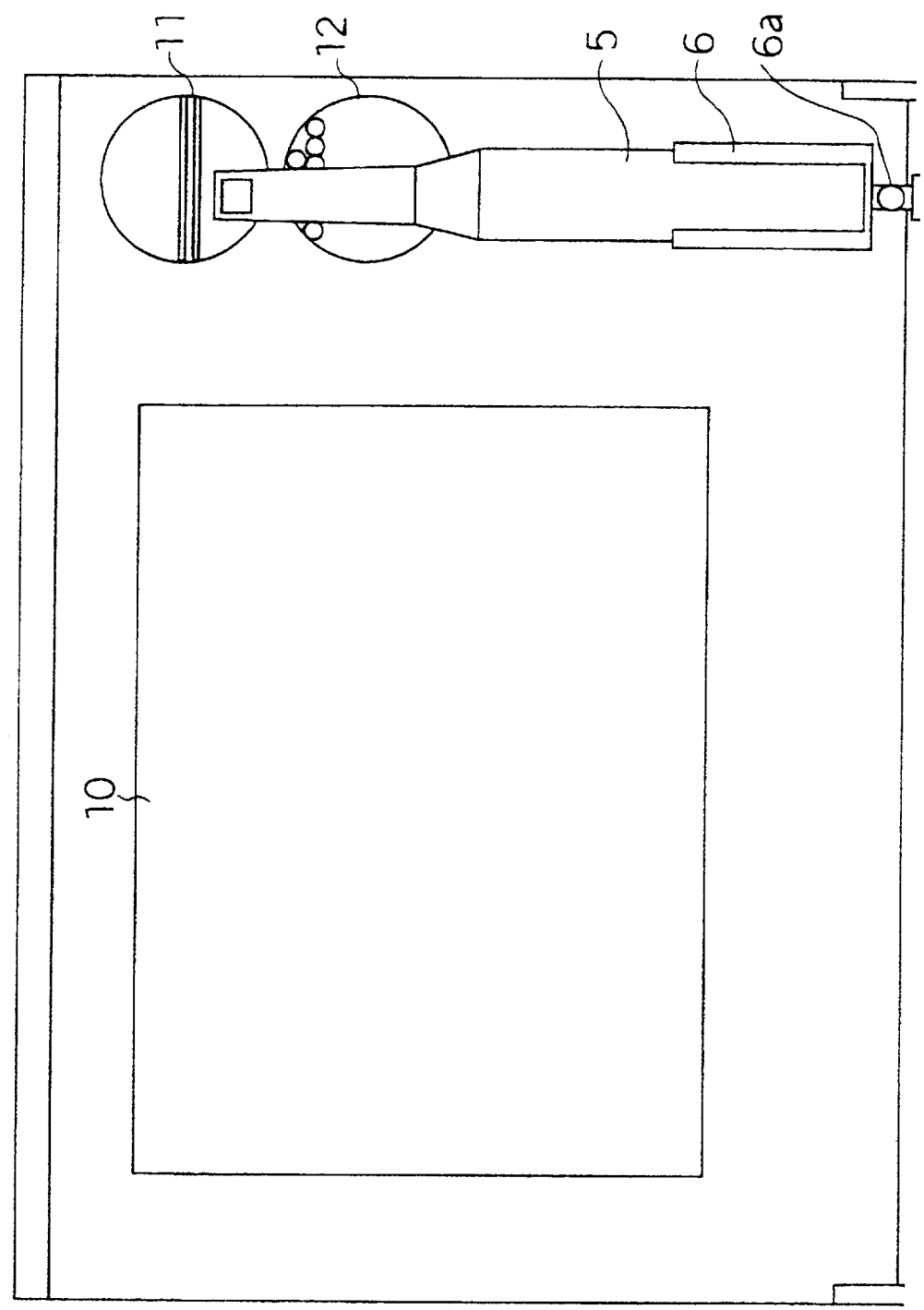
FIG. 4 is a front view showing the inside of the lid of the vital sign box when the lid of the vital sign box according to the first embodiment of the present invention is opened substantially vertically to a bottom face of the vital sign box and an camera provided in the vital sign box is also stood substantially vertically to the bottom face of the vital sign box.

FIG. 1 is a perspective view of the vital sign box when a lid of the vital sign box according to the first embodiment of the present invention is opened. FIG. 2 is a side view of the vital sign box when the lid of the vital sign box according to the first embodiment of the present invention is opened. FIG. 3 is a top view of the vital sign box when viewing the vital sign box, the lid of which is opened, according to the first embodiment of the present invention from an arrow A in FIG. 2. FIG. 4 is a front view showing the inside of the lid of the vital sign box when the lid of the vital sign box according to the first embodiment of the present invention is opened substantially vertically to a bottom face of the vital sign box and an camera provided in the vital sign box is also stood substantially vertically to the bottom face of the vital sign box.

As shown in FIGS. 1 to 4, the vital sign box according to the first embodiment of the present invention consists of an electrocardiograph 1, a blood pressure monitor 2, an earhole clinical thermometer 3, a blood glucose meter 4, an camera 5, a base 6, an LED 7, a reception sensor 8, memory 9, a display 10, a speaker 11, a microphone 12, a communication terminal 13, and a housing 14.

The electrocardiograph 1 is means of measuring electrocardio, and, as shown in FIG. 3, consists of a clip-like contact section for a left arm 1a and a contact section for a right arm 1b that contact to left and right arms of a human body respectively. Those contact section for a left arm 1a and contact section for a right arm 1b are connected to a main body of the vital sign box with connection cords, and are means of transmitting measurements to the LED 7 through the connection cords with using electrical signals. In addition, inside the contact section for a left arm 1a and contact section for a right arm 1b, a circuit for measuring electrocardio is built in, and the circuit is utilized in electrocardio measurement.

The blood pressure monitor 2 is means of measuring blood pressure and a pulse rate, and is a handy type meter. Furthermore, the blood pressure monitor 2 is means that is not connected to the main body of the vital sign box with a connection cord but transmits a measurement to the reception sensor 8 with using an infrared ray having a predetermined wavelength.

The earhole clinical thermometer 3 is means of measuring body temperature, and is a handy type meter similarly to the blood pressure monitor 2. Furthermore, the earhole clinical thermometer 3 is means that is not connected to the main body of the vital sign box with a connection cord but transmits a measurement to the reception sensor 8 with using an infrared ray having a predetermined wavelength.

The blood glucose meter 4 is means of measuring sugar density in blood, and has a blood-collecting needle 4a, a sensor chip 4b, and a connection jack 4c. Furthermore, when being housed in the housing 14, the blood glucose meter 4, blood-collecting needle 4a, sensor chip 4b, and connection jack 4c are housed separately. Moreover, the blood glucose meter 4 is a handy type meter, and the sensor chip 4b is mounted and used when a blood glucose level is measured. The blood glucose meter 4 measures a blood glucose level of the blood collected by the blood-collecting needle 4a with utilizing the sensor chip 4b. In addition, when measured data is transmitted to the main body of the vital sign box, the blood glucose meter 4 is connected to the connection jack 4c, and furthermore, the connection jack 4c is connected to the main body of the vital sign box. The measured data is transmitted from the blood glucose meter 4 to the LED 7 in the main body of the vital sign box through the connection jack 4c with using an electrical signal. The blood-collecting needle 4a is means of gathering blood from a human body, the sensor chip 4b is means of measuring a blood glucose level of the blood collected by the blood-collecting needle 4a, and the connection jack 4c connects the blood glucose meter 4 to the main body of the vital sign box.

In addition, the electrocardiograph 1, blood pressure monitor 2, earhole clinical thermometer 3, and blood glucose meter 4 are used an example of vital sensors according to the vital sign box of the present invention.

In addition, the electrocardiograph 1, blood pressure monitor 2, earhole clinical thermometer 3, and blood glucose meter 4 are used as an example of vital sensors according to the vital sign box of the present invention, the vital sensors which are described in claims 1, 11, 13, 15, 17, 20, 21, 25 and 26.

The camera 5 is means of taking a picture of a predetermined object, has a lighting section lighting the object, and is detachable from the base 6.

The base 6 has a connecting section 6a, is connected to the housing 14 through the connecting section 6a, is rotatable with the connecting section 6a as a fulcrum, and not only can be fixed at a predetermined angle, but also is means of containing the camera 5.

The LED 7 is means of converting each measurement, transmitted with using electrical signals from the electrocardiograph 1 and blood glucose meter 4, into an infrared ray having a predetermined wavelength and transmitting each measurement to the reception sensor 8.

The reception sensor 8 is means of receiving each infrared ray having a predetermined wavelength from the blood pressure monitor 2, earhole clinical thermometer 3, and LED 7.

The memory 9 is installed with being embedded in the housing 14, and is means of not only recording each measurement on the basis of the infrared ray received by the reception sensor 8, but also recording an image of an object recorded by the camera 5.

The display 10 is means of displaying each measurement measured by the electrocardiograph 1, blood pressure monitor 2, earhole clinical thermometer 3, and blood glucose meter 4, an object, a picture of which is taken by the camera 5, and usage of the vital sign box according to the first embodiment of the present invention. The display 10 is a touch panel type liquid crystal display, and hence changes display contents when each of predetermined portions is touched.

The speaker 11 is means of outputting each measurement measured by the electrocardiograph 1, blood pressure monitor 2, earhole clinical thermometer 3, and blood glucose meter 4 or usage of the vital sign box according to the first embodiment of the present invention with using sound.

Microphone 12 is means of collecting sound of voice and the like of a user of the vital sign box according to the first embodiment of the present invention.

The communication terminal 13 is means of transmitting each measurement measured by the electrocardiograph 1, blood pressure monitor 2, earhole clinical thermometer 3, and blood glucose meter 4, and an object recorded by the camera 5 to a communications partner with using a communication line.

The housing 14 is means of having the lid 15 and containing all of the above-described sections from the electrocardiograph 1 to the terminal 13. The lid 15 has the shank 16 that substantially becomes a shaft when the lid 15 is opened and closed, and not only is installed in the housing 14 through the shank 16, but also can be fixed at a predetermined angle of gradient to the housing 14. In addition, it is assumed that the electrocardiograph 1, blood pressure monitor 2, earhole clinical thermometer 3, blood glucose meter 4, camera 5, base 6, LED 7, reception sensor 8, and memory 9 are contained in a main body of the housing 14, that the display 10, speaker 11, and microphone 12 are provided inside the lid 15, and that the communication terminal 13 is provided outside the main body of the housing 14.

In addition, as show in FIG. 1, in the housing 14 and lid 15 each, clamps 20a, 20b, 21a, and 21b are attached for closing the lid 15 and fixing the lid 15 to the housing 14. Furthermore, a handle 22 for easily carrying the vital sign box of the first embodiment when the lid 15 is closed and is fixed to the housing 14 is provided in the housing 14.

Moreover, although being not shown in FIGS. 1 to 4, a program recording medium that stores a program to let the display 10 and speaker 11 output the usage of the vital sign box is built in the vital sign box according to the first embodiment of the present invention.

In addition, it is made that the vital sign box of the first embodiment of the present invention can receive data from a scale that is different from the vital sign box and can transmit a measurement to the vital sign box with using an infrared ray having a predetermined wavelength. It is made that the LED 7 receives data from the scale at that time.

Furthermore, it is assumed that the vital sign box according to the first embodiment of the present invention is connected to a personal computer in a hospital through the communication terminal 13.

Moreover, although having been explained once, FIG. 3 will be explained again. FIG. 3 is a top view showing the main body of the housing 14 when the electrocardiograph 1, blood pressure monitor 2, earhole clinical thermometer 3, blood glucose meter 4, camera 5, base 6, LED 7, reception sensor 8, and memory 9 are contained in the main body of the housing 14 and the lid 15 is opened.

Next, the operation of the vital sign box according to the first embodiment of the present invention will be described.

First of all, a user switches on the vital sign box, and opens the lid 15 of the housing 14 as shown in FIGS. 1 and 2.

When the vital sign box is turned on, the display 10 provided inside the lid 15 begins displaying the usage of the vital sign box on the basis of the program stored in the program recording medium. In addition, similarly, on the basis of the program stored in the program recording medium, the speaker 11 begins outputting the usage of the vital sign box by sound.

Figure 5:
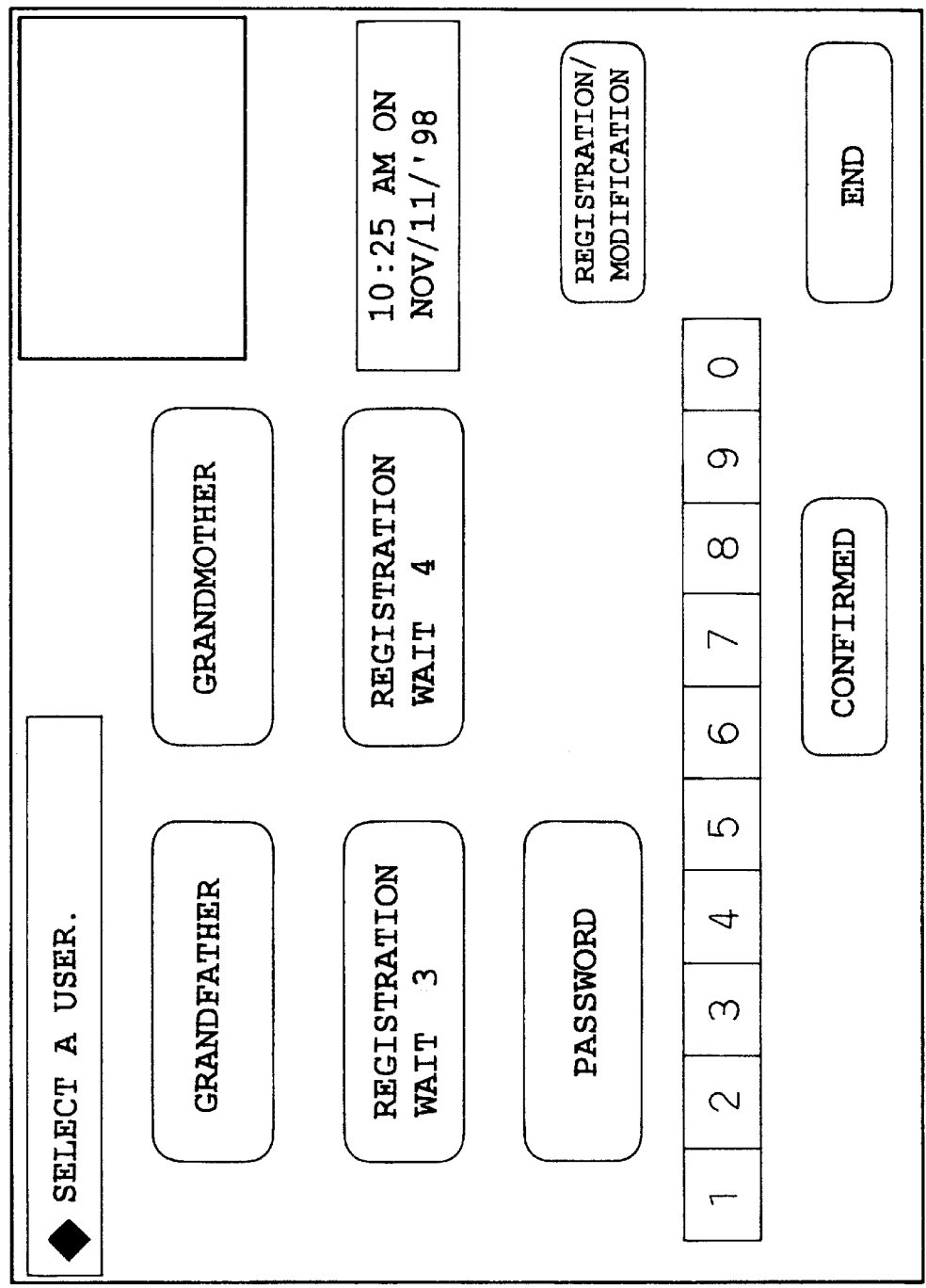
FIG. 5 is a drawing showing a display screen on which the vital sign box according to the first embodiment of the present invention lets a user input the user's name and password in order to specify the user.

FIG. 5 shows display contents that are first displayed in the display 10 after the vital sign box was switched on. FIG. 5 is a drawing showing a display screen on which the vital sign box lets a user input the user's name and password in order to specify the user. By the way, the reason why a user is specified is for the vial sign box to associate a measurement measured by each vital sensor and an image a picture of which is taken by the camera 5 with each user, and to manage the measurement and image every user. In addition, in connection to it, the reason is also to protect the privacy of the measurement and the shot image of each user is protected. Furthermore, when the display 10 displays contents shown in FIG. 5, the user touches a portion of any one of "Grandfather," "Grandmother," "Registration wait 3," and "Registration wait 4" in the display 10. By the way, the display of the "Grandfather" and "Grandmother" means that names and passwords of the "Grandfather" and "Grandmother" have been already registered. In addition, the display of the "Registration wait 3" and "Registration wait 4" means that names and passwords of users are not registered.

Figure 9:
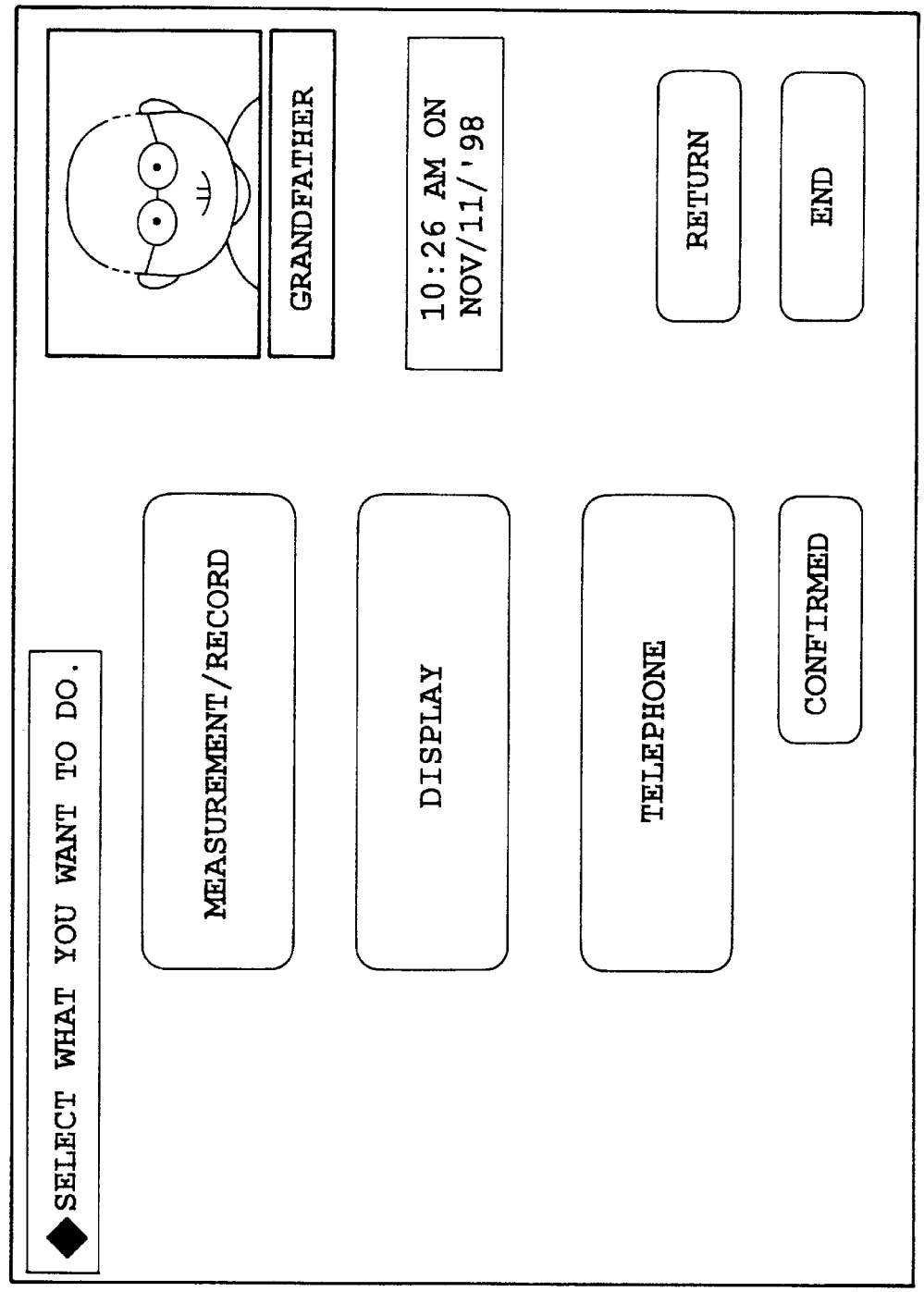
FIG. 9 is a diagram showing a display screen on which the vital sign box according to the first embodiment of the present invention lets a user select any one of the use of each vital sensor or an camera 5, display of data stored in memory 9, or communication with a hospital.

Then, if the user is the "Grandfather" or "Grandmother" and the user's name and password have been registered beforehand, the user touches an adequate portion, furthermore touches a "password" to input the user's password, and goes to the next step shown in FIG. 9. On the other hand, if the user is not the "Grandfather" or "Grandmother" but the user's name and password are not registered, the user touches a portion of any one of the "Registration wait 3" and "Registration wait 4." The user touches the "Registration wait 3" or "Registration wait 4" so as to use the vital sign box many times later and to let the vital sign box manage measurements measured by each vital sensor and/or images taken by the camera 5. When the user touches the "Registration wait 3" or "Registration wait 4," the display 10 displays the contents shown in FIG. 7, and lets the user register the user's name with letting the user utilize the touch panel. If the user touches a "Confirm" portion after registration, the display 10 displays the contents shown in FIG. 8 to let the user register, for example, four character password with letting the user use the touch panel again. In this manner, if the user is made to register the user's name and password, the name and password are managed by the vital sign box after that with being associated with the "Registration wait 3" or "Registration wait 4" that was touched before the registration of the name and password. In addition, if the name and password are registered, the display 10 displays the contents shown in FIG. 9.

If the user operates according to the display of the display 10 as described above, the display 10 displays the contents shown in FIG. 9.

Figure 6:
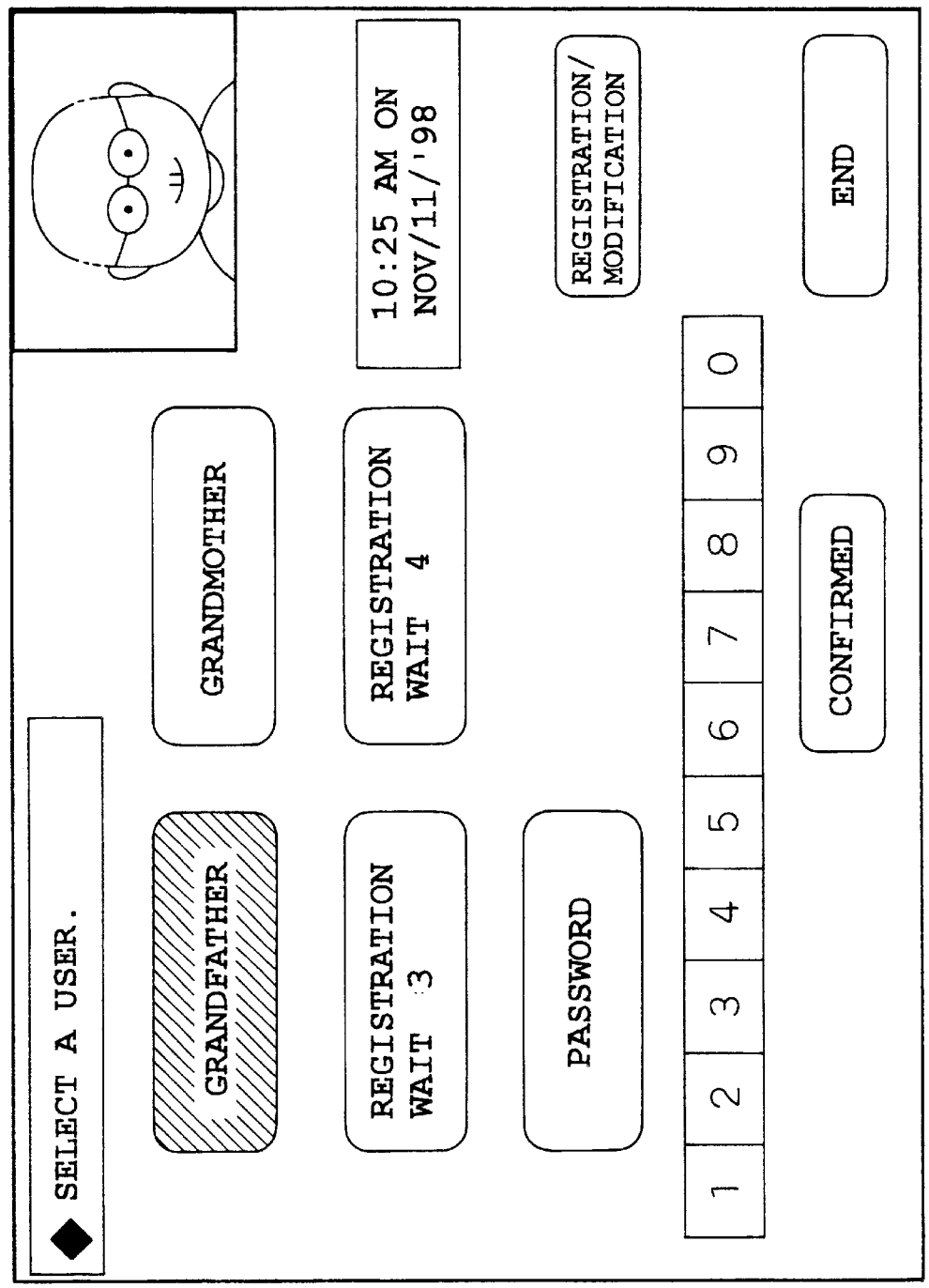
FIG. 6 is an explanatory diagram for explaining that a display 10 of the vital sign box according to the first embodiment of the present invention displays the contents shown in FIG. 5, and if a "Grandfather" portion in the display 10 is touched by a user, the "Grandfather" portion is displayed with blinking.

In addition, for the convenience of explanation, it is assumed that the user of the vital sign box is a "Grandfather." Therefore, in this case, when the display 10 displays the contents shown in FIG. 5, the user touches the "Grandfather" portion in the display 10. When the "Grandfather" portion is touched in this manner, the display 10 displays the "Grandfather" portion with blinking as shown in FIG. 6. In addition, in FIG. 6, it is assumed that slanted lines of the portion displaying the "Grandfather" portion denote that the portion displaying the "Grandfather" blinks. In addition, it is assumed for the convenience of the following explanation as described above that the user of the vital sign box is the "Grandfather." Nevertheless, it is assumed that, even if the user is not the "Grandfather" but the user touches the "Grandmother," "Registration wait 3," or "Registration wait 4" when the display 10 displays the contents shown in FIG. 5, the display 10 displays and blinking the touched portion. Furthermore, also in the following description, it is assumed that, if a predetermined portion of the display 10 is touched by a user, the display 10 displays and blinking the touched portion.

Moreover, although the usage of the vital sign box only by the display of the display 10 is explained in the above description, it is made that the usage is explained simultaneously with using sound from the speaker 11. Similarly, also in the following explanation, it is assumed that the usage of the vital sign box is explained not only in the display of the display 10, but also by a sound output from the speaker 11.

In addition, in the above description, the display 10 corresponds to a password input section of the present invention according to claim 34.

Furthermore, as explained when the configuration of vital sign box according to the first embodiment of the present invention is described, the display 10 is a touch panel type liquid crystal display. Hence, for a user, the display 10 is convenient because it is not necessary to use a ten-key pad or a mouse when the user changes the display contents of the display 10.

By the way, FIG. 9 is a drawing showing a display screen for letting a user select any one of using each vital sensor or the camera 5 of the vital sign box, letting the display 10 display the data that is stored as measurements and pictures in the memory 9, and communicating with a personal computer in a hospital that is connected to the vital sign box.

Figure 10:
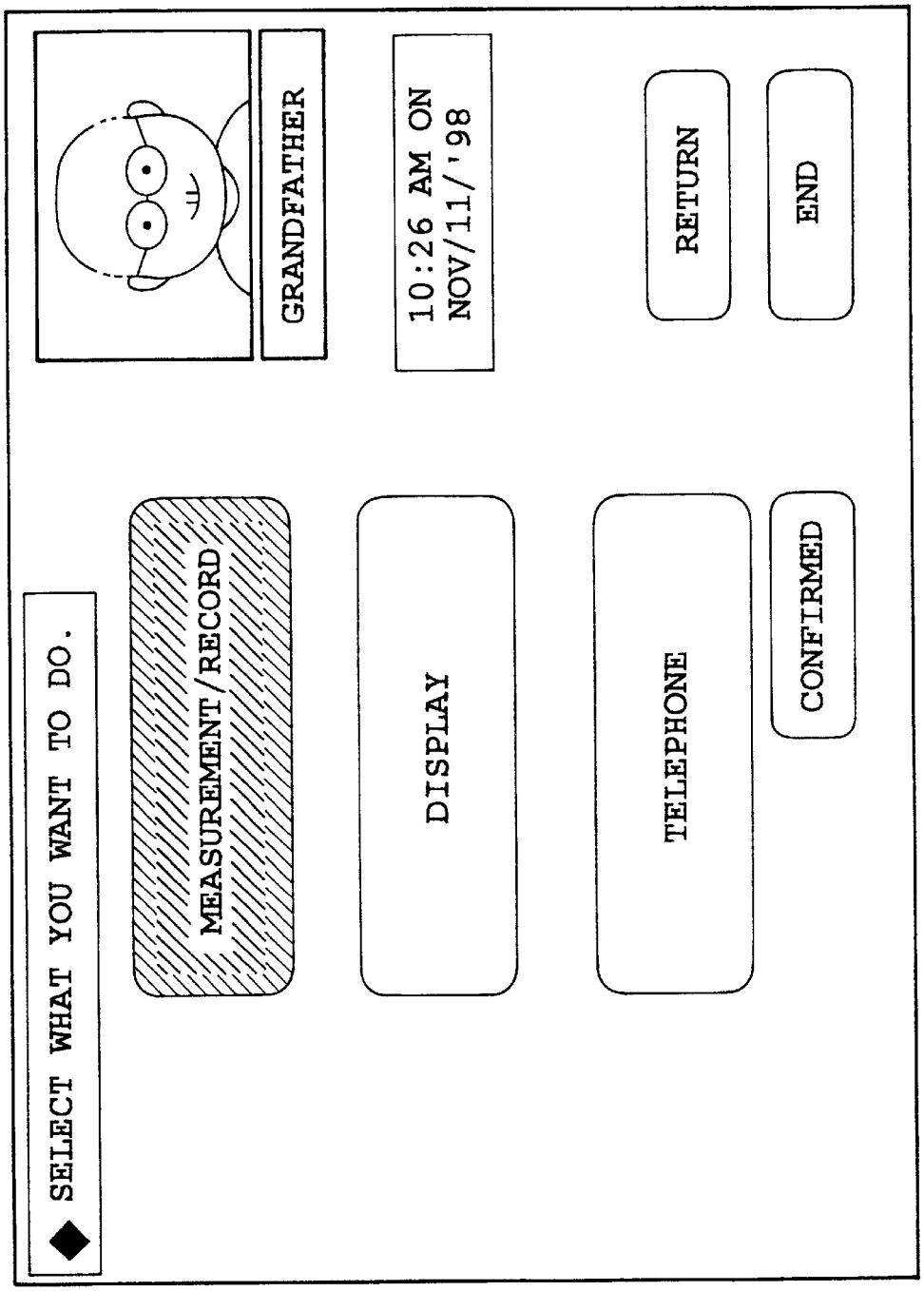
FIG. 10 is an explanatory diagram for explaining that a display 10 of the vital sign box according to the first embodiment of the present invention displays the contents shown in FIG. 9, and if a "Measurement/Record" portion in the display 10 is touched by a user, the "Measurement/Record" portion is displayed with blinking.

In this manner, it is assumed that, when the contents shown in FIG. 9 is displayed by the display 10, first of all, the user uses each vital sensor and the camera 5. At this time, the user touches a "Measurement/Record" in the display 10, and the display 10 displays the "Measurement/record" portion with blinking the "Measurement/record" portion as shown in FIG. 10 if the "Measurement/Record" portion is touched. After that, the display 10 changes the display contents to the contents shown in FIG. 11. In addition, in FIG. 10, it is assumed that slanted lines of the portion displaying the "Measurement/Record" denote that the portion displaying the "Measurement/Record" blinks, similarly slanted lines of the portion displaying the "Grandfather" in FIG. 6.

Figure 11:
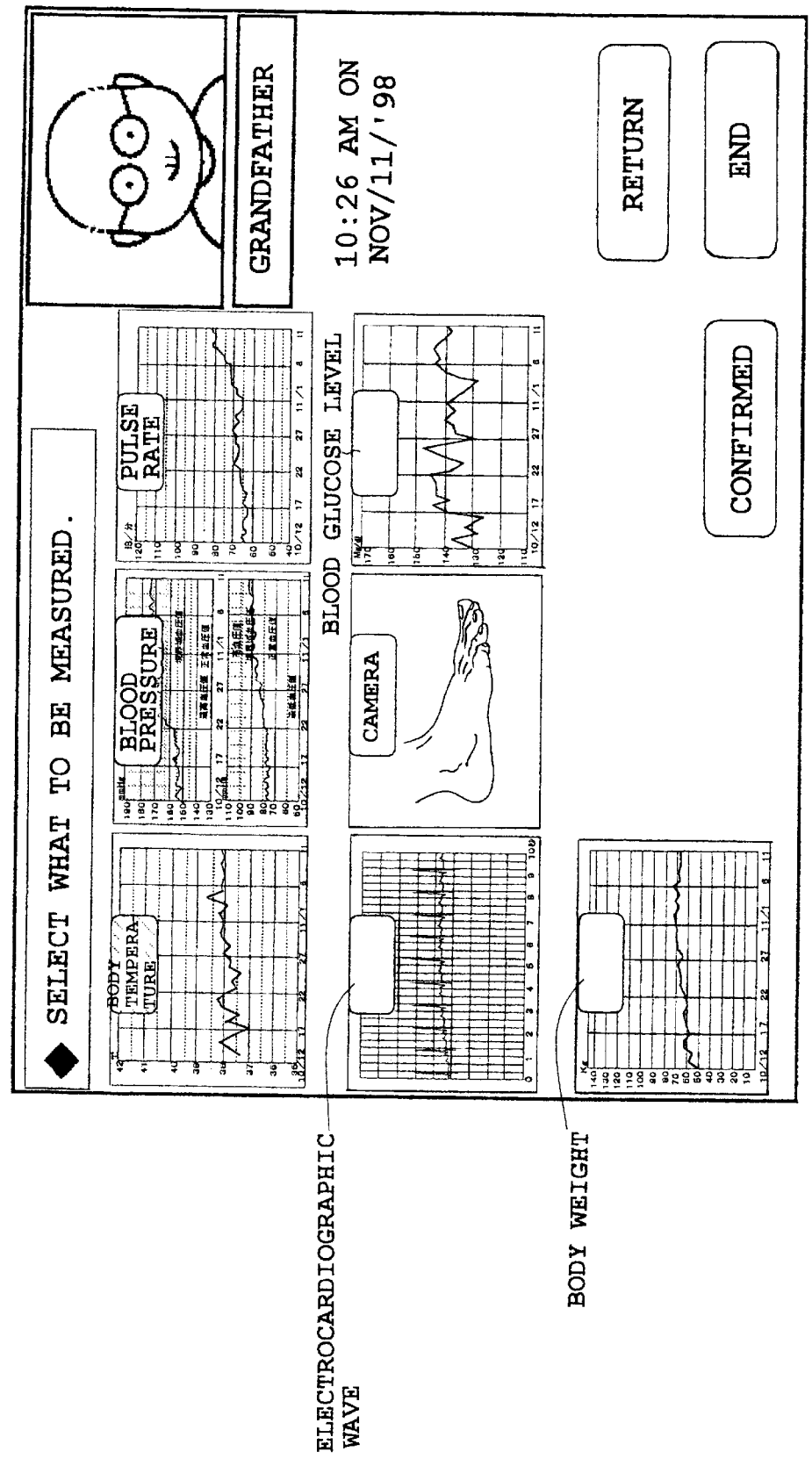
FIG. 11 is a diagram showing a display screen on which the vital sign box according to the first embodiment of the present invention lets a user select whether the user uses any one of each vital sensor and the camera 5.

By the way, FIG. 11 is a diagram showing a display screen on which the vital sign box lets a user select whether the user uses any one of each vital sensor and the camera 5. The "Temperature," "Blood pressure," "Electrocardio," "Camera," "Blood glucose level," and "Body weight" that are shown in FIG. 11 correspond to the earhole clinical thermometer 3, blood pressure monitor 2, electrocardiograph 1, camera 5, and blood glucose meter 4 in the vital sign box respectively. They are displayed with images obtained by graphing measurements measured by respective vital sensors. In addition, because the "Pulse rate" shown in FIG. 11 is measured by the blood pressure monitor 2, the "Pulse rate" corresponds to the blood pressure monitor 2. Furthermore, the "Body weight" corresponds to the scale outside the vital sign box.

Figure 12:
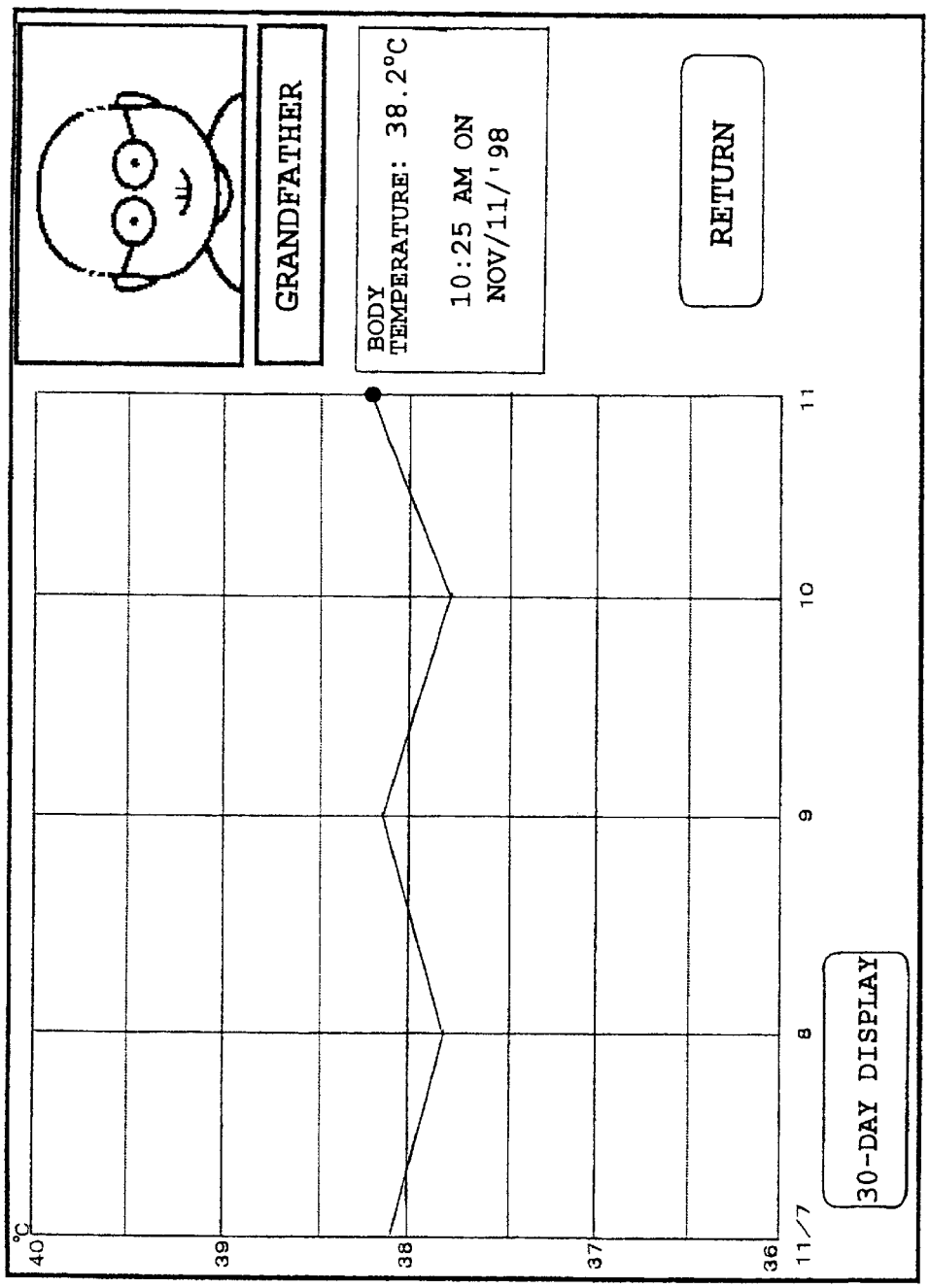
FIG. 12 is a diagram showing an example of a chart of a measurement result of body temperature measured by an earhole clinical thermometer 3 included in the vital sign box according to the first embodiment of the present invention.
Figure 13:
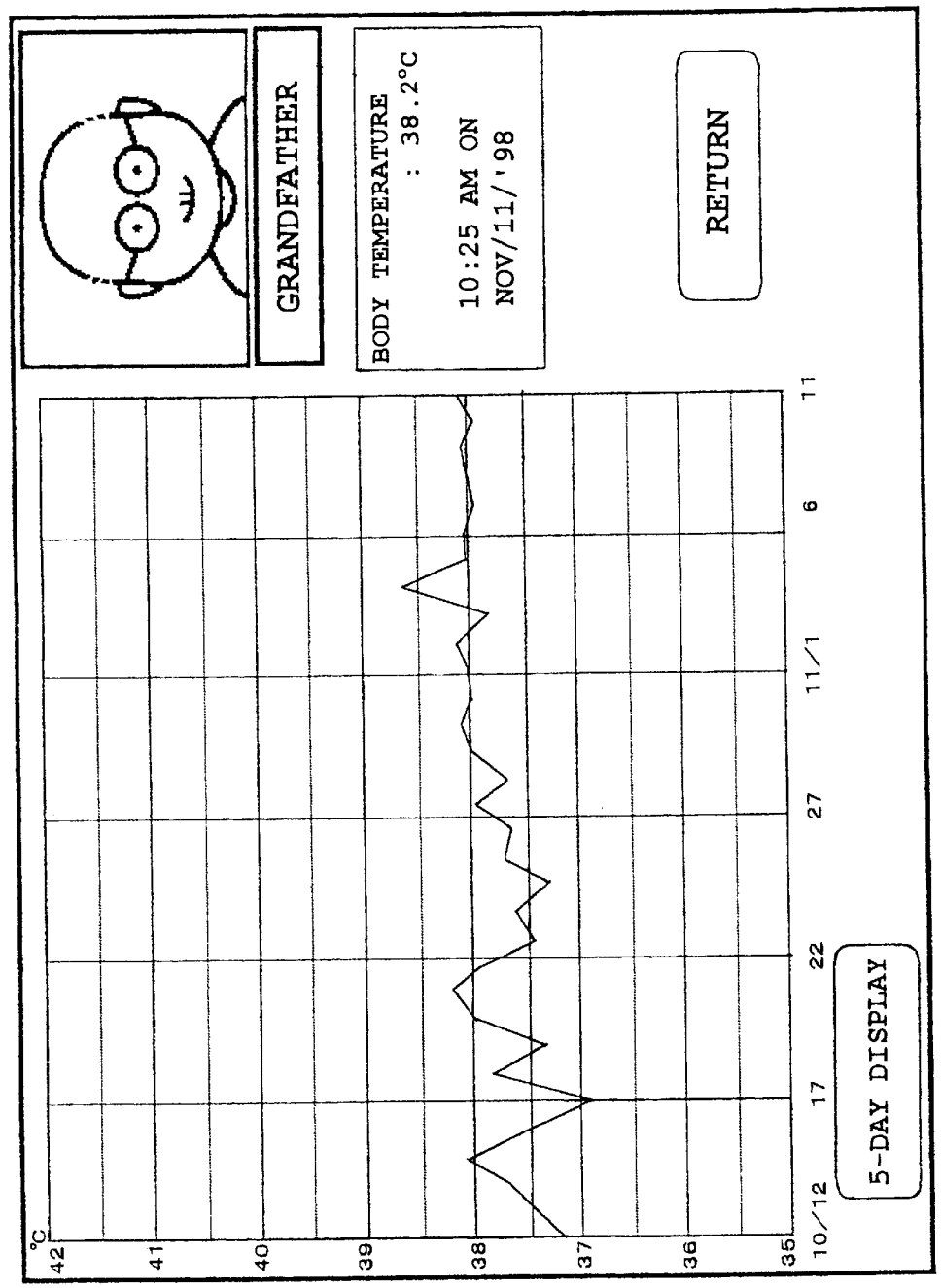
FIG. 13 is a diagram showing another example of a chart of a measurement result of body temperature measured by the earhole clinical thermometer 3 included in the vital sign box according to the first embodiment of the present invention, which is different from the example in FIG. 12.

By the way, it is assumed that, when the contents shown in FIG. 11 are displayed by the display 10, first of all, a user is going to measure the "Temperature." At this time, the user touches the "Temperature" in the display 10, takes out the earhole clinical thermometer 3 from the vital sign box, and measures body temperature by contacting the earhole clinical thermometer 3 to the user's earhole. Since being a cordless vital sensor, the earhole clinical thermometer 3 is convenient for a user to handle the thermometer 3. Then, when finishing the measurement of the body temperature, the user presses a send switch provided in the earhole clinical thermometer 3. When the send switch is pressed, the earhole clinical thermometer 3 transmits a measurement to the reception sensor 8 with using an infrared ray having a predetermined wavelength. In this manner, by letting a user press the send switch to transmit a measurement, it is possible to prevent the mishit or an input of a devious value that can be generated when letting the user input a measurement with using the ten-key pad. In addition, for a user, it becomes unnecessary to perform such troublesome work that the user inputs the measurement with using the ten-key pad. Next, when receiving the measurement from the earhole clinical thermometer 3, the reception sensor 8 not only outputs information as such to the speaker 11, but also outputs the information of the measurement to the memory 9. Then, the speaker 11 outputs such information that the reception sensor 8 has received the measurement from the earhole clinical thermometer 3 by sound. For example, the speaker 11 outputs such a sentence that "The measurement is received." by sound. In this manner, if the receipt information of a measurement is outputted by sound, a user can confirm that a measured measurement is received by the main body of the vital sign box. On the other hand, when receiving the measurement from the reception sensor 8, the memory 9 not only lets the display 10 display the measurement in a number as shown in FIG. 12, but also lets the display 10 display the measurements for last five days including the measurement inputted from the reception sensor 8. At that time, the display 10 displays a final measurement on a graph, in other words, the latest measurement with blinking the measurement. In FIG. 12, it is assumed that a measurement on November 11 is the final measurement, the final measurement is displayed as a black dot, and the black dot portion is displayed with blinking. In addition, the display 10 displays the graph with letting the final measurement be a reference and determining a predetermined range between a certain higher value and a certain lower value than the final measurement as a display range. For example, the display range is a range having the width of 3.5° C. between the final measurement +1.5° C./−2° C., and is determined so that each measurement in the display period is displayed in a substantially central part of the display screen. Thus, since fluctuations do not become clear if the display range becomes larger than the fluctuations of measurements, the display range is determined so that the fluctuations of the measurements become clear. In this manner, by letting a final measurement be a reference and determining a predetermined range between a certain higher value and a certain lower value than the final measurement as a display range, the fluctuations of daily measurements become clear. In addition, the display 10 displays with adjusting a display scale in order to make fluctuations of measurements clear. Furthermore, as show in FIG. 12, when displaying a graph of measurements for past five days including the final measurement, the display 10 displays a "30-day display" portion for changing the display contents in the lower left corner of the display screen simultaneously so that the measurements for past 30 days including the final measurement may be displayed as a graph. In addition, when the user touches the "30-day display" portion, the display 10, as shown in FIG. 13, displays the measurements for the last 30 days, including the final measurement, in the graph. Also, in regard to the graphical representation, in order that each measurement in the display period can be displayed in a substantially central part of the display screen, a display range is determined by making the final measurement value be a reference so that a predetermined range between a certain higher value and a certain lower value than the final measurement becomes the display range. In addition, a display scale is also determined so that fluctuations of measurements become clear. Furthermore, as show in FIG. 13, when displaying a graph of measurements for past 30 days including the final measurement, the display 10 displays a "5-day display" portion for changing the display contents in the lower left corner of the display screen simultaneously so that the measurements for past 5 days including the final measurement are redisplayed as a graph. When the user touches the "5-day display" portion, the display 10, as shown in FIG. 12, redisplays the measurements for the last 5 days in a graph. By the way, a measurement received by the reception sensor 8 is outputted as sound from the speaker 11. Then, if the user confirms display contents in FIG. 12 or 13 and touches a "Return" portion, the display 10 displays contents shown in FIG. 11 once again.

Next, it is assumed that, when the contents shown in FIG. 11 are displayed in the display 10, the user is going to measure "Blood pressure" and/or "Pulse rate." At this time, the user touches the "Blood pressure" or "Pulse rate" in the display 10, takes out the blood pressure monitor 2 from the vital sign box, and measures the blood pressure and pulse rate by wrapping the blood pressure monitor 2 around the user's arm. In addition, the blood pressure and pulse rate are measured at the substantially same time by the blood pressure monitor 2. Since being a cordless vital sensor, the blood pressure monitor 2 is convenient for a user to handle the blood pressure monitor 2. Then, when finishing the measurement of the blood pressure and pulse rate, the user presses a send switch provided in the blood pressure monitor 2. When the send switch is pressed, the blood pressure monitor 2 transmits a measurement to the reception sensor 8 with using an infrared ray having a predetermined wavelength. In this manner, by letting a user press the send switch to transmit a measurement, it is possible to prevent the mishit or an input of a devious value that can be generated when letting the user input a measurement with using the ten-key pad. Next, when receiving the measurement from the blood pressure monitor 2, the reception sensor 8 not only outputs information as such to the speaker 11, but also outputs the information of the measurement to the memory 9. Then, the speaker 11 outputs by sound such information that the reception sensor 8 has received the measurement from the blood pressure monitor 2.

Figure 14:
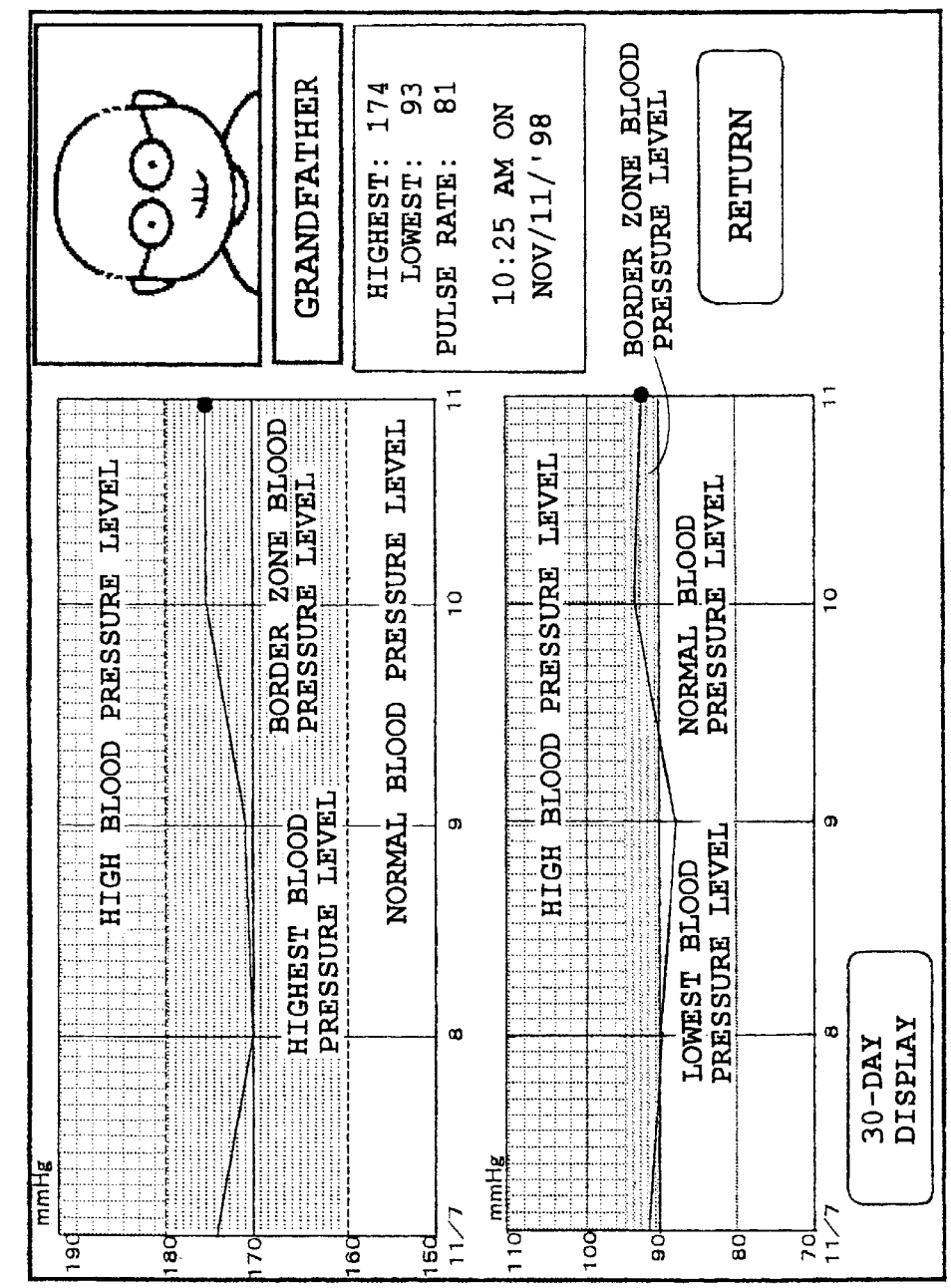
FIG. 14 is a diagram showing an example of charts of measurement results of blood pressure measured by a blood pressure monitor 2 included in the vital sign box according to the first embodiment of the present invention.

On the other hand, when receiving the measurement from the reception sensor 8, the memory 9 not only lets the display 10 display the measurement in a number as shown in FIG. 14, but also lets the display 10 display the measurements for last five days, including the measurement inputted from the reception sensor 8, in a graph. At that time, as shown in FIG. 14, the display 10 displays highest blood pressure level values and lowest blood pressure values independently in graphs in the same screen with dividing the display area. In addition, the display 10 displays final measurements on the graphs, in other words, the latest measurements with blinking the measurements. Furthermore, when displaying the graphs, the display 10 determines display ranges with the final measurement values as respective references. For example, the display range is a range having the width of 50 mmHg between the final measurement +15 mmHg/−35 mmHg, and is determined so that each measurement in the display period is displayed in a substantially central part of the display screen. Thus, since fluctuations do not become clear if the display range becomes larger than the fluctuations of measurements, the display range is determined so that the fluctuations of the measurements become clear. In this manner, by letting each final measurement be a reference and determining a predetermined range between a certain higher value and a certain lower value than each final measurement as each display range, the fluctuations of daily measurements become clear.

Figure 15:
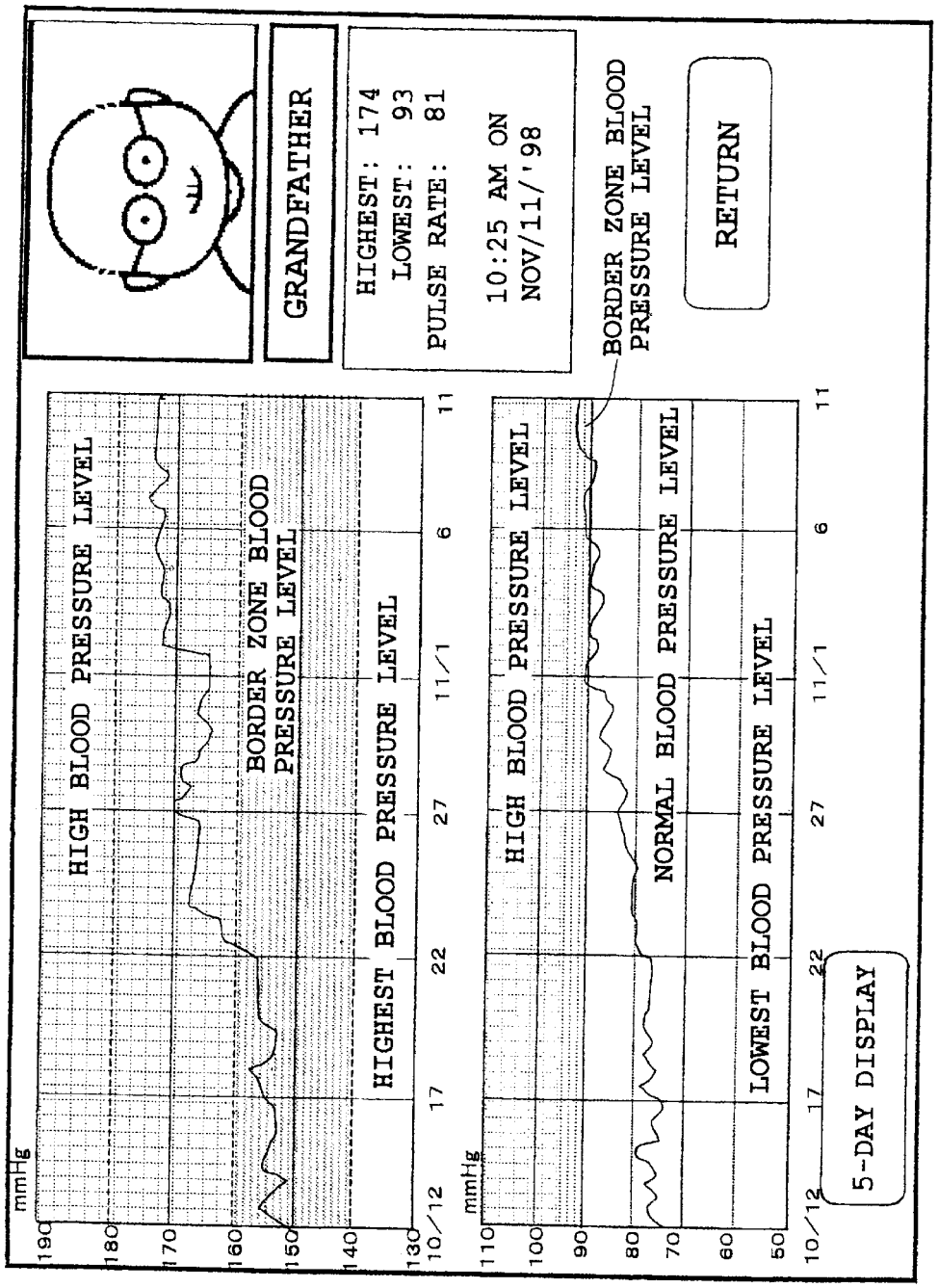
FIG. 15 is a diagram showing another example of charts of measurement results of blood pressure measured by the blood pressure monitor 2 included in the vital sign box according to the first embodiment of the present invention, which is different from the example in FIG. 14.

In addition, the display 10 displays with adjusting each display scale in order to make fluctuations of measurements clear. Furthermore, as show in FIG. 14, when displaying each graph of measurements for past five days including each final measurement, the display 10 displays each "30-day display" portion for changing the display contents in the lower left corner of the display screen simultaneously so that the measurements for past 30 days including each final measurement are displayed as each graph. In addition, when the user touches the "30-day display" portion, the display 10, as shown in FIG. 15, displays the measurements for the last 30 days, including each final measurement, in each graph. Also, in regard to the graphical representation, in order that each measurement in the display period can be displayed in a substantially central part of the display screen, each display range is determined by making the final measurement value be a reference so that each predetermined range between a certain higher value and a certain lower value than the final measurement becomes each display range. In addition, each display scale is also determined so that fluctuations of measurements become clear. Furthermore, as show in FIG. 15, when displaying each graph of measurements for past 30 days including each final measurement, the display 10 displays a "5-day display" portion for changing the display contents in the lower left corner of the display screen simultaneously so that the measurements for past 5 days including each final measurement are redisplayed as each graph. When the user touches the "5-day display" portion, the display 10, as shown in FIG. 14, redisplays the measurements for the last 5 days in each graph. By the way, a measurement received by the reception sensor 8 is outputted as sound from the speaker 11.

Figure 16:
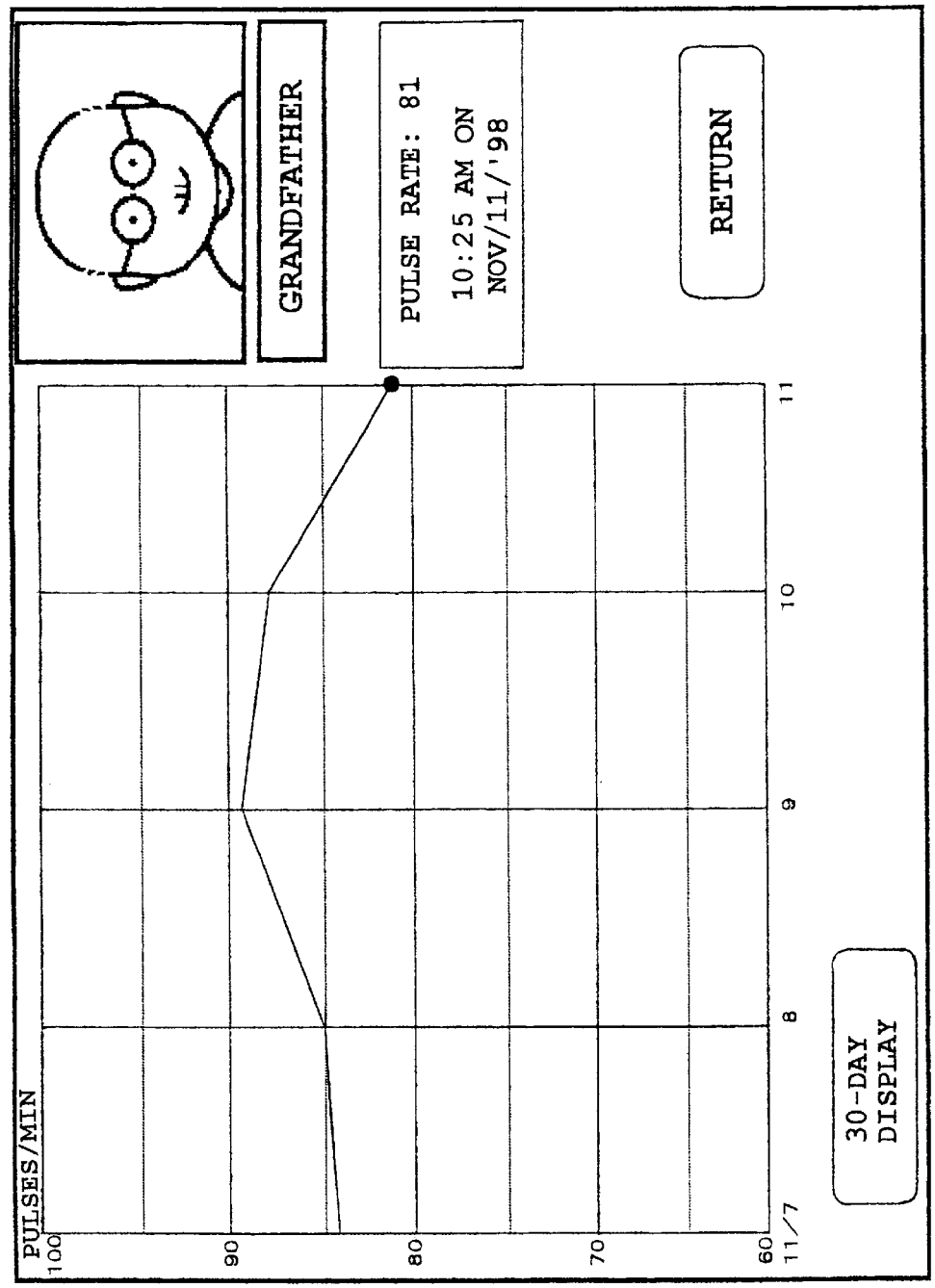
FIG. 16 is a diagram showing an example of a chart of a measurement result of pulse rates measured by the blood pressure monitor 2 included in the vital sign box according to the first embodiment of the present invention.
Figure 17:
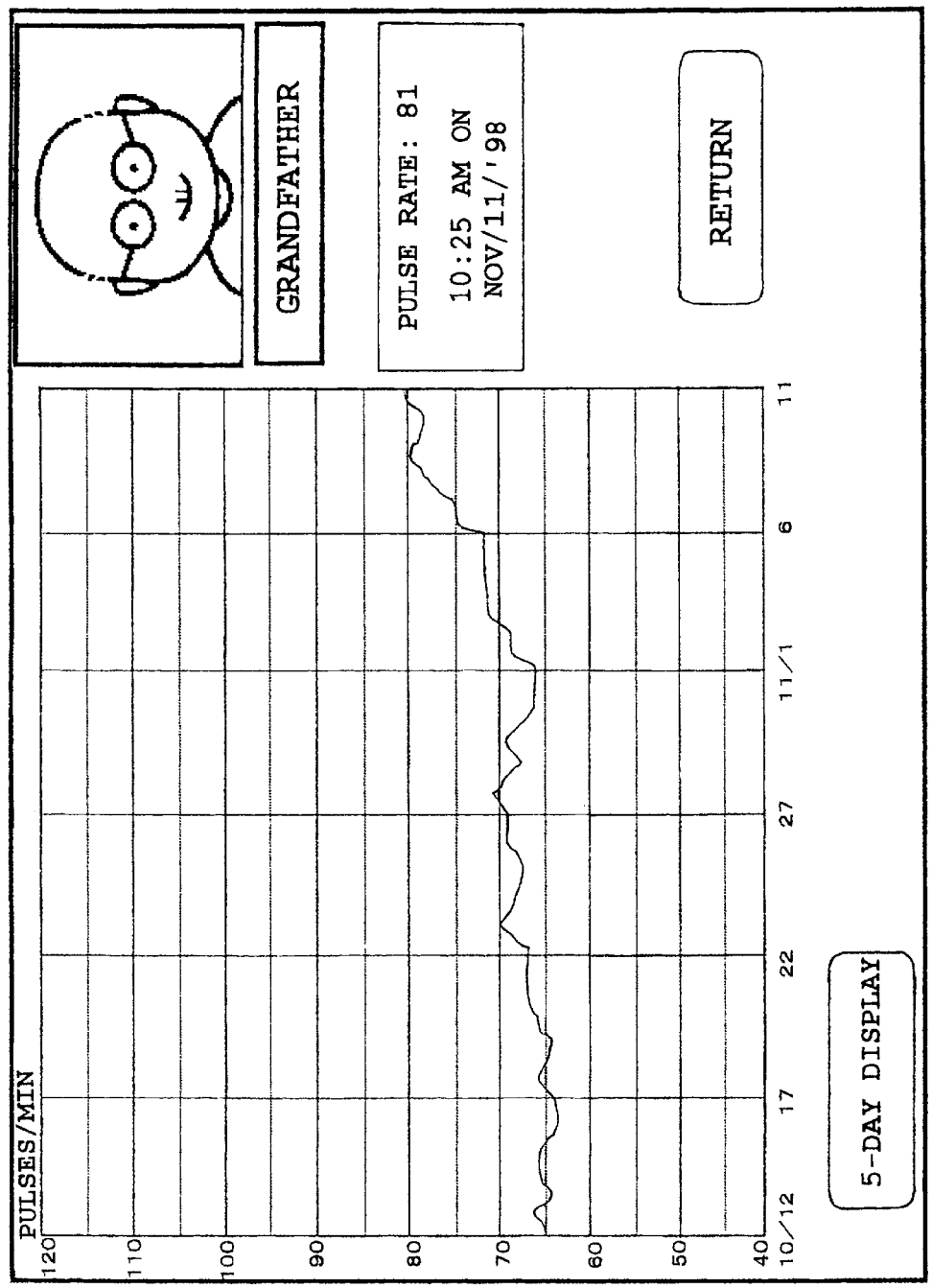
FIG. 17 is a diagram showing another example of a chart of a measurement result of pulse rates measured by the blood pressure monitor 2 included in the vital sign box according to the first embodiment of the present invention, which is different from the example in FIG. 16.

In this manner, if a screen showing the measurement result of blood pressure is displayed in the display 10 and display contents do not change from that status, for example, predetermined time of five seconds passes, the display 10 not only displays measurements in numbers about the measurement result of pulse rates as shown in FIG. 16, but also displays as a graph the measurements for past five days including the measurement inputted from the reception sensor 8. At that time, the display 10 not only blinks and displays the final measurement, but also displays the graph after determining a display range with the final measurement as a reference so that each measurement in a display period is displayed in a substantially central part of the display screen. In addition, a display scale is also determined so that fluctuations of measurements become clear, and the graph is displayed. Furthermore, as show in FIG. 16, when displaying a graph of measurements of pulse rates for past five days including the final measurement, the display 10 displays a "30-day display" portion for changing the display contents in the lower left corner of the display screen simultaneously so that the measurements for past 30 days including the final measurement are displayed as a graph. In addition, when the user touches the "30-day display" portion, the display 10, as shown in FIG. 17, displays the measurements for the last 30 days, including the final measurement, in the graph. Also, in regard to the graphical representation, in order that each measurement in the display period can be displayed in a substantially central part of the display screen, the display range is determined. In addition, a display scale is also determined so that fluctuations of measurements become clear. Furthermore, as show in FIG. 17, when displaying a graph of measurements for past 30 days including the final measurement, the display 10 displays a "5-day display" portion for changing the display contents in the lower left corner of the display screen simultaneously so that the measurements for past 5 days including the final measurement are redisplayed as a graph. When the user touches the "5-day display" portion, the display 10, as shown in FIG. 16, redisplays the measurements of pulse rates for the last 5 days in a graph. In addition, a measurement of a pulse rate received by the reception sensor 8 is also outputted as sound from the speaker 11.

Now, if a screen showing the measurement result of pulse rates is displayed in the display 10 and display contents do not change from that status, for example, predetermined time of five seconds passes, the display 10 changes display contents from the measurement result of the pulse rates to the contents shown in FIG. 14 about the measurement result of blood pressure. In this manner, if not receiving the user's instruction for changing the display of the measurement period of the graph within predetermined time, the display 10 changes display contents so as to switch between the measurement result of blood pressure and measurement result of pulse rates.

In any case, if the user confirms the display contents when the display 10 displays any one of FIGS. 14 to 17, and touches a "Return" portion, the contents shown in FIG. 11 are displayed once again in the display 10.

Figure 18:
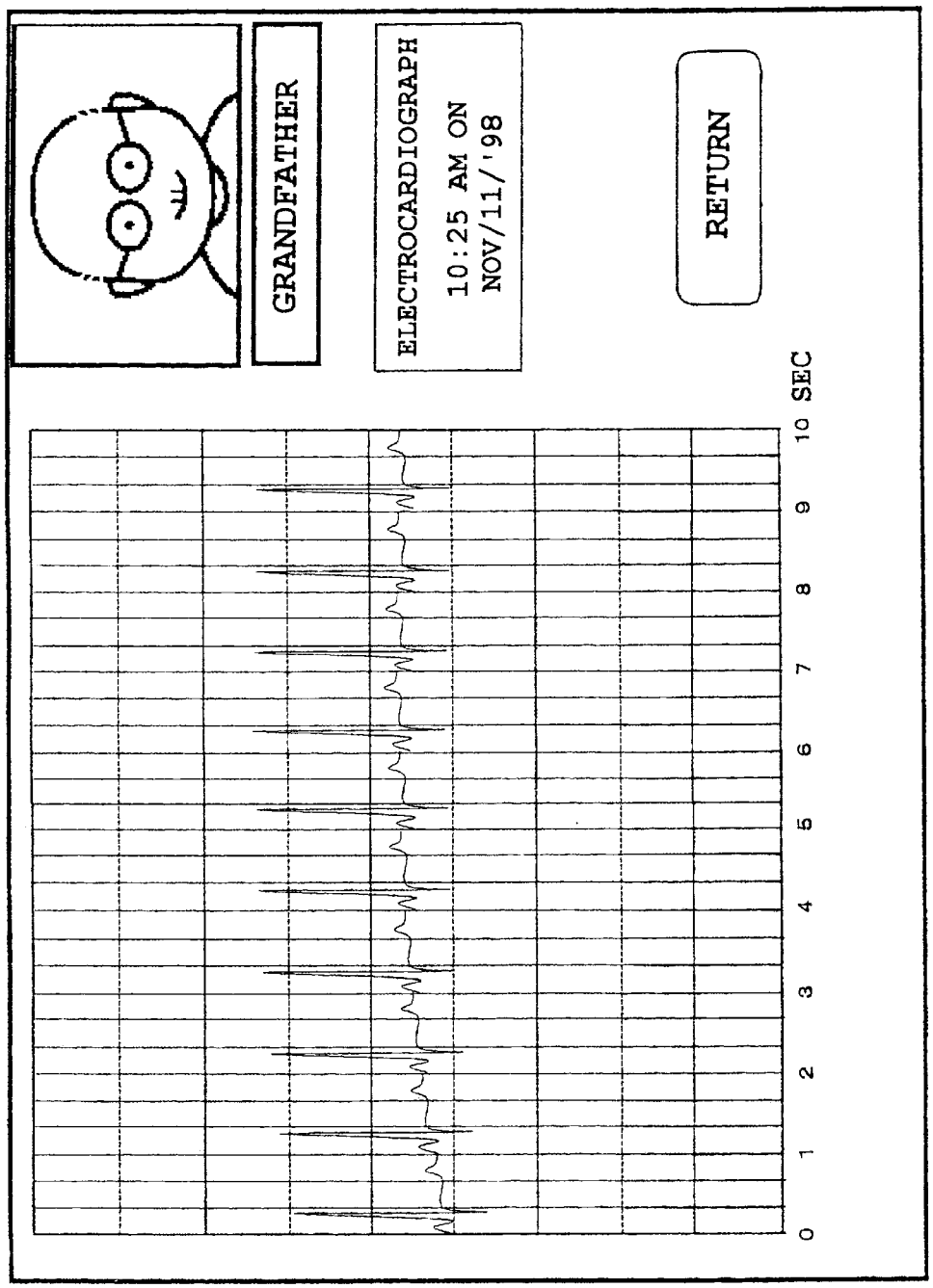
FIG. 18 is a diagram showing an example of an electrocardiogram measured by the electrocardiograph 1 of the vital sign box according to the first embodiment of the present invention.

It is assumed that, when contents shown in FIG. 11 are next displayed in the display 10, the user is going to measure "Electrocardio." At this time, the user touches the "Electrocardio" in the display 10, takes out the electrocardiograph 1 from the vital sign box, and measures the electrocardio by contacting the contact section for a left arm 1a, and contact section for a right arm 1b to left and right arms respectively. The user presses a send switch provided in the electrocardiograph 1 during the electrocardio measurement, and when the send switch is pressed, the electrocardiograph 1 transmits a measurement to the LED 7 through a connection cord with using an electrical signal. In this manner, by letting a user press the send switch to transmit a measurement, it is possible to prevent the mishit or an input of a devious value that can be generated when letting the user input a measurement with using the ten-key pad. The LED 7 converts each measurement, transmitted with using electrical signals from the electrocardiograph 1, into an infrared ray having a predetermined wavelength and transmits the measurement to the reception sensor 8. When receiving the measurement by the electrocardiograph 1 from the LED 7 in the infrared ray, the reception sensor 8 not only outputs information as such to the speaker 11, but also outputs the information of the measurement to the display 10 and the memory 9. Then, the speaker 11 outputs by sound such information that the reception sensor 8 has received the measurement from the electrocardiograph 1. The display 10, as shown in FIG. 18, displays an electrocardiographic waveform on the basis of the measurement received by the LED 7, in real time for a predetermined period of, for example, 10 seconds. At that time, the display 10 displays the electrocardiographic waveform so that the electrocardiographic waveform is continuously displayed. In addition, if one electrocardio measuring period is, for example, 50 seconds, at the time of finishing the measurement the display 10 displays the waveform equivalent to the last predetermined time of predetermined electrocardio measuring time of, for example, the last ten seconds. In addition, so as to make fluctuations of the electrocardio clear when displaying, an electrocardiographic waveform, the display 10 displays an electrocardiogram so that a status of the fluctuations of the electrocardio is displayed in a substantially central part of the display screen. In addition, the display 10 displays the electrocardiogram with adjusting a display scale in order to make fluctuations of measurements clear. On the other hand, the memory 9 records waveform data for the last predetermined time in a predetermined electrocardio measuring time, for example, for last ten seconds, which is displayed at the time of finishing the measurement in the display 10. Then, if the user confirms display contents in FIG. 18 and touches a "Return" portion, the display 10 displays contents shown in FIG. 11 once again.

Next, it is assumed that, when contents shown in FIG. 11 are displayed in the display 10, the user is going to use the camera 5. At this time, the user touches a "Camera" portion in the display 10.

Figure 19:
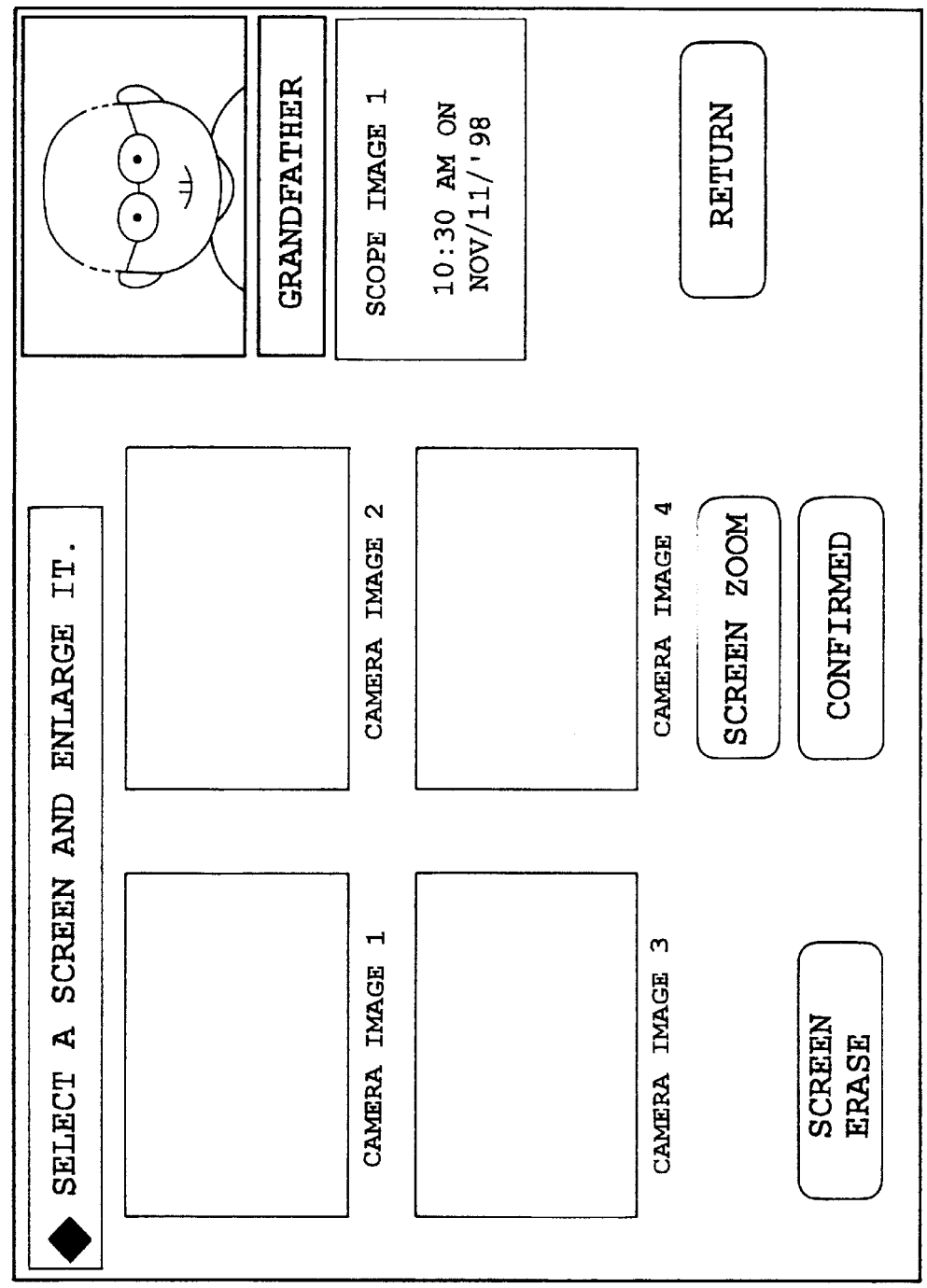
FIG. 19 is an explanatory diagram of a display area when objects, whose pictures are taken by an camera 5 of the vital sign box according to the first embodiment of the present invention, are displayed in a display 10.
Figure 20:
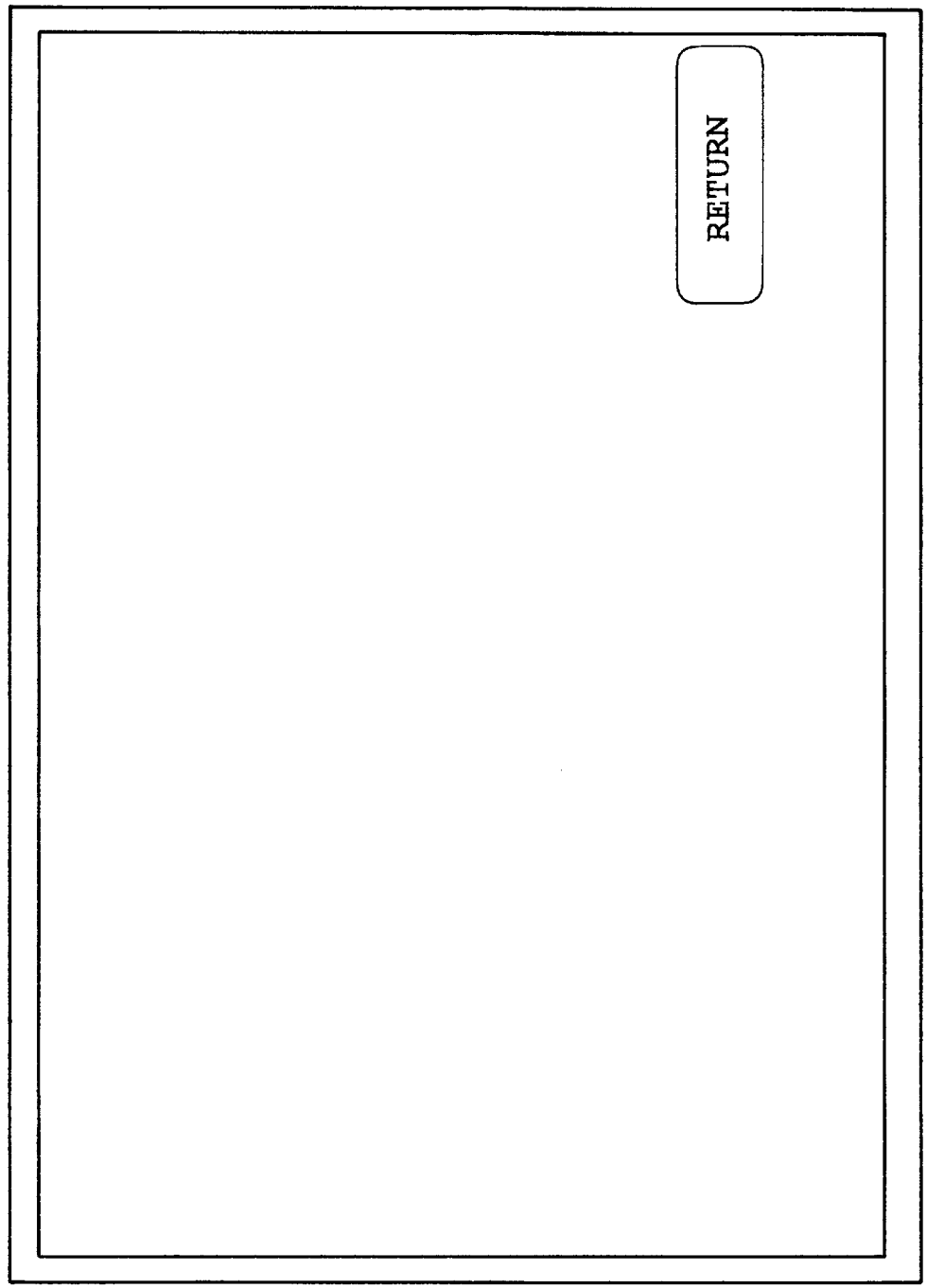
FIG. 20 is an explanatory diagram of a display area when an object, whose picture is taken by an camera 5 of the vital sign box according to the first embodiment of the present invention is displayed in a display 10 with being magnified.

By the way, a main body of the housing 14 of the vital sign box is put on a predetermined mount and the like so that the height of a CCD of the camera 5 becomes substantially equal to the height of a central part of the user's face when the base 6 is stood substantially vertical to the bottom face of the vital sign box with using the connecting section 6a while, as shown in FIG. 4, the camera 5 is housed in the base 6. When the user is going to take a picture of the user's own face with the camera 5, the user lets the camera 5 take a picture of the user's own face with practically vertically standing and fixing the base 6 to the bottom face of the vital sign box while the camera 5 is housed in the base 6. Then, an image shot by the camera 5 is displayed as any one of camera images 1 to 4 in the display 10 that are shown in FIG. 19. By the way, the display 10, as shown in FIG. 19, displays "Screen zoom" and "Screen erase" in the lower side of the screen when displaying the image of an object such as a face. When the user is going to enlarge any one of the camera images 1 to 4, the user touches the image among the camera images 1 to 4 that the user is going to enlarge, and furthermore, touches the "Screen zoom" portion. When the "Screen zoom" portion is touched, the image among the camera images 1 to 4 that is touched by the user beforehand is enlarged and displayed in the display 10 as shown in FIG. 20. In case of finishing the zoom, when the user touches the "Return" portion in display contents that are shown in FIG. 20 and are displayed in the display 10, the contents shown in FIG. 19 are displayed once again in the display 10. In addition, if the user is going to erase any one of the camera images 1 to 4, the user touches the image among the camera images 1 to 4 that the user is going to erase, and touches the "Screen erase" portion. The image is erased if the "Screen erase" is touched. Furthermore, when a user is going to record any image among the camera images 1 to 4 in the memory 9, the user touches the image among the camera images 1 to 4 that the user is going to record. When the image that the user is going to record in the memory 9 is displayed in a frame of the camera image touched, the user presses a switch that is used to record an image and is provided in the camera 5. In this manner, when the switch is pressed, the image at that timing is recorded in the memory 9 as a static image. In addition, since the camera 5 is connected to the main body of the vital sign box with a connecting cord, the image that is shot is outputted through the connecting cord to the display 10 and/or memory 9. Furthermore, it is assumed that the memory 9 can record up to four images. Moreover, different four images that are taken by the camera 5 can be displayed in the display 10 simultaneously as shown in FIG. 19. Then, it is assumed that it is possible that, so as to display the fifth image different from the images displayed, for example, the fifth image enters into the frame of the camera image 1, and other images are sequentially shifted and displayed as the image having been included in the frame of the camera image 1 enters into the frame of the camera image 2 and so on.

By the way, differently from the above-described status, there is a case that, for example, the main body of the housing 14 of the vital sign box is not put on the predetermined mount described above, and the height of the CCD of the camera 5 is not equal to the height of the central part of the user's face when the base 6 is stood substantially vertically to the bottom face of the vital sign box while the camera 5 is housed in the base 6. Nevertheless, in case a user is going to take a picture of the user's own face with the camera 5, the user takes a picture of the user's own face by rotating the base 6 with using the connecting section 6a of the base 6 while the camera 5 is contained in the base 6, and fixing the base 6 with inclining the base 6 at a predetermined angle to the bottom face of the vital sign box. The base 6 is rotatable and can be fixed at the predetermined angle of gradient. Hence, it is possible to take a picture of the user's own face and the like with the camera 5 without changing the user's posture by fixing the base 6 in a predetermined direction and at a predetermined angle of gradient.

In addition, the camera 5 is detachable from the base 6. Hence, if a user is going to take a picture of, for example, the user's ankle instead of the user's face with the camera 5, the user takes out the camera 5 from the base 6, and can take a picture of the ankle with holding the camera 5 in user's hands and so on.

Furthermore, since having a lighting section for lighting an imaging object, the camera 5 can take a clear picture. In addition, since having a function capable of enlarging and shrinking an image, the camera 5 can take an image, which is enlarged or shrunk, and lets the display 10 display the image.

After that, if the user confirms display contents in FIG. 19 and touches a "Return" portion, the display 10 displays contents shown in FIG. 11 once again.

Figure 21:
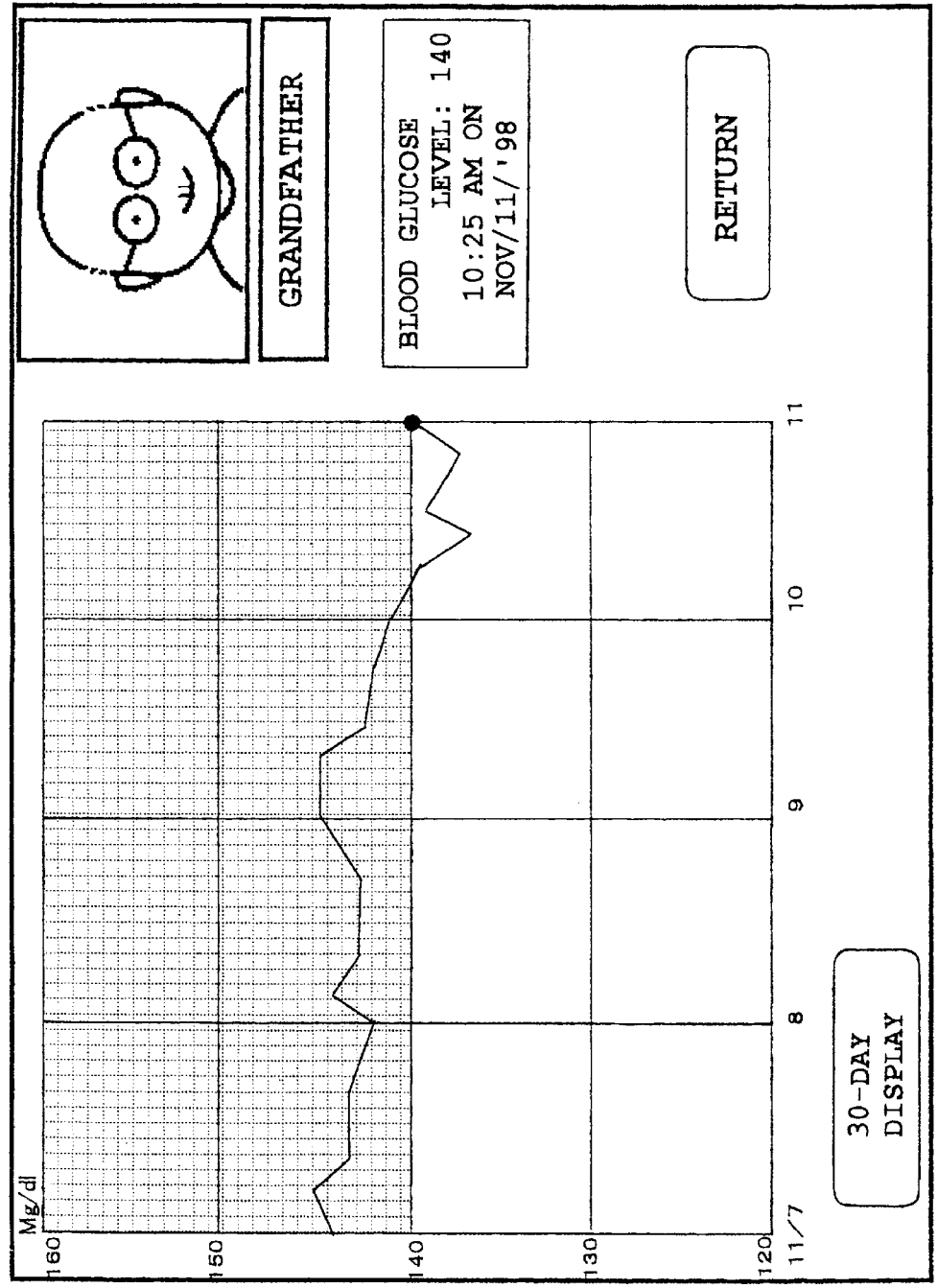
FIG. 21 is a diagram showing an example of a chart of a measurement result of blood glucose levels measured by a glucose meter 4 included in the vital sign box according to the first embodiment of the present invention.
Figure 22:
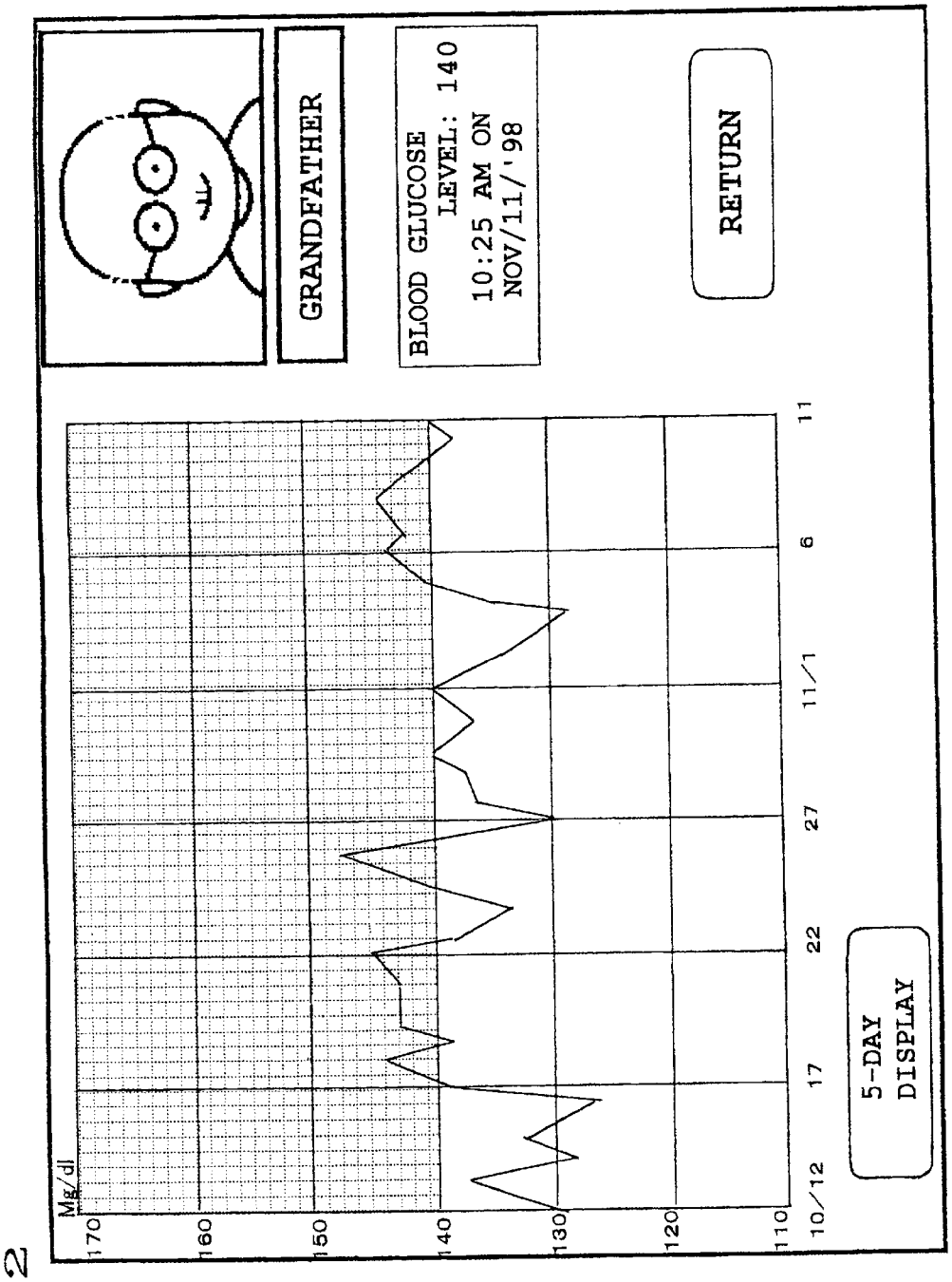
FIG. 22 is a diagram showing another example of a chart of a measurement result of blood glucose levels measured by the glucose meter 4 included in the vital sign box according to the first embodiment of the present invention, which is different from the example in FIG. 21.

It is assumed that, when contents shown in FIG. 11 is next displayed in the display 10, the user is going to measure a "Blood glucose level." At this time, the user touches a "Blood glucoses" portion in the display 10, and takes out the blood glucose meter 4, blood-collecting needle 4a, and sensor chip 4b from the vital sign box to attach the sensor chip 4b at a predetermined position of the blood glucosemeter 4. Next, the user collects the user's own blood of about 5 µl (micro liter) with using the blood-collecting needle 4b to drip the blood, which is collected, on the sensor chip 4b. Then, the user measures sugar density in the blood with using the sensor chip 4b attached on the blood glucose meter 4. When finishing the measurement of the sugar density in the blood, the user connects the connection jack 4c to the blood glucose meter 4, and furthermore, connects the connection jack 4c to the main body of the vital sign box to press the send switch provided in the blood glucose meter 4. When the send switch is pressed, the blood glucose meter 4 transmits the measurement to the LED 7, provided in the main body of the vital sign box, through the connection jack 4c with using an electrical signal. The LED 7 converts the measurement, transmitted with using the electrical signal from the blood glucose meter 4, into an infrared ray having a predetermined wavelength and transmits the measurement to the reception sensor 8. When receiving the measurement by the blood glucose meter 4 from the LED 7 in the infrared ray, the reception sensor 8 not only outputs information as such to the speaker 11, but also outputs the information of the measurement to the memory 9. Then, the speaker 11 outputs by sound such information that the reception sensor 8 has received the measurement from the blood glucose meter 4. On the other hand, when receiving the measurement from the reception sensor 8, the memory 9 not only lets the display 10 display the measurement in a number as shown in FIG. 21, but also lets the display 10 display the measurements for last five days including the measurement inputted from the reception sensor 8. At that time, the display 10 displays and blinks the final measurement. In addition, the display 10 displays the graph with letting the final measurement be a reference and defining a predetermined range between a certain higher value and a certain lower value than the final measurement as a display range. Furthermore, in order that each measurement in the display period can be displayed in a substantially central part of the display screen, the graph is displayed. In addition, the display 10 displays the graph with adjusting a display scale in order to make fluctuations of measurements clear. Furthermore, as show in FIG. 21, when displaying each graph of measurements for past five days including each final measurement, the display 10 displays each "30-day display" portion for changing the display contents in the lower left corner of the display screen simultaneously so that the measurements for past 30 days including each final measurement are displayed as each graph. In addition, when the user touches the "30-day display" portion, the display 10, as shown in FIG. 22, displays the measurements for the last 30 days, including the final measurement, in the graph. Also, in regard to the graphical representation, in order that each measurement in the display period can be displayed in a substantially central part of the display screen, each display range is determined by making the final measurement value be a reference so that each predetermined range between a certain higher value and a certain lower value than the final measurement becomes each display range. In addition, a display scale is also determined so that fluctuations of measurements become clear. Furthermore, as show in FIG. 22, when displaying a graph of measurements for past 30 days including the final measurement, the display 10 displays a "5-day display" portion for changing the display contents in the lower left corner of the display screen simultaneously so that the measurements for past 5 days including the final measurement are redisplayed as a graph. When the user touches the "5-day display" portion, the display 10, as shown in FIG. 21, redisplays the measurements for the last 5 days in a graph. By the way, a measurement received by the reception sensor 8 is outputted as sound from the speaker 11. Then, if the user confirms display contents in FIG. 21 or 22 and touches a "Return" portion, the display 10 displays contents shown in FIG. 11 once again.

Figure 23:
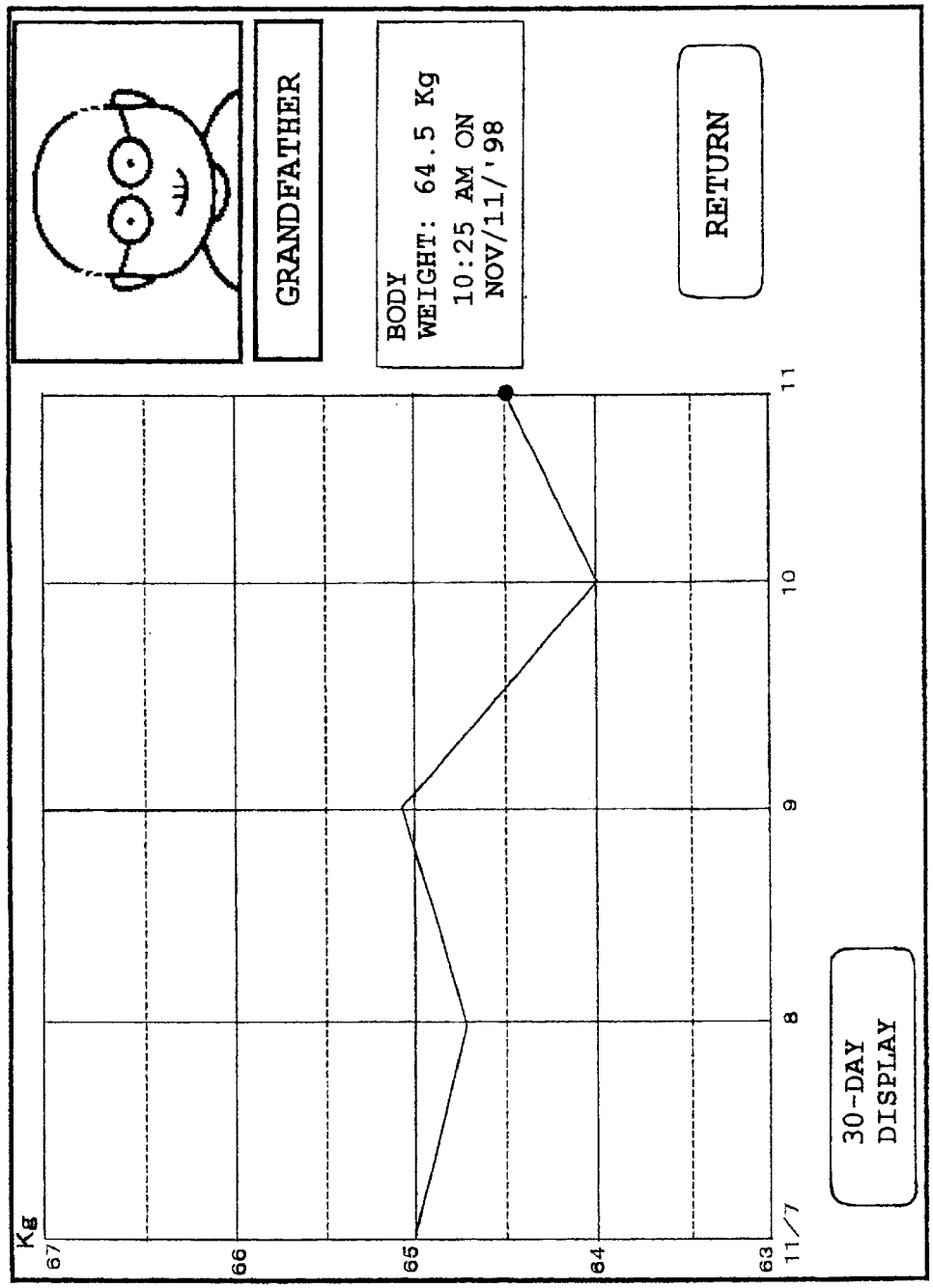
FIG. 23 is a diagram showing an example of a chart of a measurement result of body weight measured by a scale that can perform data transmission to the vital sign box according to the first embodiment of the present invention.
Figure 24:
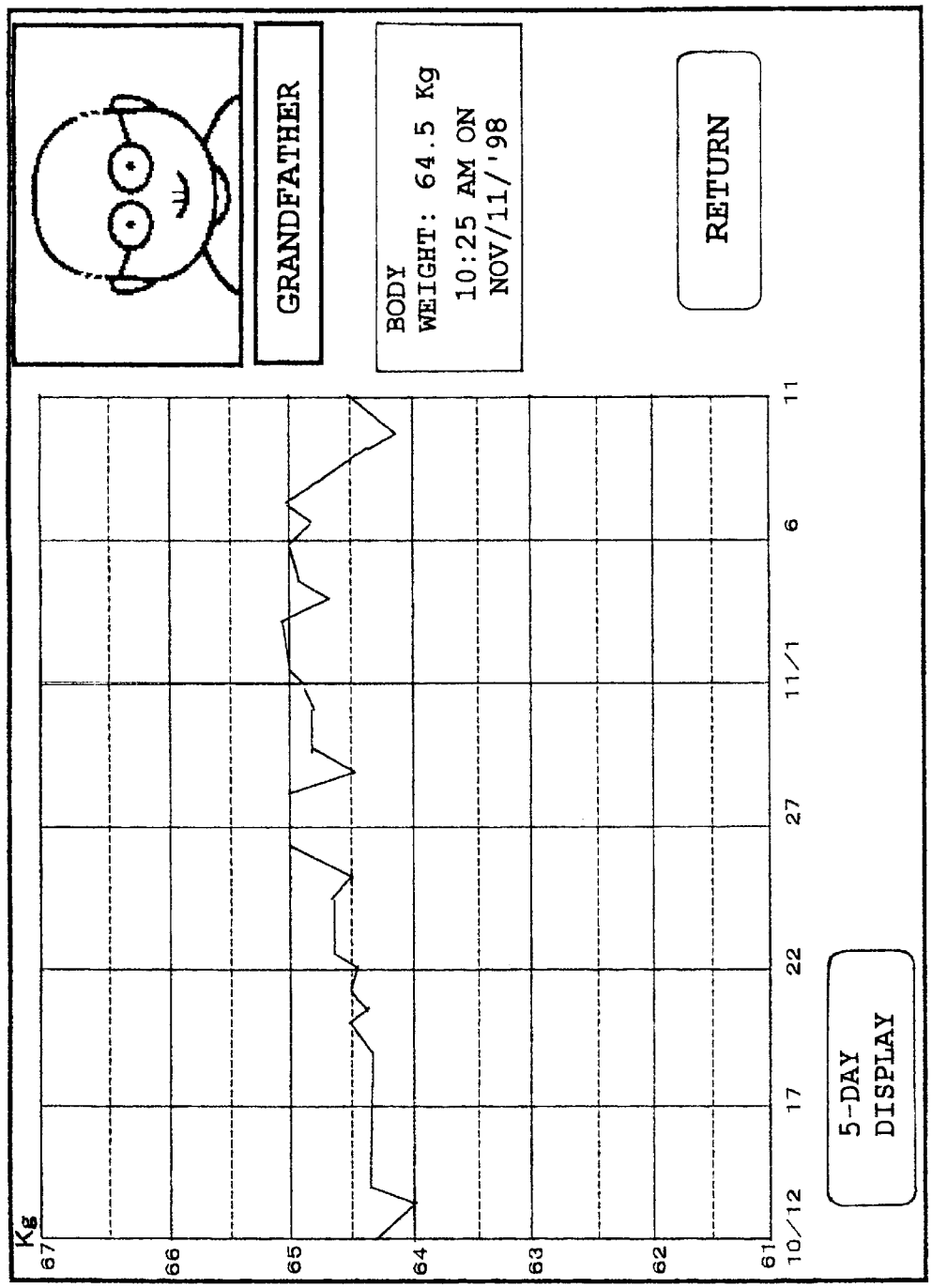
FIG. 24 is a diagram showing another example of a chart of a measurement result of body weight measured by the scale that can perform data transmission to the vital sign box according to the first embodiment of the present invention, which is different from the example in FIG. 23.

Next, it is assumed that, when contents shown in FIG. 11 are displayed in the display 10, the user is going to measure "Body weight." At this time, the user touches a "Body weight" portion in the display 10. Then, the user measures the user's own body weight by mounting the scale outside the vital sign box, the scale that can transmit the measurement to the vital sign box with using an infrared ray having a predetermined wavelength. When finishing the measurement of the body weight, the scale transmits a measurement to the reception sensor 8 with using the infrared ray having the predetermined wavelength. When receiving the measurement from the scale, the reception sensor 8 not only outputs information as such to the speaker 11, but also outputs the information of the measurement to the memory 9. Then, the speaker 11 outputs by sound such information that the reception sensor 8 has received the measurement from the scale. On the other hand, when receiving the measurement from the reception sensor 8, the memory 9 not only lets the display 10 display the measurement in a number as shown in FIG. 23, but also lets the display 10 display the measurements for last five days including the measurement inputted from the reception sensor 8. At that time, the display 10 displays and blinks the final measurement. In addition, with letting the final measurement be a reference and determining a predetermined range between a certain higher value and a certain lower value than the final measurement as a display range, the display 10 displays the graph, so that each measurement in the display period can be displayed in a substantially central part of the display screen. In addition, the display 10 displays with adjusting a display scale in order to make fluctuations of measurements clear. Furthermore, as show in FIG. 23, when displaying each graph of measurements for past five days including each final measurement, the display 10 displays each "30-day display" portion for changing the display contents in the lower left corner of the display screen simultaneously so that the measurements for past 30 days including each final measurement are displayed as each graph. In addition, when the user touches the "30-day display" portion, the display 10, as shown in FIG. 24, displays the measurements for the last 30 days, including the final measurement, in the graph. Also, in regard to the graphical representation, in order that each measurement in the display period can be displayed in a substantially central part of the display screen, each display range is determined by making the final measurement value be a reference so that each predetermined range between a certain higher value and a certain lower value than the final measurement becomes each display range. In addition, a display scale is also determined so that fluctuations of measurements become clear. Furthermore, as show in FIG. 24, when displaying a graph of measurements for past 30 days including the final measurement, the display 10 displays a "5-day display" portion for changing the display contents in the lower left corner of the display screen simultaneously so that the measurements for past 5 days including the final measurement are redisplayed as a graph. When the user touches the "5-day display" portion, the display 10, as shown in FIG. 23, redisplays the measurements for the last 5 days in a graph. By the way, the measurement received by the reception sensor 8 is outputted as sound from the speaker 11. Then, if the user confirms display contents in FIG. 23 or 24 and touches a "Return" portion, the display 10 displays contents shown in FIG. 11 once again.

As described above, when all or part of the respective vital sensors, camera 5, and scale are used and the use is finished, the contents shown in FIG. 11 are displayed in the display 10. At this time, the user touches the "Return" portion in FIG. 11, and when the "Return" is touched by the user, the display 10 displays the contents shown in FIG. 9.

It is assumed that, when contents shown in FIG. 9 are next displayed in the display 10, the user lets the display 10 display measurements and/or shot images stored in the memory 9. At this time, the user touches a "Display" in the display 10, and the display 10 displays and blinks the "Display" portion when the "Display" portion is touched, and after that, changes the display contents to the contents shown in FIG. 11.

In addition, when the contents shown in FIG. 11 are displayed in the display 10, the user determines which data of the "Temperature, "Blood pressure," "Pulse rate," "Electrocardio," and "Blood glucose level" measured by respective vital sensors, images taken by the camera 5, and the "Body weight" measured by the scale, that are stored in the memory 9, is displayed in the display 10. Then, the user touches an adequate portion among the "Temperature," "Blood pressure," "Pulse rate," "Electrocardio," "camera," "Blood glucose level," and "Body weight" in the display 10 that corresponds to the data determined. The display 10 reads measurements and graph(s), or data of shot images, which correspond to the portion touched by the user, from the memory 9, and displays them. In addition, the data displayed in the display 10 is the data displayed in realtime in the display 10 at the time of measuring an object or taking a picture that are explained with using FIGS. 12 to 24.

Furthermore, although there are two kinds of graphs of measurements relating to, for example, "Body weight" and the like as shown in FIGS. 12 and 13, first of all a 5-day graph shown in FIG. 12 is displayed in the display 10. Then, similarly to the above description on the display method of measurements in a graph, by the user touching the "30-day display" portion displayed in the display 10 so as to let display 10 display the 30-day graph, the 30-day graph shown in FIG. 13 is displayed in the display 10. In this manner, it is assumed that, in the case of letting the display 10 display data stored in the memory 9 and being able to display the data obtained by the respective vital sensors, camera 5, or scale as two kinds of screens, which screen is to be displayed is determined similarly to the case of letting the display 10 display a measurement measured in realtime and a shot image.

In addition, when the user confirms the display contents of data, recorded in the memory 9, in the display 10, the user touches the "Return" portion of the screen to change the display contents in the display 10 to the contents shown in FIG. 11. Furthermore, the user touches the "Return" portion shown in FIG. 11 to change the contents shown in FIG. 9.

Figure 25:
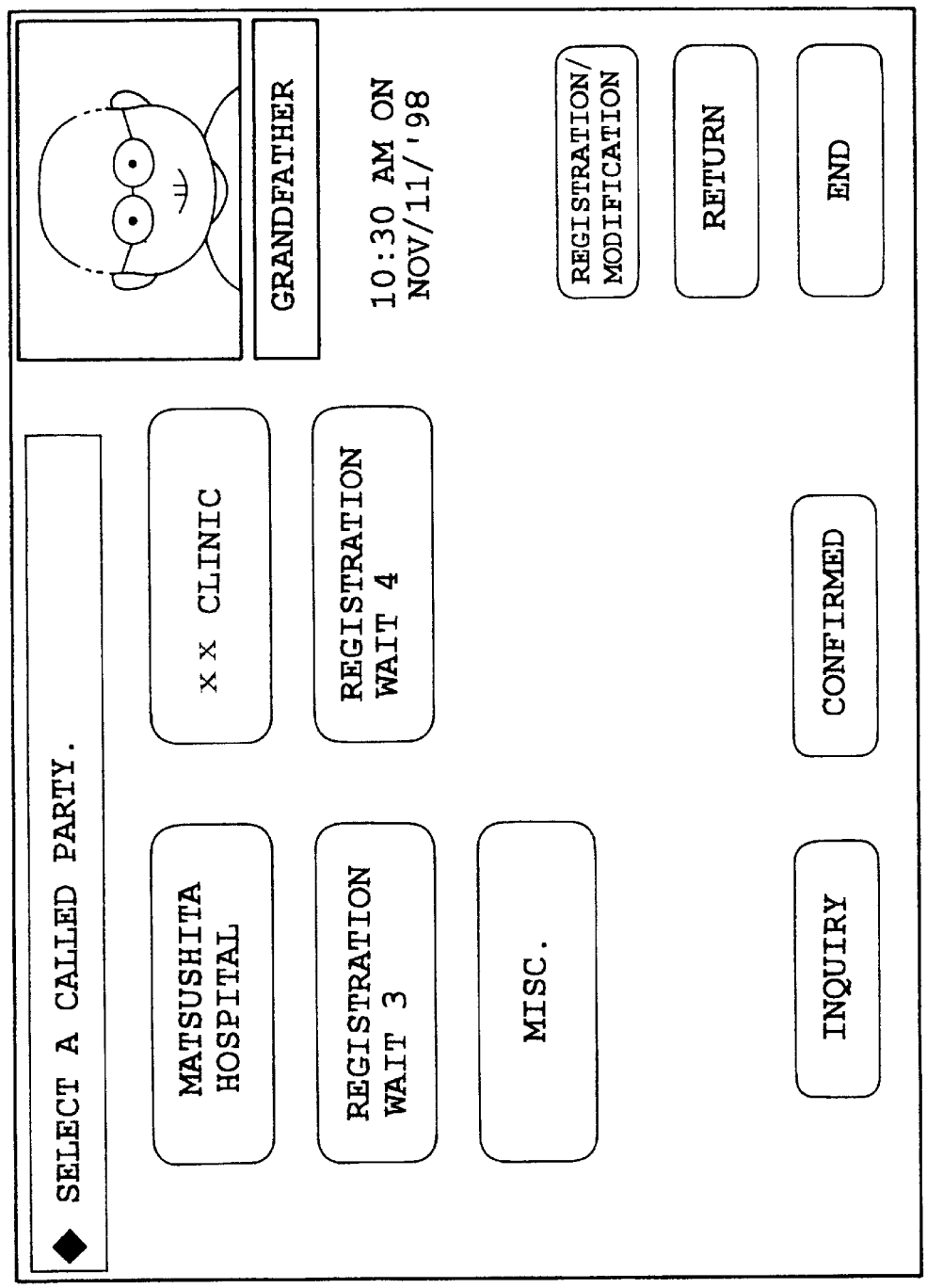
FIG. 25 is a drawing showing a display screen for letting a user input a name and a telephone number of a communication partner in order to specify the communication partner of the vital sign box according to the first embodiment of the present invention.

It is assumed that, when the contents shown in FIG. 9 are next displayed in the display 10, the user is going to communicate with the personal computer connected to the vital sign box via a communications line. At this time, the user touches a "Telephone" portion in the display 10, and the display 10 displays and blinks the "Telephone" portion when the "Telephone" portion is touched, and after that, changes the display contents to the contents shown in FIG. 25. FIG. 25 is a drawing showing a display screen for letting a user input a name and a telephone number of a communication partner in order to specify the communication partner of the vital sign box. When the display 10 displays the contents shown in FIG. 25, the user touches any one of "Matsushita Hospital," "xx clinic," "Registration wait 3," and "Registration wait 4," and "Misc." portions. By the way, the display of the "Matsushita Hospital" and "xx clinic" means that names and telephone numbers of the "Matsushita Hospital" and "xx clinic" have been already registered. Furthermore, the display of the "Registration wait 3," "Registration wait 4" and "Misc." means that names and telephone numbers of communication partners have not been registered yet.

Figure 26:
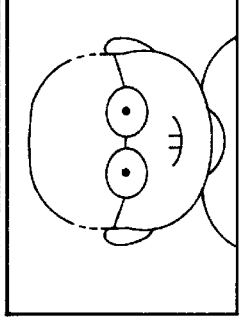
FIG. 26 is a drawing showing inquiry items that are displayed in the display 10 included in the vital sign box according to the first embodiment of the present invention, and about which a user is asked.

Then, if a communication partner is the "Matsushita Hospital" or "xx clinic" and the name and telephone number have been registered beforehand, the user touches the concerned portion. When the concerned portion is touched, the display 10 displays inquiry items to the user as shown in FIG. 26. The user replies to the inquiry items shown in FIG. 26, and when the answer is finished, the user touches a "Confirmed" portion. In addition, the display 10 is used as an inquiry result input unit of the present invention according to claim 27. By the way, when the contents shown in FIG. 26 is displayed in the display 10 and the "Confirmed" portion is touched by the user, the vital sign boxs communicates with the communication partner through the communication terminal 13, and the display in the display 10 goes to the next step shown in FIG. 29. On the other hand, if the communication partner is not the "Matsushita Hospital" or "xx clinic" and its name and telephone number are not registered, the user touches any one of the "Registration wait 3," "Registration wait 4," and "Misc." portions. If considering to contacts many times to a specific communication partner in future, the user touches the "Registration wait 3" or "Registration wait 4" portion, or if not, the user touches the "Misc." portion. If the user touches the "Registration wait 3" or "Registration wait 4," the display 10 displays the contents shown in FIG. 27 to let the user register a name and a telephone number of the communication partner with letting the user utilize the touch panel. If the user touches the "Confirmed" portion after the registration, the vital sign box contacts to the communication partner through the communication terminal 13, and the display 10 displays the contents at the next step. In this manner, by letting a user register a name and a telephone number of a communication partner, thereafter, the name and telephone number are associated with the "Registration wait 3" or "Registration wait 4" that is shown in FIG. 25 and touched before the registration of the name and telephone number, and are managed by the vital sign box. On the other hand, if the user touches the "Misc." portion when the display 10 displays the contents shown in FIG. 25, the display 10 displays the contents shown in FIG. 28 to let the user input a telephone number of a communication partner with letting the user utilize the touch panel. If the user touches the "Confirmed" portion after the input, the vital sign box contacts to the communication partner through the communication terminal 13, and the display 10 displays the contents at the next step.

In addition, as explained at the time of describing the configuration of an vital sign box of a first embodiment of the present invention, for the convenience of the following explanation, it is assumed that the communication partner of the vital sign box is the "Matsushita Hospital."

Moreover, although the contact method to a communication partner only by the display in the display 10 is explained in the above description, it is assumed that the contact method to the communication partner is explained simultaneously with using sound from the speaker 11. In this manner, as described above, also in the following explanation, it is assumed that the usage of the vital sign box is explained not only with the display in the display 10, but also with a sound output from the speaker 11.

Figure 29:
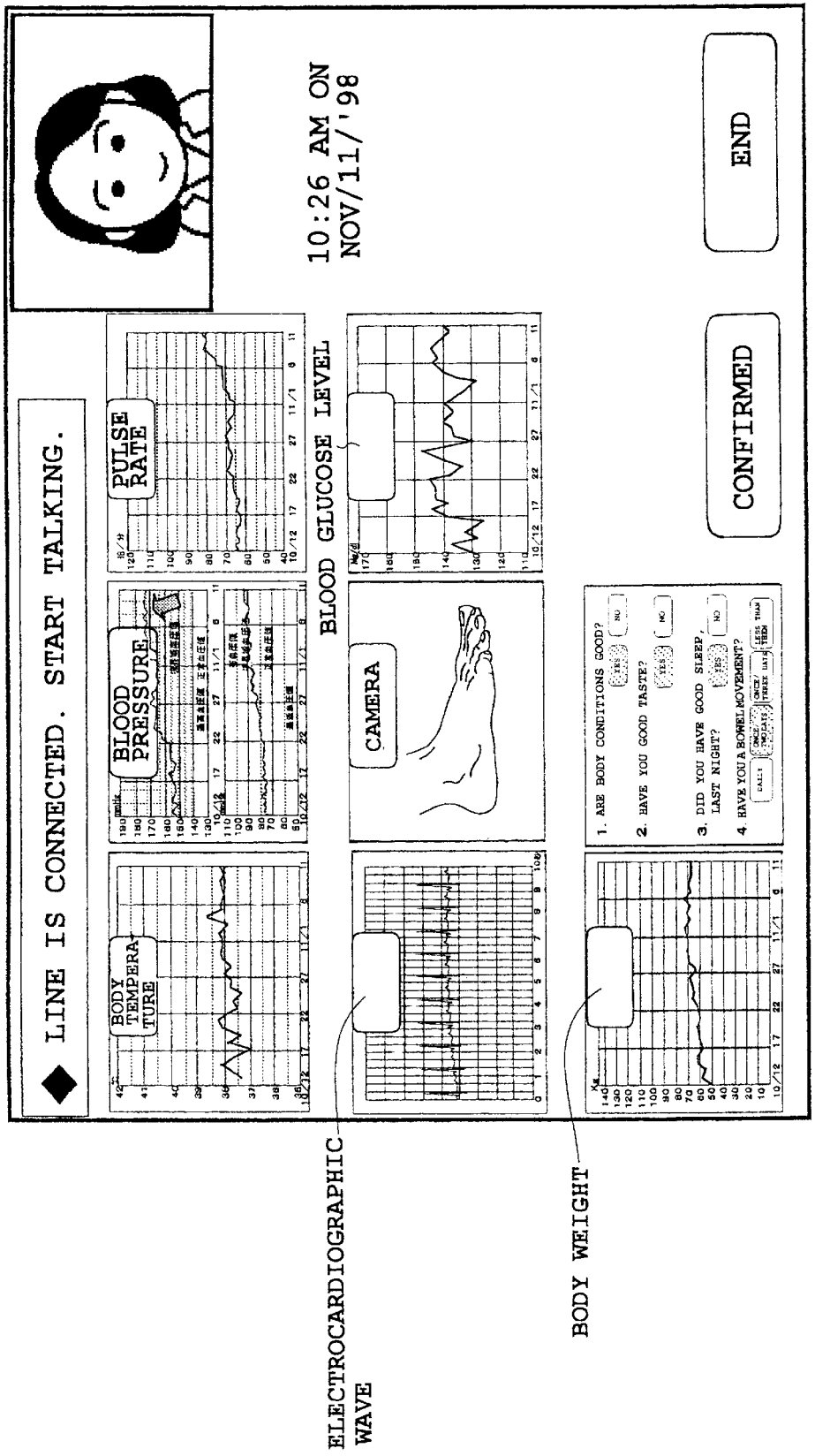
FIG. 29 is a drawing showing a display screen first displayed in the display 10 of the vital sign box and a personal computer of a communication partner after the vital sign box according to the first embodiment of the present invention and the personal computer of the communication partner could communicate with each other.

By the way, it is assumed that a user of the vital sign box is a "Grandfather," a communication partner of the vital sign box is the "Matsushita Hospital," and the vital sign box can communicate with the personal computer in the "Matsushita Hospital" on the basis of the contact from the vital sign box. In the display 10 of the vital sign box, as shown in FIG. 29, data, which relates to the "Grandfather," is measured by each vital sensor, and is graphed, among data stored in the memory 9, newest images taken by the camera 5, data that is measured by the scale and graphed, and the inquiry result are displayed separately with sharing an display area. Each graph in FIG. 29 is different from each graph shown in FIG. 11, and is obtained by graphing values that are shown in FIGS. 13, 15, 17, 18, 19, 22, and 24 and are actually measured. In addition, when displaying the contents shown in FIG. 29, the display 10 displays that the vital sign box becomes communicable with the personal computer in the "Matsushita Hospital" that is the communication partner. Furthermore, the speaker 11 also outputs by sound that the vital sign box becomes in the status of being able to communicate. In addition, at that time, the vital sign boxs inputs a face image of a doctor in the "Matsushita Hospital," which is taken by a camera connected to the personal computer, from the personal computer of the communication partner through the communication terminal 13. Then, the display 10 displays the doctor's image in the top right portion of the screen. In addition, the vital sign boxs transmits data displayed in the display 10 to the personal computer of the communication partner through the communication terminal 13, and lets the contents, which are shown in FIG. 29 and displayed in the display 10, displayed on a screen of the personal computer. Furthermore, the "Grandfather" who is a user of the vital sign box lets the camera 5 take a picture of the user's own face with fixing an angle of gradient of camera 5 at a predetermined angle. The vital sign box transmits the user's real time image, taken by the camera 5, to the personal computer of the communication partner through the communication terminal 13. In addition, at that time, the microphone 12 becomes in a status that the microphone 12 can collect sonic reflection of realtime voice of the "Grandfather," and can transmit the voice to the personal computer of the communication partner through the communication terminal 13. Furthermore, the display 10 becomes in a status that the display 10 can input information from the communication partner through the communication terminal 13 and can display the information. Moreover, the speaker 11 becomes in a status that the speaker 11 can input information such as the voice of the doctor in the communication partner through the communication terminal 13 and can output the information as sound. In this manner, by also using the vital sign box as a picture phone, the "Grandfather" that is a user of the vital sign box receives telemedicine from the doctor in the communication partner.

Figure 30:
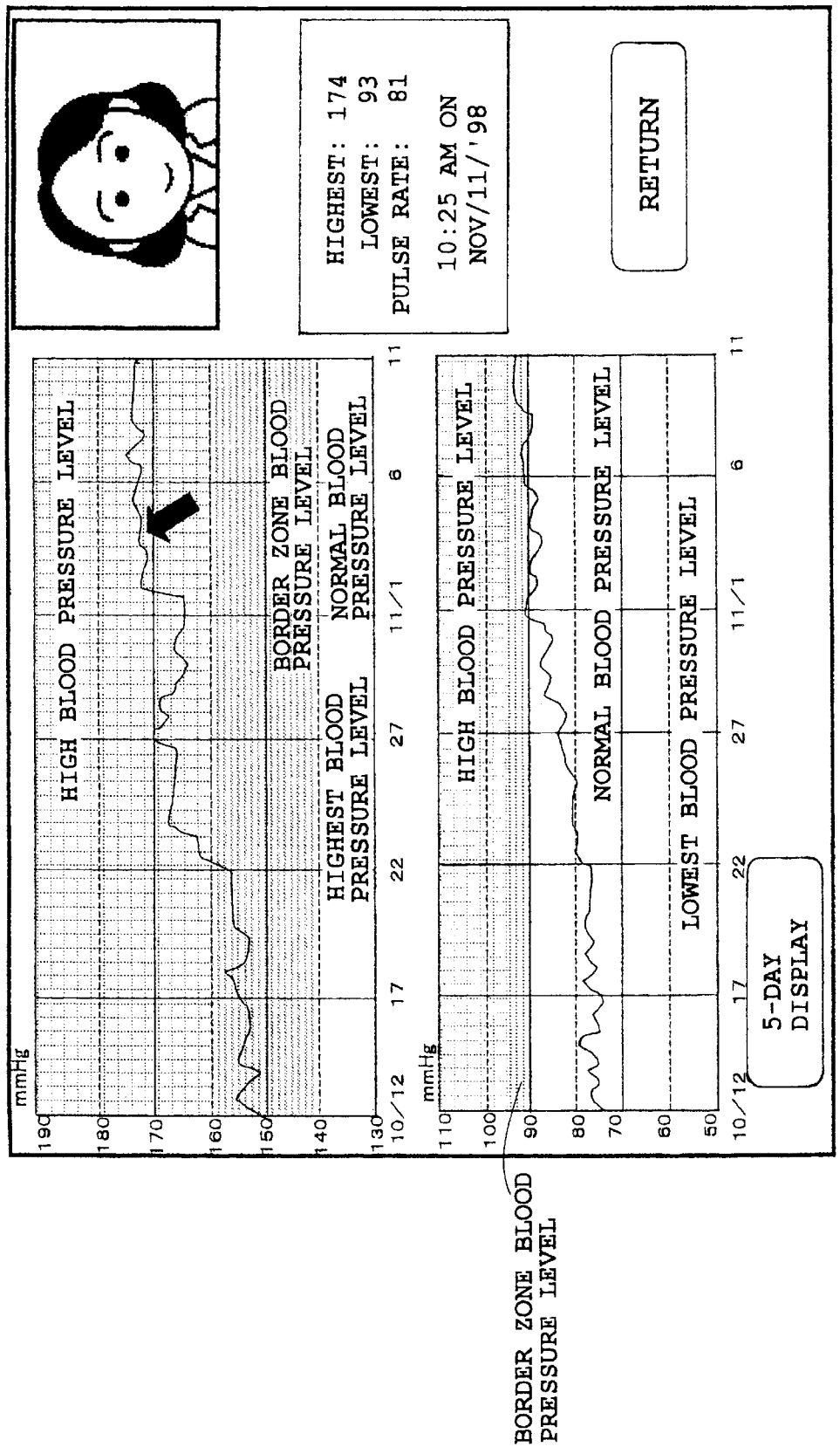
FIG. 30 is a drawing showing a display screen where an arrow is displayed in the display 10 of the vital sign box and the personal computer of the communication partner while the vital sign box according to the first embodiment of the present invention and the personal computer of the communication partner are communicating.

In addition, suppose that, when the "Grandfather" that is a user of the vital sign box receives telemedicine from the doctor in the communication partner, the doctor observes, for example, a graph of blood pressure in a screen of the personal computer and finds an abnormal indication. Then, when the doctor controls the screen to magnify only the graph in order to pay attention to the graph, not only the graph of blood pressure is magnified on the screen of the doctor's personal computer, but also the graph of blood pressure is magnified and displayed in the display 10 of the vital sign box by the zoom control being inputted into the vital sign box through the communication terminal 13. Furthermore, when the doctor locates an arrowhead on the graph as shown in FIG. 30 in order to specify the abnormal point, coordinate information of the arrowhead is inputted into the vital sign box through the communication terminal 13 from the doctor's personal computer. Hence, also on the graph of blood glucose level in the vital sign box, an arrowhead is displayed in a location that substantially corresponds to the location that the doctor specifies. In this manner, the above-described arrowhead is utilized as, for example, an arrowhead for informed consent. By the way, since the display 10 stores shape information of an arrowhead to be displayed, it is possible to display the arrowhead by not only being based on the coordinate information of the arrowhead from the doctor's personal computer, but also utilizing the shape information of the arrowhead stored.

Up to here, for the description of communication between the vital sign box and the doctor's personal computer, an example of communication is explained with using the graphs of blood pressure shown in FIGS. 29 and 30. Nevertheless, the communication between the vital sign box and the doctor's personal computer is not limited to the application of the graph of blood pressure shown in FIG. 29. Thus, other graphs and data shown in FIG. 29 are also used similarly to the graph of blood pressure shown in FIG. 29, and the information of images and/or sound is exchanged between both parties.

Figure 31:
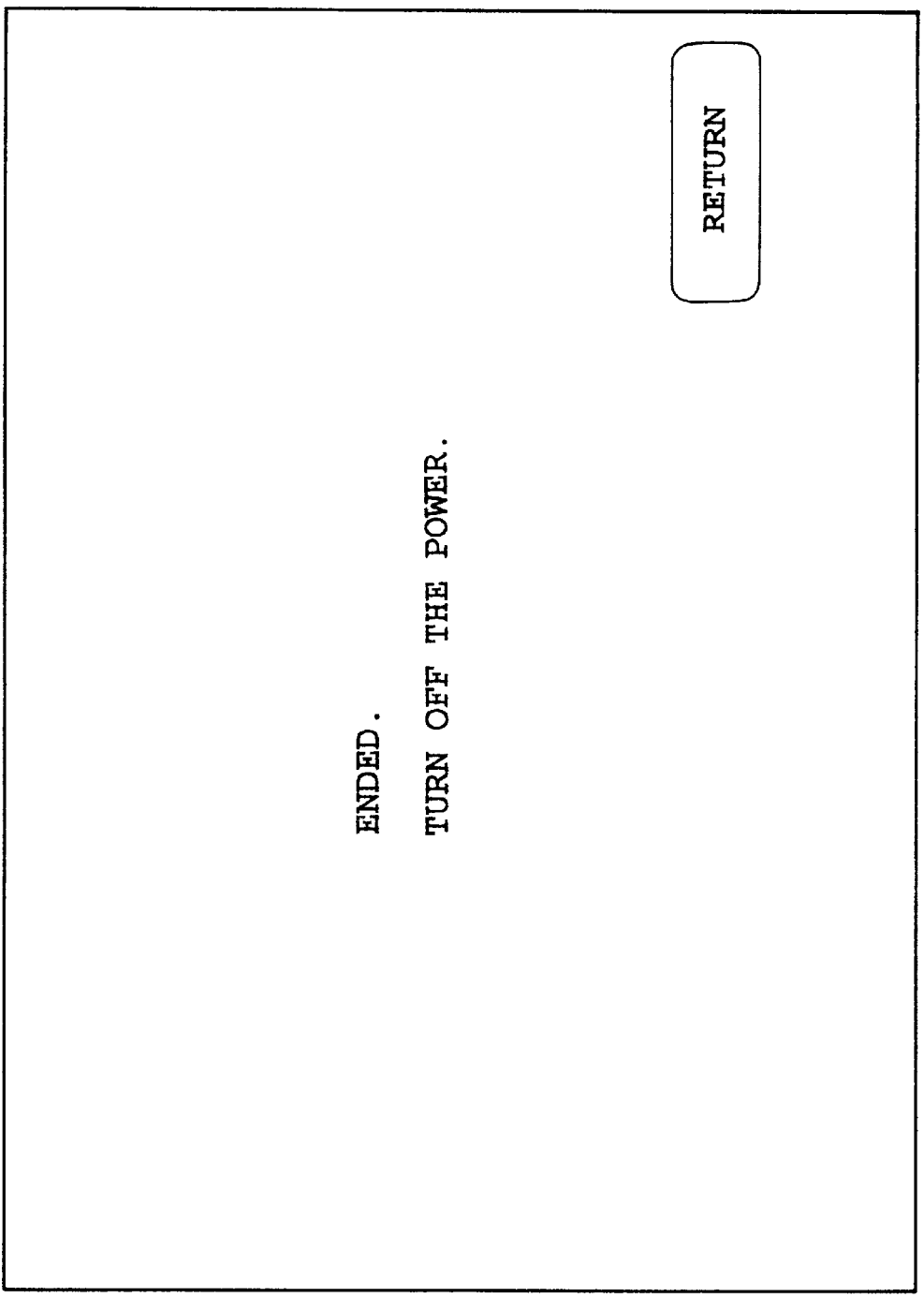
FIG. 31 is a drawing showing a display screen that is displayed in the display 10 of the vital sign box according to the first embodiment of the present invention and is displayed for instructing a user to turn off the vital sign box.

Then, when the user of the vital sign box finishes communication with the communication partner, the user touches an "End" portion displayed in the display 10 at that time when the contents shown in FIG. 29 is displayed in the display 10, and changes the display of the display 10 to the contents shown in FIG. 9. On the other hand, if the display contents in the display 10 at the time of finishing communication is the contents shown in FIG. 30, the user touches the "Return" portion displayed in the display 10 to let the display 10 display the contents shown in FIG. 29, and touches the "End" portion to change the display in the display 10 to the contents shown in FIG. 9. In any case, if the contents shown in FIG. 9 are displayed in the display 10, the user next touches the "End" portion shown in FIG. 9. In this manner, when the "End" portion shown in FIG. 9 is touched, the display 10, as shown in FIG. 31, displays information to instruct the user to finish the use of the vital sign box and turn off the vital sign box, and lets the user to turn off the vital sign box.

In addition, in the above-described first embodiment, the base 6 is rotatable, and not only can be fixed at a predetermined angle, but also is means of containing the camera 5, and the camera 5 is detachable from the base 6. Nevertheless, it can be also performed that, without providing the base 6 in the vital sign box, the camera 5 is rotatable with connecting to the housing 14 and can be fixed at a predetermined angle.

Figure 32:
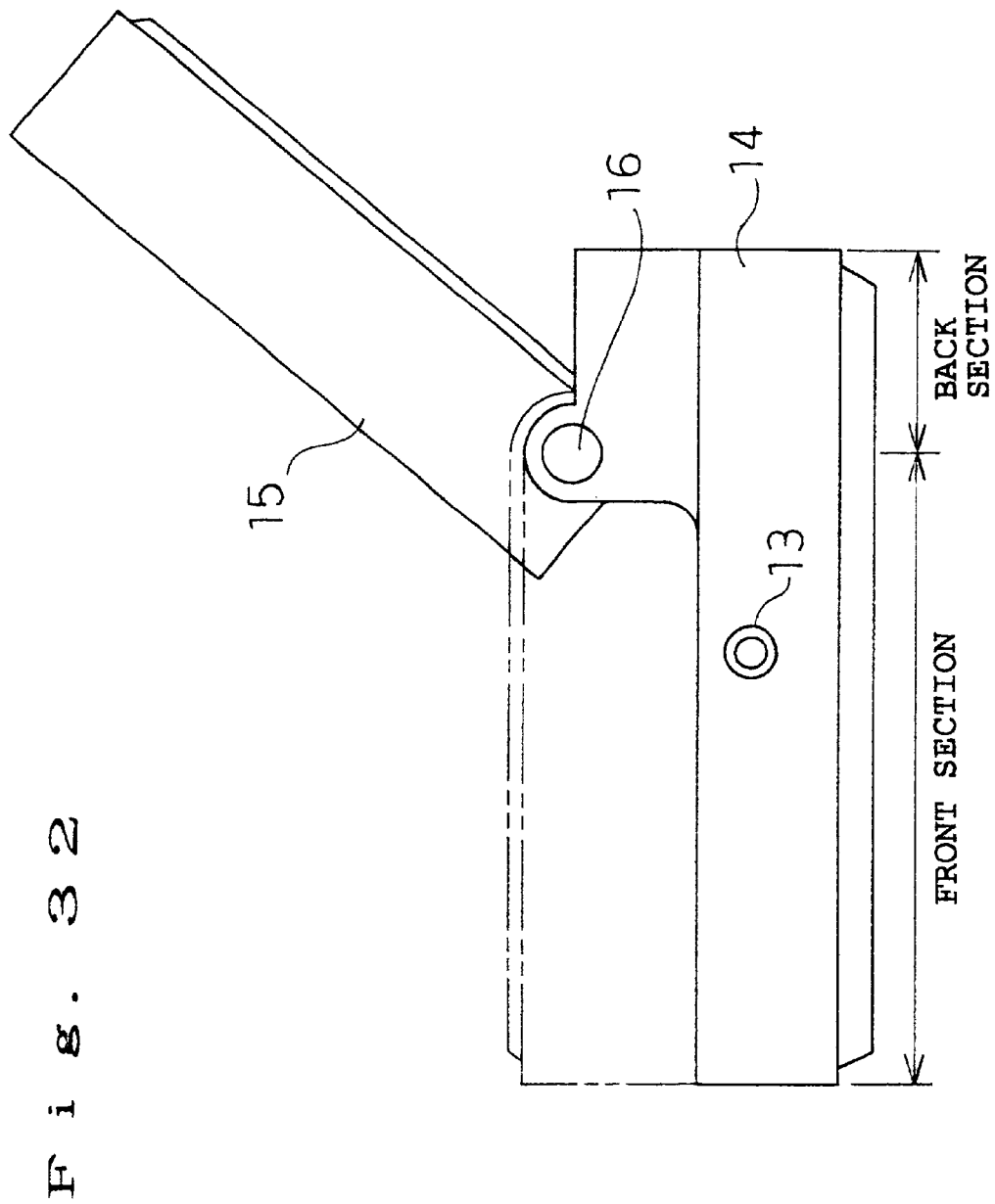
FIG. 32 is a side view of an vital sign box when a lid of the vital sign box according to the first embodiment of the present invention is opened, which is different from the vital sign box shown in FIG. 2.

In addition, in the above-described first embodiment, the lid 15 of the vital sign box, as shown in FIG. 2, is provided through the shank 16 substantially in one edge side of an upper surface of the main body of the housing 14. In such a structure, there is a possibility of causing such an unstable status that, as shown in FIG. 2, when the lid 15 is let to be vertical to the bottom face of the vital sign box, mainly because of the weight of the display 10 inside the lid 15, the lid 15 falls down to the side where the shank 16 of the housing 14 is provided, and in connection with it, the main body of the housing 14 rises with one side of the bottom section of the housing 14, which faces to the shank 16, as a substantial shaft. Then, in order to solve such structural instability, it can be also performed in regard to the structure of the vital sign box that the shank 16, as shown in FIG. 32, is located so that the main body of the housing 14 is divided into a front section and a rear section, the lid 15 is provided through the shank 16, and the display 10 is provided inside the lid 15 with letting the lid 15 be fixed in a status that the lid 15 is vertical to the bottom section of the vital sign box with using the shank 16 at the time of using the vital sign box. In this manner, if the main body of the housing 14 has the front section and rear section to the shank 16, it is possible to avoid the unstable status that the main body of the housing 14 rises when the lid 15 is let to be vertical to the bottom section of the vital sign box.

In addition, in order to solve the structural problems that are described above and depends on a mounted location of the lid 15 of the housing 14 as shown in FIG. 2, it can be also performed that the display 10 provided inside the lid 15 is thinned and lightened.

Figure 33:
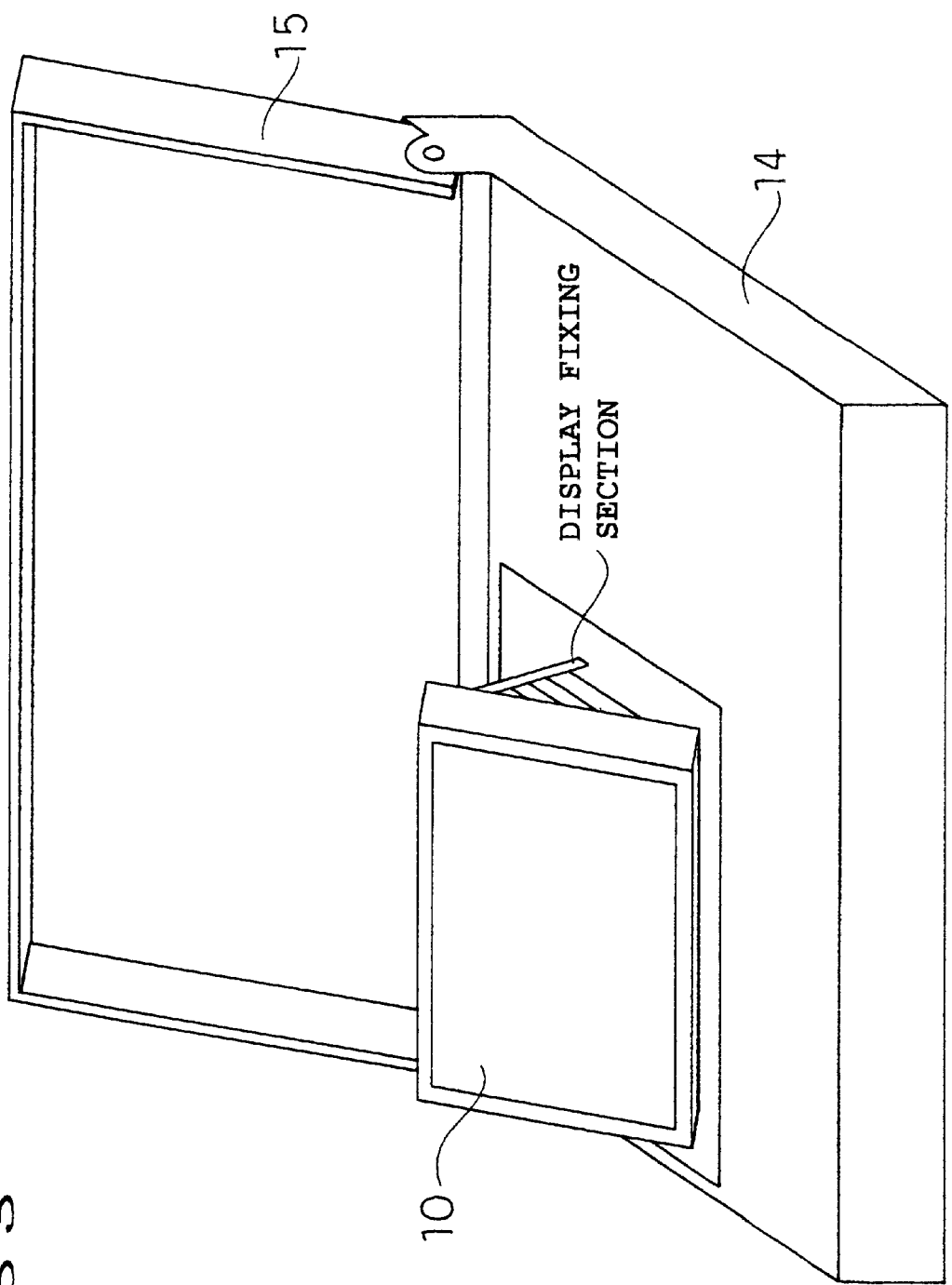
FIG. 33 is a side view of an vital sign box when a lid of the vital sign box according to the first embodiment of the present invention is opened, which is different from each vital sign box shown in FIGS. 2 and 32.

Furthermore, in order to solve the above-described structural instability depending on a mounted location of the lid 15 of the housing 14 as shown in FIG. 2, instead of providing the display 10 inside the lid 15, it can be also performed that, as shown in FIG. 33, the display 10 is made to be movable so that the display 10 can be contained in the main body of the housing 14 in a condition that the display 10 lies in a bottom section of the main body of the housing 14 at the time of non-use, and can be fixed in a condition that the display 10 is vertical to the bottom of the main body of the housing 14 at the time of use. Moreover, it can be also performed that, so as to fix the display 10 in a condition that the display 10 is vertical to the bottom section of the housing 14 at the time of using the display 10, a fixing section of the display 10 is provided in the main body of the housing 14.

Figure 34:
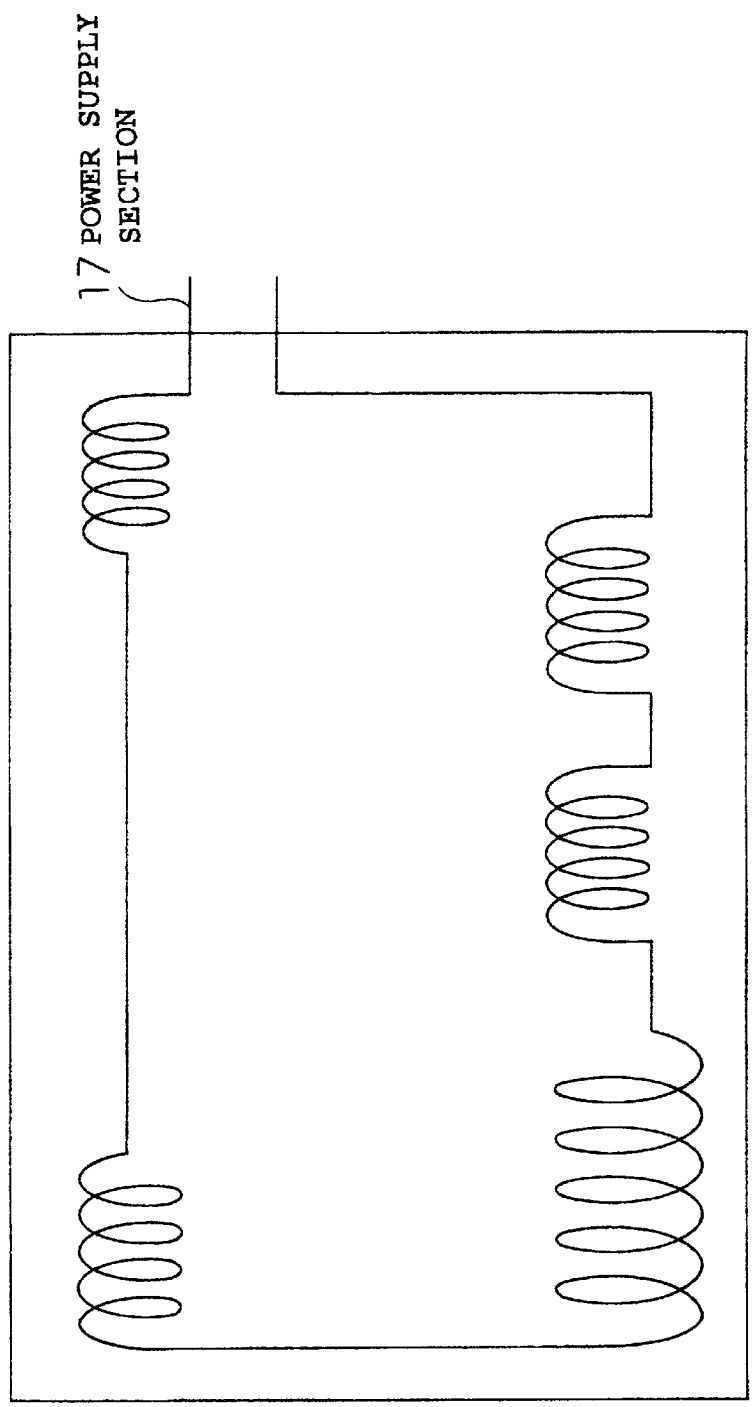
FIG. 34 is a configuration of a power supply section 17 supplying electric power to each vital sensor and the camera 5 of the vital sign box according to the first embodiment of the present invention with using an electromagnetic wave generated by electromagnetic induction.
Figure 35:
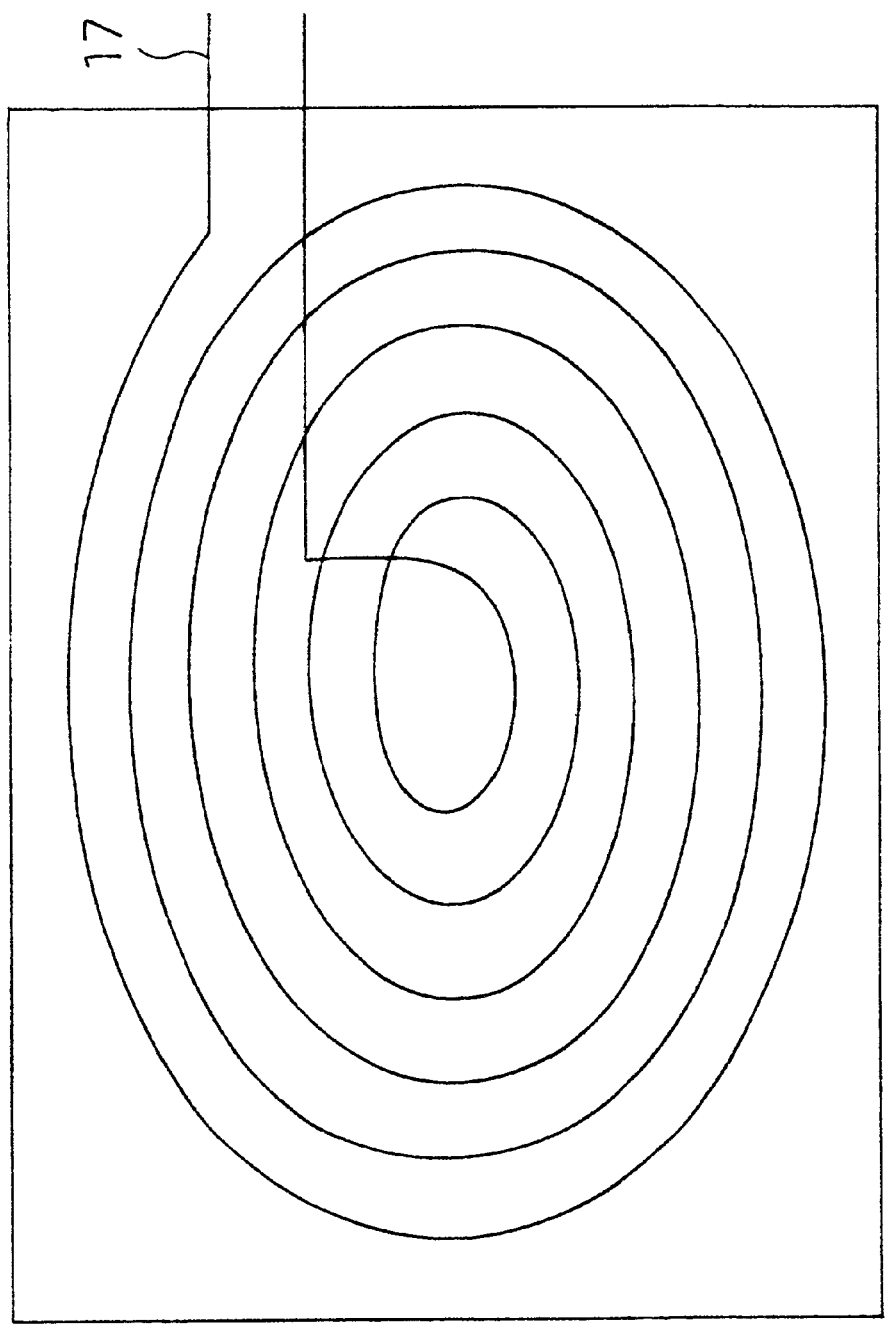
FIG. 35 is a configuration of another power supply section 17 supplying electric power to each vital sensor and the camera 5 of the vital sign box according to the first embodiment of the present invention with using an electromagnetic wave generated by electromagnetic induction, which is different from the power supply section 17 in FIG. 34.
Figure 36:
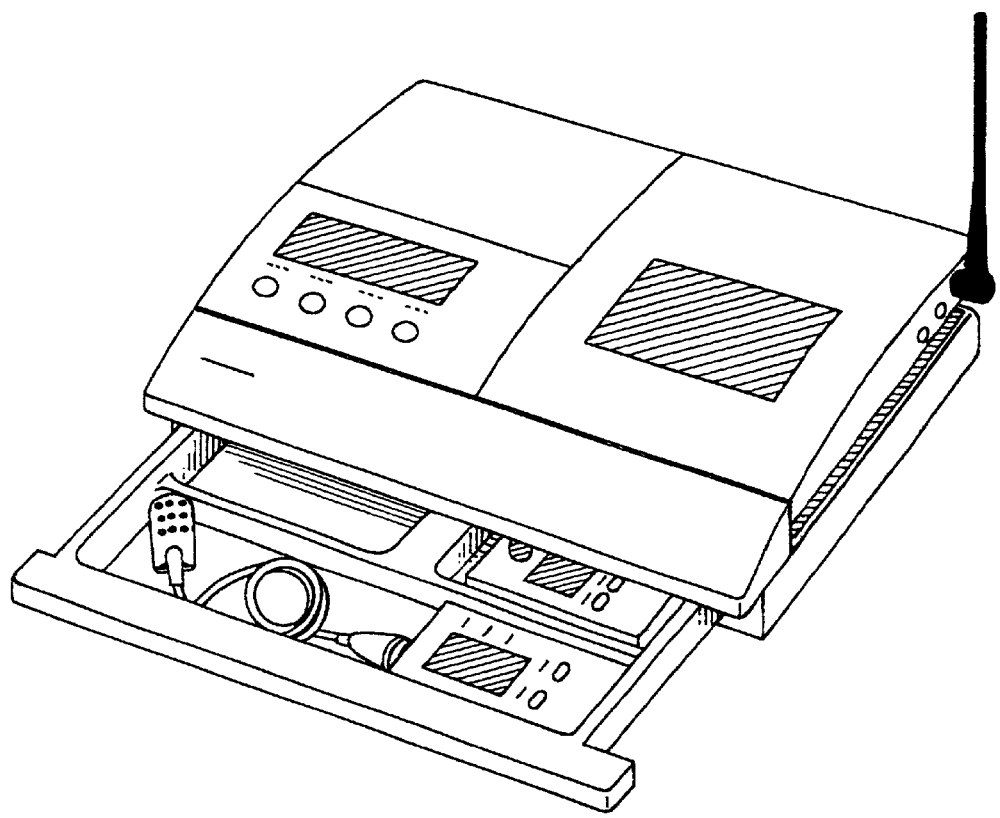
FIG. 36 is a perspective view showing a conventional vital sign box used in Medi Data that is an online medical check system developed by SECOM Co., Ltd./SECOM home medical care system Co., Ltd.

In addition, although each driving power supply of the respective vital sensors and camera 5 is not explained in the above-described first embodiment, it can be performed that, by mounting each battery in the respective vital sensors and camera 5, the respective vital sensors and camera 5 are driven by electric power from the batteries respectively. Alternatively, it can be also performed that, by supplying electric power to the respective vital sensors and camera 5 with using the following method, the respective vital sensors and camera 5 are driven by the electric power. Thus, as shown in FIG. 34, for example, it is such a structure that a power supply section 17 is provided in the bottom of the housing 14 of the vital sign box, the power supply section 17 which consists of a predetermined conductive wire that is configured lest the conductive wire should contact to each vital sensor and the camera 5 and further supplies electric power from the outside of the vital sign box to each vital sensor and the camera 5 with using an electromagnetic wave by electromagnetic induction. In addition, the power supply section 17 is provided inside the main body of the housing 14 so that the power supply section 17 becomes substantially in parallel to the bottom face of the main body of the housing 14. In this case, as shown in FIG. 34, a shape of the power supply section 17 in a position corresponding to each housing location at the time of each vital sensor and the camera 5 being housed in the housing 14 is made to be a winding wire shape. Furthermore, each electric power storage section storing the electromagnetic wave from the power supply section 17 as electric power is provided in each vital sensor and the camera 5. Moreover, with using an electromagnetic wave by electromagnetic induction from each winding wire section by applying the current to the power supply section 17 from the outside of the vital sign box external when electric power is supplied to each vital sensor and the camera 5, the electric power is supplied to each vital sensor and the camera 5. In this way, it becomes not necessary to mount each battery in each vital sensor and the camera 5. By the way, it can be also performed that, for example, instead of such a structure that each winding wire section is provided only in the specific location as shown in FIG. 34, the power supply section 17 provided in the bottom section of the housing 14 is configured by a predetermined conductive wire whose entire shape is a winding wire shape. In brief, the power supply section 17 is sufficient so long as the power supply section 17 does not contact to each vital sensor and the camera 5, and supplies electric power from the outside of the vital sign box to each vital sensor and the camera 5 with using an electromagnetic wave by electromagnetic induction. In addition, it is not always necessary to supply electric power with using an electromagnetic wave by above-described electromagnetic induction to all of the vital sensors and camera 5, but it is also good to supply the electric power to part of the vital sensors and camera 5.

Furthermore, in the above-described first embodiment, it is assumed that the display 10, as shown in FIG. 26, displays inquiry items to a user of the vital sign box just before the vital sign box and the personal computer of the "Matsushita Hospital" or "xx clinic" can communicate with each other. Nevertheless, the display of the inquiry items to a user by the display 10 is not limited to the display performed just before communication. For example, the display of the inquiry items to a user by the display 10 can be performed after the vital sign box and personal computer of the "Matsushita Hospital" or "xx Clinic" can communicate with each other. In brief, the display 10 of the vital sign box according to the first embodiment of the present invention is sufficient so long as the display 10 displays the inquiry items to a user.

Moreover, in the above-described first embodiment, although it is assumed that inquiry items to a user of the vital sign box are displayed by the display 10, the inquiry can be also performed with using sound from the speaker 11. The inquiry to a user of the vital sign box with using sound, similarly to the display by the display 10, can be also performed in any timing. By the way, if the inquiry items are outputted with using sound, it becomes necessary to provide an inquiry result input section, into which the user inputs answers to the inquiry items, in the vital sign box. It is possible to use, for example, the display 10 as the inquiry result input section. In addition, it is made to provide a communication terminal for transmitting answers to inquiry items, which the inquiry result input section inputs, to a communication partner. As the communication terminal, for example, the communication terminal 13 can be also used. In addition, by also using the communication terminal to be used so as means of inputting information from a communication partner, it can be performed not only to let the display 10 display the information from the communication partner, but also to let the speaker 11 output the information from the communication partner with using sound. Nevertheless, the information from the communication partner can be also outputted with using one out of the display 10 and speaker 11.

In addition, in the above-described first embodiment, although it is made that the usage of the vital sign box is outputted by the display performed by the display 10 and by sound from the speaker 11, the usage of the vital sign box can be also performed by any one of the display by the display 10 and the sound from the speaker 11. Furthermore, if the usage of the vital sign box is output only by sound from the speaker 11, a change instruction input section for inputting an instruction from a user can be also provided in the vital sign box so that an output method of the usage is changed to the display by the display 10.

Moreover, in the above-described first embodiment, as described at the time of describing the configuration of the vital sign box according to the first embodiment of the present invention, the electrocardiograph 1, blood pressure monitor 2, earhole clinical thermometer 3, and blood glucose meter 4 are used as an example of vital sensors in the vital sign box of the present invention according to each of claims 1, 11, 13, 15, 17, 20, 21, 25 and 26. Nevertheless, the vital sensors that are provided in the vital sign box of the present invention according to each of the above-described claims are not limited to the electrocardiograph 1, blood pressure monitor 2, earhole clinical thermometer 3, and blood glucose meter 4. All of the electrocardiograph 1, blood pressure monitor 2, earhole clinical thermometer 3, and blood glucose meter 4 can be provided in the vital sign box of the present invention, or only the part of them can be also provided. In addition, for example, other vital sensors such as a blood oxymeter measuring blood oxygen concentration can be also provided.

In addition, in the above-described first embodiment, as shown in FIG. 11, it is made that the usage of the vital sign box is displayed in graphic images of measurements measured by respective vital sensors, images taken by the camera 5, a graphic image of measurements measured by the scale, and letters. Nevertheless, the usage of the vital sign box can be displayed only in graphic images of measurements measured by respective vital sensors, images taken by the camera 5, and a graphic image of measurements measured by the scale, or can be also displayed only in letters. Furthermore, only the images, only the letters, or images combined with letters can be also used and displayed every screen. Moreover, although each graph in FIG. 11 is made to be a graphic image of measurements measured by each vital sensor, if a user's data has been already stored in the memory 9 at that time, a graph of the data stored can be also used as each graph in FIG. 11. In addition, also as for an image to be taken by the camera 5, if a user's image has been already stored in the memory 9 at that time, the memory can be also substituted by the image stored.

Furthermore, in the above-described first embodiment, it is made that a measurement measured by each vital sensor is displayed in the display 10 with using a number of the measurement or in a transition graph of measurements for last 5 days or 30 days including the measurement. In addition, it is made that a measurement is also outputted from the speaker 11 by sound. However, a measurement measured by each vital sensor can be also displayed only in a number in the display 10, or can be also displayed only in a graph in the display 10. Moreover, only sound can be also outputted from the speaker 11. Furthermore, the display of only a number in the display 10 and an output by sound from the speaker 11 can be also performed. Alternatively, the display of only a graph in the display 10 and an output by sound from the speaker 11 can be also performed.

In addition, in the above-described first embodiment, it is made that, for example, as shown in FIGS. 12, 13, and 14, a measurement measured by each vital sensor is displayed in the display 10 as a transition graph of measurements for 5 days or 30 days including the measurement. However, in the display 10, a transition graph of measurements for the last 10 days can be also displayed without displaying the transition graph showing the measurements for 5 days or 30 days. In brief, a graph displayed in the display 10 is sufficient so long as the graph shows the transition of measurements in a predetermined period. Moreover, by providing means of a user inputting, for example, an instruction for specify the period in the vital sign box, it is also possible to let the display 10 change the period according to the instruction each time a graph is displayed.

In addition, in the above-described first embodiment, for example, as shown in FIGS. 12 and 13, when measurements measured by each vital sensor are displayed on the display 10 as a graph so as to show the transition during the last 5 days or 30 days, a display range is determined with a final measurement as a reference. Nevertheless, the display range can be also determined by letting a mean value of measurements in a period to be displayed be a reference, and defining the period be a range between predetermined higher value and lower value than the value that is the reference.

Moreover, in the above-described first embodiment, as shown in FIGS. 12 and 14, it is made that the display 10 displays and blinks a final measurement in a 5-day graph of measurements when displaying the graph of measurements measured by each vital sensor. On the other hand, it can be also performed that the display 10 displays and blinks the final measurement when displaying a 30-day graph of measurements, or that the display 10 displays and does not blink the final measurement.

Furthermore, in the above-described first embodiment, a communication partner of the vital sign box is the "Matsushita Hospital." Nevertheless, the contents, first displayed in the display 10 when the vital sign box can communicate with another communication partner, is not limited to the contents shown in FIG. 29. It is also good to display some one except inquiry items among contents shown in FIG. 29, or to display only a message that the vital sign box becomes communicable with a communication partner. In brief, this means that, if a communication partner of the vital sign box is not the "Matsushita Hospital," when the vital sign box becomes communicable, the contents displayed in the display 10 are not limited.

In addition, in the above-described first embodiment, it is made that, when the vital sign box becomes communicable with a personal computer of the "Matsushita Hospital" that is a communication partner of the vital sign box, a latest image taken by the camera 5 is displayed in FIG. 29 displayed in the display 10. Nevertheless, so long as the image is an image taken by the camera 5, it is not necessary to display the latest image in the display 10 displaying the contents shown in FIG. 29. For example, it is also good to display an image to be selected by letting a user select beforehand the image to be displayed. Furthermore, it is also good that, if image data is not stored in the memory 9, an image taken by the camera 5 is displayed.

Moreover, in the above-described first embodiment, although it is assumed that a communication partner of the vital sign box is "Matsushita Hospital," it is also good that the communication partner is, for example, a personal computer of a relative who lives apart from the "Grandfather" who is a user of the vital sign box. In that case, it is also possible to use the camera 5 in the vital sign box as means of taking a realtime picture of the "Grandfather" that is a user, or as a picture phone for performing communication with the relative.

In addition, in the above-described first embodiment, although a communication partner of the vital sign box is a personal computer of the "Matsushita Hospital." The communication partner of the vital sign box is not limited to a personal computer so long as the partner can communicate with the vital sign box via a communication line such as a telephone line. For example, by connecting two vital sign boxs with each other via a communication line, both vital sign boxs can communicate with each other, and hence it is also possible to use the partner's vital sign box as an alternative of a personal computer. Furthermore, it is also possible to use both vital sign boxs as alternatives of picture phones.

Moreover, in the above-described first embodiment, it is made that it may happen that, when the vital sign box becomes communicable with a personal computer of the "Matsushita hospital" that is a communication partner, as shown in FIG. 30, arrowhead information for displaying an arrowhead in a graph is transmitted from the personal computer to the vital sign box. In addition, in that case, it is made that the arrowhead information is coordinate information and the vital sign box displays the arrowhead on the basis of the coordinate information of the arrowhead from the personal computer by utilizing shape information of the arrowhead stored. However, it is also good that arrowhead information transmitted from the personal computer to the vital sign box is coordinate information and shape information, and the arrowhead is displayed in a predetermined position by decoding the arrowhead from the shape information by the vital sign box and further using the coordinate information. However, in this case, an amount of information of the arrowhead information from the personal computer to the vital sign box increases in comparison to a case of only the coordinate information.

Furthermore, in the above-described first embodiment, although it is described that the vital sign box is operated by a user himself/herself, a user of the vital sign box can be a person, who assists a patient who cannot operate the vital sign box by oneself, such as a family member of a bedridden home health care patient or a visiting nurse.

Moreover, in the above-described first embodiment, although it is made that the display 10 is a touch panel type liquid crystal display, the display. 10 can be a CRT display. In brief, it is good that the display 10 is a display just displaying each measurement measured by each vital sensor such as the electrocardiograph 1 and the blood pressure monitor 2, an object taken by the camera 5, the usage of the vital sign box, and the like. In addition, it is better that the display changes display contents when a predetermined portion is touched.

In addition, in the above-described first embodiment, it is made that, for example, as described in FIG. 6, when a predetermined portion such as the "Grandfather" in the display 10 is touched by a user, the portion touched is displayed and blinked. Nevertheless, it is also good that, when the predetermined portion in the display 10 is touched by the user, a color of the touched portion changes so that the touched portion is distinguished from other portion. In brief, it is sufficient only that, when a predetermined portion on the display 10 is touched by a user, the portion touched is displayed so that the portion is distinguished from the other portion.

Furthermore, in the above-described first embodiment, it is made that, if contents displayed in the display 10 are not change in a predetermined period, the measurement result of blood pressure and a pulse rate measured by the blood pressure monitor 2 are displayed with being mutually changed to an opponent measurement. Nevertheless, it is also good that, by providing switching means of changing the measurement result between blood pressure and a pulse rate, which is displayed in the display 10, in the vital sign box, the display 10 changes display contents when a user instructs the switching means. Moreover, it is also good to substitute the touch panel type display 10 for the switching means.

In addition, in the above-described first embodiment, it is made that a user presses a switch, which is provided in the camera 5, for recording an image in the memory 9 when an image taken by the camera 5 is recorded in the memory 9. Nevertheless, recording means of recording an image in the memory 9 can be provided in the main body of the vital sign box. It is also good to substitute the touch panel type display 10 for the recording means. In brief, it is sufficient only that the recording means of recording an image taken by the camera 5 in the memory 9 is provide in the vital sign box.

In addition, if the display 10 in the above-described vital sign box is a touch panel type display and a software keyboard function shown in FIG. 7 is provided and displayed in the display 10, a merit that a user can input characters is created without connecting a keyboard to the vital sign box. The software keyboard function can be utilized for the above-described inquiry result input, and further can be used for inputting questions to a doctor.

Furthermore, in the above-described first embodiment, although it is made that an image to be recorded in the memory 9 is a static image, an image stored in the memory 9 can be a moving image.

Moreover, in the above-described first embodiment, it is made that the vital sign box receives data from a scale that is outside the vital sign box and can transmits a measured value to the vital sign box with using an infrared ray having a predetermined wavelength. But, it is also good that it is made that the vital sign box cannot receive data from such a scale. Alternatively, it can be performed that the vital sign box receives data from equipment, which is outside the vital sign box and can transmit a measurement to the vital sign box with using an infrared ray having a predetermined wavelength, besides a scale, and records and manages the measurement with data from each vital sensor.

In addition, in the above-described first embodiment, it is made that the vital sign box is used by any user among a "Grandfather," a "grandmother," "Registration wait 3," and "Registration wait 4," that are shown in FIG. 5, that is, a user having been already registered, or a user who is going to be registered from now on. Nevertheless, it can be performed to provide, for example, a function for making it possible for a house guest to an owner of the vital sign box, a one-time user, and the like, that is, a person, whose name and password are not registered, to use the vital sign box.

Furthermore, although the camera 5 in the vital sign box according to the above-described first embodiment is used, for example, for taking a picture of an arm injury, it is necessary to adequately adjust a focus at that time. Although fixed focus adjustment and automatic focus adjustment can be listed as the focus adjustment, it can be assumed that the camera 5 in this embodiment is a fixed focus type camera. If so, it is possible to make the camera be smaller, lighter, and cheaper than an automatic focusing type camera.

In this way, if the camera 5 is a fixed focus type camera like this, it is desirable to provide range-finding means, which is used for measuring the distance between an imaging object such as an arm injury and a predetermined section such as a lens of the camera 5, in the camera 5. The reason is because it is necessary to condense rays of light from the camera 5 to the imaging object and to adjust the focus.

By the way, it is possible to use a string-like body or a rod-like body, which is attached in a predetermined location such as a lens of the camera 5 and has predetermined length, as the above-described range-finding means. The length of the string-like body or rod-like body may be set in such a manner that in taking a picture of the imaging object, when the tip of the string-like body or rod-like body is brought into contact with the imaging object, the focus can be adjusted. For example, it is recommended that the length is 3 cm.

In addition, instruction receiving means such as a button for receiving an imaging instruction from a user, and imaging means of taking a picture of an imaging object when the imaging instruction is received are provided in the camera 5. It is made that the user takes a picture of the imaging object by performing the imaging instruction to the camera 5 through contacting an end of the above-described string-like body or rod-like body with the imaging object, and pressing the button at that time when the user is going to take a picture of the imaging object such as an arm injury. By performing this, it becomes possible to take a picture at a correct focus.

In addition, the range-finding means is not limited to the above-described string-like body or rod-like body, but it is possible to use means, which utilizes an electromagnetic wave such as an ultrasonic wave or an infrared ray, as the range-finding means. Concretely, means of emitting an electromagnetic wave such as an infrared ray and detecting means of detecting the electromagnetic wave such as an infrared ray reflected by an imaging object is provided in the camera 5. Further, the distance between the imaging object and a predetermined position such as a lens of the camera is measured from the result detected by the detecting means. At that time, if comparison result output means of comparing the measured distance with the predetermined distance that the imaging object can be adequately shot, and outputting the comparison result by a sound and an image is provided in the camera 5, a user can perform an imaging instruction by pressing a button when the imaging object is located in an appropriate focal position. For example, the result that it becomes possible to adequately take a picture of the imaging object by accessing the imaging object by 2 cm more corresponds to the comparison result. By performing so, it becomes possible to take a picture at a correct focus. In addition, it can be performed that the above-described comparison result output means outputs information as such by a sound or an image when the imaging object is located in an appropriate focal position.

Furthermore, if the distance between the imaging object and camera is measured with using an electromagnetic wave as described above, it can be performed that the imaging means automatically takes a picture of the imaging object when the detected distance is the distance that the imaging object can be shot adequately.

Moreover, it can be performed that at least part of the housing 14 of the above-described vital sign box consists of metallic material, and a connecting section that connects a heating section, which generates heat in connection with image display to a display, outputting of sound from a speaker, and information communication at a communication terminal, such as a CPU (central control processing unit) and an HDD (hard disk drive) that are housed in the housing 14, and a metallic material section of the above-described housing 14, and that consists of metallic material (for example, a copper wire) is provided in the vital sign box. Then, heat in the heating section can be discharged outside the vital sign box through the connecting section.

For example, if the body temperature of a human body is measured with a clinical thermometer contained in the vital sign box, it is necessary to keep the temperature of the clinical thermometer itself at about room temperature before measurement. Hence, by discharging heat in this way, the clinical thermometer is kept to be at about room temperature, and hence this has a merit that the clinical thermometer can be used effectively. In addition, even if the clinical thermometer is an actually measuring type clinical thermometer or a forecasting type clinical thermometer, the heat radiation effect is the same so long as the clinical thermometer is a device measuring body temperature electrically.

Furthermore, if heat radiation is neglected, it is conceivable that the measurement accuracy of a clinical thermometer deteriorates. Nevertheless, as described above, for example, by providing a connecting section consisting of a copper wire or the like, heat can be radiated with using heat transfer in the connecting section, and hence it becomes possible to suppress the temperature rise of the vital sign box. Moreover, in regard to an vital sign box, when sensor installation locations are designed, it is effective to arrange the vital sign box apart from a clinical thermometer.

Furthermore, a medium that bears a program and/or data for letting a computer execute all or part of functions of the above-described vital sign box, from which the computer can read the above-described program and/or data, and with which the above-described program and/or data that are read execute the above-described functions with collaborating with the above-described computer also belongs to the present invention.

Moreover, an information aggregation that is a program and/or data for letting a computer execute all or part of functions of the above-described vital sign box, from which the computer can read the above-described program and/or data, and with which the above-described program and/or data that are read execute the above-described functions with collaborating with the above-described computer also belongs to the present invention.

The data includes data structure, a data format, and a kind of data. The medium includes a recording medium such as ROM, a communication medium such as the Internet, and a transmission medium such as light, a radio wave, and a sound wave. The bearing medium includes, for example, a recording medium recording a program and/or data, a transmission medium transmitting a program and/or data, and the like.

The processability by a computer includes readability by a computer in case of, for example, a recording medium such as ROM, and processability of a program and/or data, which are objects of transmission and have been actually transmitted, by a computer in case of a transmission medium.

The information aggregation includes, for example, software such as a program and/or data.

Apparently from the above description, the present invention can provide an vital sign box that has means of being able to take a picture with flexibly changing an imaging object and/or an imaging angle.

In addition, the present invention can provide an vital sign box that has a vital sensor that can input a measurement into memory without letting a user perform a manual input.

Furthermore, the present invention can provide an vital sign box including a display to clearly display the fluctuations of measurements in a predetermined period that are measured and recorded by a vital sensor.

Moreover, the present invention can provide an vital sign box including a speaker outputting a measurement, which is measured by a vital sensor, with using sound.

In addition, the present invention can provide an vital sign box that includes imaging means of taking a picture of an object, and can transmit an image of the object that is taken by the imaging means to a communication partner. Furthermore, the present invention can provide an vital sign box that receives information from a communication partner, and can perform bi-directional communication.

Moreover, the present invention can provide an vital sign box inquiring health conditions of a user of the vital sign box.

What is claimed is:

1. A vital sign box comprising: a plurality of vital sensors measuring predetermined biological, chemical, or physical conditions of a living body; a camera for taking a picture of a predetermined object; and a housing containing the plurality of vital sensors and the camera, wherein the camera when the vital sign box is used is rotatable, and can be fixed at a predetermined angle.

2. The vital sign box according to claim 1, further comprising a base that is rotatable, can be fixed at a predetermined angle, and houses the camera at the time of detachment.

3. The vital sign box according to claim 1, wherein the camera is detachable.

4. The vital sign box according to claim 1, wherein the camera has a lighting section emitting light to the object.

5. The vital sign box according to claim 1, further comprising a display displaying an object whose image is taken by the camera.

6. The vital sign box of claim 1 wherein the plurality of vital sensors transmits measurements of the plurality of predetermined biological, chemical, or physical conditions, using an electric wave, the vital sign box further comprising;

a reception sensor receiving measurements from the plurality of vital sensors;

memory recording measurements received by the reception sensor; and a housing containing the plurality of vital sensors, the reception sensor, and the memory.

7. The vital sign box according to claim 6, wherein the electric wave is an infrared ray having a predetermined wavelength.

8. The vital sign box of claim 1 wherein the housing comprises a lid that contains the plurality of vital sensors and the display.

9. The vital sign box according to claim 8, wherein the display is movable;

wherein the housing has a display fixing section to fix the display; and wherein the display lies in a bottom section of the housing at the time of non-use and can be fixed in a status that the display stands to the bottom section of the housing with using the display fixing section at the time of use.

10. The vital sign box of claim 1 further comprising:

a speaker outputting measurements, measured by the vital sensors, by sound, the speaker located in the housing.

11. The vital sign box of claim 1 further comprising:

a memory recording measurements measured by the vital sensors and/or objects whose images are taken by the camera; and a communication terminal of transmitting all or part of measurements measured by the vital sensors, an object whose image is taken by the camera, measurements recorded in the memory, and objects recorded in the memory;

wherein the memory, and the communication terminal are located in the housing.

12. The vital sign box according to claim 11, wherein the communication terminal receives predetermined information from a communication partner, and wherein the vital sign box comprises a display that is contained in the housing, and not only displays all or part of measurements measured by the vital sensors, an object whose image is taken by the camera, measurements recorded in the memory, and objects recorded in the memory, but also displays information from the communication partner inputted by the communication terminal.

13. The vital sign box according to claim 12, wherein one of information from the communication partner, which is displayed in the display, is arrowhead information for specifying a predetermined position of the display, and the arrowhead is displayed in the display with all or part of measurements measured by the vital sensors, an object whose image is taken by the camera, measurements recorded in the memory, and objects recorded in the memory that are displayed in the display.

14. The vital sign box according to claim 13, wherein the arrowhead information is coordinate information of the position when the arrowhead is let to be displayed in the display, and the display has shape information of the arrowhead to be displayed and displays the arrowhead on the basis of the coordinate information from the communication partner.

15. The vital sign box of claim 1 further comprising:

a microphone inputting sound; and a communication terminal transmitting sound inputted by the microphone; the microphone and the communication terminal located in the housing.

16. The vital sign box of claim 1 further comprising:

a display displaying inquiry items to a user;

an inquiry result input section of inputting an inquiry result to inquiries in the display;

a communication terminal transmitting the inquiry result inputted by the inquiry result input section; wherein the display, the inquiry result input section, and the communication terminal are located in the housing.

17. The vital sign box according to claim 16, wherein the communication terminal is a device inputting predetermined information from a communication partner to whom the inquiry result is sent and the display also displays information from the communication partner that is inputted by the communication terminal.

18. The vital sign box according to claim 16, wherein the communication terminal is a device inputting predetermined information from a communication partner to whom the inquiry result is sent, and the vital sign box further comprises a speaker that is contained in the housing and outputs information from the communication partner, which is inputted by the communication terminal, with using sound.

19. A vital sign box comprising: a plurality of vital sensors measuring predetermined biological, chemical, or physical conditions of a living body; and a housing with a lid that contains at least the plurality of vital sensors, wherein the lid has a shank that becomes a substantially shaft when the lid is opened and closed;

wherein the shank is provided in the housing so that a main body of the housing has a front section and a rear section to the shank; and wherein the lid can be fixed in a status that the lid stands to a bottom section of the vital sign box with using the shank when the vital sign box is used.

20. The vital sign box according to claim 19, further comprising a display that is provided and fixed inside the lid of the housing, and displays measurements measured by the vital sensors.

21. A vital sign box comprising:

a plurality of vital sensors measuring predetermined biological, chemical, or physical conditions of a living body;

memory recording measurements measured by the vital sensors;

a display that displays measurements measured by the vital sensors, and/or a plurality of measurements recorded in the memory, and determines a display range and/or a display scale with each of the measurements, which are displayed, being as a reference; and a housing that contains the plurality of vital sensors, the memory, and the display.

22. The vital sign box according to claim 21, wherein each of the measurement to be a reference is a newest measurement and the item to be determined is a display range.

23. The vital sign box according to claim 21, wherein, when at least one of the plurality of vital sensors measures upper and lower limits of the predetermined condition substantially at the same time, the display simultaneously displays the measurements, which are measured and are upper and lower limits, and/or a plurality of measurements, which are recorded in the memory, with classifying the measurements into the upper limits and the lower limits whose display areas are divided separately.

24. A vital sign box comprising:

a plurality of vital sensors measuring predetermined biological, chemical, or physical conditions of a living body;

a power supply section that is provided so as not to contact with the vital sensors and supplies electric power from the outside of the vital sign box to all or part of the plurality of vital sensors with using an electromagnetic wave by electromagnetic induction; and a housing containing the plurality of vital sensors, and the power supply section.

25. The vital sign box according to any one of claims 1, 6, 19, 8, 21, 10, 11, 24, 15, or 16, wherein the housing has a lid and a main body; wherein a clamp for closing the lid and fixing the lid to the main body of the housing is provided in each of a main body of the housing and the lid; and wherein a handle is provided in the main body of the housing.

26. A vital sign box comprising:
a speaker outputting inquiry items to a user by sound;
an inquiry result input section inputting an inquiry result to inquiries from the speaker;
a communication terminal transmitting the inquiry result inputted by the inquiry result input section; and
a housing containing the speaker, the inquiry result input section, and the communication terminal;
wherein the housing has a lid and a main body; wherein a clamp for closing the lid and fixing the lid to the main body of the housing is provided for each of the main body of the housing and the lid; and wherein a handle is provided in the main body of the housing.

27. The vital sign box according to claim 26, wherein the communication terminal is a device inputting predetermined information from a communication partner to whom the inquiry result is sent, and the speaker also outputs information from the communication partner, which is inputted by the communication terminal, with using sound.

28. The vital sign box according to claim 26, wherein the communication terminal is a device inputting predetermined information from a communication partner to whom the inquiry result is sent, and the vital sign box further comprises a display that is contained in the housing and displays information from the communication partner that is inputted by the communication terminal.

29. The vital sign box according to any one of claims 1–2, 3, or 4–28, further comprising a password input section of inputting a password of a user, wherein measurements measured by the vital sensors, and/or an object whose image is taken by the camera are managed with being associated with a password inputted in the password input unit.

30. The vital sign box according to any one of claims 1–2, 3, or 4–28, wherein all or part of the plurality of vital sensors and/or the camera each have an electric power storage section storing electric power.

31. The vital sign box according to any one of claims 1–2, 3, or 4–28 further comprising a display displaying usage of a vital sign box.

32. The vital sign box according to claim 31, wherein all or part of the usage is displayed by an image.

33. The vital sign box according to claim 32, wherein the image is a graphic image of measurements measured by a vital sensor.

34. The vital sign box according to claim 31, wherein the display is a touch panel type liquid crystal display and changes display contents by a predetermined portion of the liquid crystal display being touched by a user.

35. A medium that bears a program and/or data for letting a computer execute all or part of functions of the vital sign box according to claim 31, the medium with which a computer can perform processing.

36. An information aggregation, wherein the information aggregation is a program and/or data for letting a computer execute all or part of functions of the vital sign box according to claim 31.

37. The vital sign box according to any one of claims 1–2, 3, or 4–28, further comprising a speaker outputting usage of a vital sign box by sound.

38. The vital sign box according to claim 37, further comprising: a display displaying usage of a vital sign box; and a change instruction input section of inputting an instruction for changing an output of the usage from an output where sound from the speaker is used to an output where display in the display is used.

39. The vital sign box according to any one of claims 5, 20, 8, 21, 12, 16, or 28, wherein the display is a touch panel type display having a software keyboard function.

40. A vital sign box comprising:
a speaker outputting inquiry items to a user by sound;
an inquiry result input section inputting an inquiry result to inquiries from the speaker;
a communication terminal transmitting the inquiry result inputted by the inquiry result input section;
a housing containing the speaker, the inquiry result input section, and the communication terminal; and
a password input section of inputting a password of a user, wherein measurements measured by the vital sensors, and/or an object whose image is taken by the camera are managed with being associated with a password inputted in the password input unit.

41. A vital sign box comprising:
a speaker outputting inquiry items to a user by sound;
an inquiry result input section inputting an inquiry result to inquiries from the speaker;
a communication terminal transmitting the inquiry result inputted by the inquiry result input section;
a housing containing the speaker, the inquiry result input section, and the communication terminal;
wherein all or part of the plurality of vital sensors and/or the camera each have an electric power storage section storing electric power.

42. The vital sign box according to claim 40 or claim 41, wherein the communication terminal is a device inputting predetermined information from a communication partner to whom the inquiry result is sent, and the vital sign box further comprises a display that is contained in the housing and displays information from the communication partner that is inputted by the communication terminal.

43. A vital sign box comprising:
a speaker outputting inquiry items to a user by sound;
an inquiry result input section inputting an inquiry result to inquiries from the speaker;
a communication terminal transmitting the inquiry result inputted by the inquiry result input section;
a housing containing the speaker, the inquiry result input section, and the communication terminal; and
a display displaying usage of a vital sign box;
wherein the display is a touch panel type liquid crystal display and changes display contents by a predetermined portion of the liquid crystal display being touched by a user.

44. The vital sign box according to claim 43, wherein all or part of the usage is displayed by an image.

45. The vital sign box according to claim 44, wherein the image is a graphic image of measurements measured by a vital sensor.

46. The vital sign box according to claim 43, further comprising a password input section of inputting a password of a user, wherein measurements measured by the vital sensors, and/or an object whose image is taken by the camera are managed with being associated with a password inputted in the password input unit.

47. The vital sign box according to claim 43, wherein all or part of the plurality of vital sensors and/or the camera each have an electric power storage section storing electric power.

48. The vital sign box according to any one of claims 40–47, wherein the communication terminal is a device inputting predetermined information from a communication partner to whom the inquiry result is sent, and the speaker also outputs information from the communication partner, which is inputted by the communication terminal, with using sound.

49. The vital sign box according to any one of claims 43–47, wherein the communication terminal is a device inputting predetermined information from a communication partner to whom the inquiry result is sent, and the vital sign box further comprises the display that is contained in the housing and displays information from the communication partner that is inputted by the communication terminal.

* * * * *

UNITED STATES PATENT AND TRADEMARK OFFICE
CERTIFICATE OF CORRECTION

PATENT NO. : 6,800,059 B2
DATED : October 5, 2004
INVENTOR(S) : Muraki et al.

It is certified that error appears in the above-identified patent and that said Letters Patent is hereby corrected as shown below:

<u>Title page,</u>
Item [56], References Cited, OTHER PUBLICATIONS, add -- Japanese Official Action dated March 23, 2004 --

<u>Column 41,</u>
Line 12, "40-47" should read -- 40, 41, and 43-47 --.

Signed and Sealed this

Fifteenth Day of March, 2005

JON W. DUDAS
*Director of the United States Patent and Trademark Office*